(12) United States Patent
Daly

(10) Patent No.: US 7,157,272 B2
(45) Date of Patent: Jan. 2, 2007

(54) CONSTRUCTS FOR GENE EXPRESSION ANALYSIS

(75) Inventor: John Daly, City Beach (AU)

(73) Assignee: Gene Stream Pty Ltd., City Beach (AU)

( * ) Notice: Subject to any disclaimer, the term of this patent is extended or adjusted under 35 U.S.C. 154(b) by 0 days.

(21) Appl. No.: 10/658,093

(22) Filed: Sep. 9, 2003

(65) Prior Publication Data

Related U.S. Application Data

(63) Continuation-in-part of application No. PCT/AU02/00351, filed on Mar. 8, 2002.

(60) Provisional application No. 60/274,770, filed on Mar. 9, 2001.

(51) Int. Cl.
  C12N 15/79 (2006.01)
  C12N 15/09 (2006.01)
  C12N 15/82 (2006.01)
  C12N 15/85 (2006.01)
  C12P 21/04 (2006.01)

(52) U.S. Cl. .................. 435/320.1; 435/69.7; 435/455; 435/419; 435/325; 536/23.4; 536/24.1

(58) Field of Classification Search ............. 435/320.1, 435/6, 69.1, 325; 536/23.1; 530/350
See application file for complete search history.

(56) References Cited

U.S. PATENT DOCUMENTS

| 5,464,758 A | 11/1995 | Gossen et al. |
|---|---|---|
| 5,625,048 A | 4/1997 | Tsien et al. |
| 5,650,135 A | 7/1997 | Contag et al. |
| 5,777,079 A | 7/1998 | Tsien et al. |
| 5,804,387 A | 9/1998 | Cormack et al. |
| 6,130,313 A | 10/2000 | Li et al. |
| 2004/0002056 A1* | 1/2004 | Lorens et al. .................. 435/5 |
| 2004/0091866 A1* | 5/2004 | Giordano et al. ............. 435/6 |

FOREIGN PATENT DOCUMENTS

| WO | WO 95/29244 | 11/1995 |
|---|---|---|
| WO | WO 99/14346 | 3/1999 |

OTHER PUBLICATIONS

Promega, pGL3-control vector, accessed online Dec. 3, 2004.*
Fang et al, Multiple cis Regulatory Elements for Maximal Expression of the Cauliflower Mosaic Virus 35S Promoter in Transgenic Plants, 1989, The Plant Cell, vol. 1, pp. 141-150.*
Primig et al, A novel GFPneo vector designed for the isolation and analysis of enhancer elements in transfected mammalian cells, Gene, 1998, vol. 215, pp. 181-189.*
Zhao et al, Comparison of Enhanced Green Fluorescent Protein and Its Destabilized Form as Transcription reporters, Methods in Enzymology, vol. 302, 1999, pp. 32-38.*
Eureka Biosciences, The Role of Polyadenylation in mRNA Decay, downloaded Sep. 13, 2005, Eureka.com.*
Andersen et al, New Unstable Variants of Green Fluorescent Protein for Studies of Transient Gene Expression in Bacteria, Appl Environ Microbiol, Jun. 1998, p. 2240-2246, vol. 64, No. 6.*
Herrero et al, Transposon Vectors Containing Non-Antibiotic Resistance Selection Markers for Cloning and Stable Chromosomal Insertion of Foreign Genes in Graham-Negative Bacteria, J Bacteriol, Nov. 1990, p. 6557-6567, vol. 172, No. 11.*
pUC18, pUC19,; description and restriciton map, downloaded Sep. 14, 2005, Fermentas.com.*
pMAMneo vector information, pMAMneo-LUC vector information, downloaded Sep. 14, 2005, Clontech.com*
Kessler et al, Requirements of AAUAAA and adjacent downstream sequences for SV40 early polyadenylation, NAR, 1986, p. 4939-4952, vol. 14, No. 12.*
Mateus and Avery, Destabilized green fluorescent protein for monitroing dynamic changes in yeast gene expression with flow cytometry, Yeast, 2000, p. 1313-1323, vol. 16.*
Watch et al, New Heterologout Modules for Classical or PCR-based Gene Disruptions in *Saccharomyces cerevisiae*, Yeast, 1994, p. 1793-1808, vol. 10.*
Watch et al, Heterologous HIS3 Marker and GFP Reporter Modules for PCR-targeting in *Saccharomyces cerevisiae*, Yeast, 1997, p. 1065-1075, vol. 13.*
Bennetzen and Hail, The Primary Structure of the *Saccharomyces cerevisiae* Gene for Alcohol Dehydrogenase I, JBC, 1982, p. 3018-3025, vol. 257, No. 6.*
Veyrune, et al., "c-fos mRNA instability determinants present with both the coding and the 3' non coding region link the degradation of this mRNA to its translation" Oncogene 11:2127-2134 (1995).
Maurer et al., "An AU-rich sequence in the 3'-UTR of plasminogen activator inhibitor type 2 (PAI-2) mRNA promotes PAI-2 mRNA decay and provides a binding site for nuclear HurR" Nucleic Acids Research 27(7):1664-1673 (1999).
Dean et al., "The 3' Unstranslated Region fo Tumor Necrosis Factor Alpha mRNA is a Target of the mRNA-Stabilizing Factor HuR" Molecular and Cellular Biology 21(3):721-730 (Feb. 2001).

(Continued)

Primary Examiner—Scott D. Priebe
Assistant Examiner—Maria B Marvich
(74) Attorney, Agent, or Firm—Knobbe Martens Olson and Bear, LLP

(57) ABSTRACT

The present invention relates generally to constructs and their use in gene expression or gene regulation assays. More particularly, the present invention provides expression vectors and/or reporter vectors providing kinetics of protein expression with improved temporal correlation to promoter activity. Even more particularly, the invention provides expression vectors comprising a transcribable polynucleotide which comprises a sequence of nucleotides encoding a RNA element that modulates the stability of a transcript corresponding to the transcribable polynucleotide. The present invention provides, inter alia, novel vectors, useful for identifying and analysing cis- and trans-acting regulatory sequences/factors as well as vectors and genetically modified cell lines or organisms that are particularly useful for drug screening and drug discovery.

37 Claims, 24 Drawing Sheets

OTHER PUBLICATIONS

Provost and Tremblay, "Length Increase of the Human α-Globin 3'-Untranslated Region Disrupts Stability of the Pre-mRNA but Not That of the Mature mRNA" The Journal of Biological Chemistry 275(39):30248-30255 (Sep. 29, 2000).

Short et al., "Structural Determinants for Post-transcriptional Stabilization of Lactate Dehydrogenase A mRNA by the Protein Kinase C Signal Pathway" the Journal of Biological Chemistry 275(17):12963-12969 (Apr. 28, 2000).

Yeilding et al., "c-myc mRNA Is Down-regulated during Myogenic Differentiation by Accelerated Decay That Depends on Translation of Regulatory Coding Elements" The Journal of Biological Chemistry 273(25):15749-15757 (Jun. 19, 1998).

Yeilding and Lee, "Coding Elements in Exons 2 and 3 Target c-myc mRNA Downregulation during Myogenic Differentiation" Molecular and Cellular Biology 17(5):2698-2707 (May 1997).

Chen and Shyu, "AU-rich elements: characterizations and importance in mRNA degradation" TIBS 20:465-470 (Nov. 1995).

Dandekar et al., "Systematic genomic screening and analysis of mRNA in untranslated regions and mRNA precursors: combining experimental and computational approaches" Bioinformatics 14(3):271-278 (1998).

Darzynkiewics et al., "Laser-Scanning Cytometry: A New Instrumentation with Many Applications" Experimental Cell Research 249:1-19(1999).

Gallie et al., "The histone 3'-terminal stem-loop is necessary for translation in Chinese hamster ovary cells" Nucleic Acids Research 24(10):1954-1962 (1996).

Gasdaska et al., "Regulation of Human Thioredoxin Reductase Expression and Activity by 3'-Untranslated Region Slenocysteine Insertion Sequence and mRNA Instability Elements" The Journal of Biological Chemistry 274(36):25379-25385 ( Sep. 3, 1999).

Gramolini et al., "Distinct regions in the 3' unstranslated region are responsible for targeting and stabilizing utrophin transcripts in skeletal muscle cells" The Journal of Cell Biology 154(6):1173-1183 (Sep. 17, 2001).

Henics et al., "Mammalian Hsp70 and Hsp110 Proteins Blind to RNA Motifs Involved in mRNA Stability" The Journal of Virological Chemistry 274(24):17318-17324 (Jun. 11, 1999).

Holcik and Loebhaber, "Four highly stable eukaryotic mRNA's assemble 3' untranslated region RNA-protein complexes sharing cis and trans components" Proc. Natl. Acd. Sci. USA 94:2410-2414 (Mar. 1997).

Huet el al., Cyclin A Expression Is Under Negative Transcriptional Control during the Cell Cycle Molecular and Cellular Biology 16(7):3789-3798 (Jul. 1996).

Lagnado et al., "AUUUA Is Not Sufficient To Promote Poly(A) Shortening and Degradation of an mRNA: the Funcitonal Sequence within AU-Rich Elements May be UUAUUUA(U/A)(U/A)" Molecular and Cellular Biology 14(12):7984-7995 (Dec. 1994).

Laterza et al., "Mapping and functional analysis of an instability element in phospoenolpypurvate carboxykinase mRNA" Am J Physiol Tenal Physiol 279:F866-F873 (2000).

Leclerc et al., "Development of a Destabilized Firefly Luciferase Enzyme for Measurement of Gene Expression" BioTechniques 29:590-601 (Sep. 2000).

Lee et al., "Regulation of Cyclin D1 DNA Topoisomerase I, and Proliferating Cell Nuclear Antigen Promoters During the Cell Cycle" Gene Expression 4:95-109 (1995).

Li et al., "Generation of Destabilized Green Fluorescent Protein as a Transcription Reporter" The Journal of Biological Chemistry 273(52):34970-34975 (Dec. 25, 1998).

Liu et al., "a1 Adrenergic Agonist Induction of $p21^{wasf1/cip1}$ mRNA Stability in Transfected HepG2 Cells Correlates with the Increased Binding of an AU-rich Element Binding Factor" The Journal of Biological Chemistry 275(16):11846-11851 (Apr. 21, 2000).

Newman et al., "DST Sequences, Highly Conserved among Plant SAUR Genes, Target Reporter Transcripts for Rapid Decay in Tobacco" The Plant Cell 5:7-1-714 (Jun. 1993).

Peng et al., "Functional Characterization of a Non-AUUUA AU-Rich Element from the c-jun Proto-Oncogene mRNA: Evidence for a Novel Class of AU-Rich Elements" Molecular and Cellular Biology 16(4):1940-1499 (Apr. 1996).

Ross, Jeff, "mRNA Stability in Mammalian Cells" Microbiological Reviews 59(3):423-450 (Sep. 1995).

Saito et al., "Okadaic Acid-Stimulated Degradation of p35, and Activator of CDK5, by Porteasome in Cultured Neurons" Biochemical and Biophysical Research communications 225:775-778 (1998).

Schiavone et al., "A conserved AU-rich element in the 3 untranslated region of bcl-2 mRNA is endowed with a destabilizing function that is involved in bcl-2 down-regulation during apoptosis" The FASEB Jornal 14:174-184 (Jan. 2000).

Shyu et al., "The c-fos transcript is targeted for rapid decay by two distinct mRNA degradation pathways"Genes * Development 3:60-72 (1989).

Surdej and Jacobs-Lorena, "Developmental Regulation of bicoid mRNA Stability Is Mediated by the First 43 Nucleotides of the 3' Untranslated Region" Molecular and Cellular Biology 18(5):2892-2900 (May 1998).

Thomson et al., "Iron-regulatory proteins, iron-responsive elements and ferritin mRNA translation" The International Journal of Biochemistry & Cell Biology 31:1139-1152 (1999).

Vazhappilly and Sucher, "Turnover analysis of N-methyl- -aspartate receptor subunit NR1 protein in PC12 cells" Neuroscience Letters 318:153-157 (2002).

Xu et al., "Modulation of the Fate of Cytoplasmic mRNA by AU-Rich Elements: Key Sequence Features Controlling mRNA Deadenylation and Decay" Molecular and Cellular Biology, 17(8):4611-4621 (Aug. 1997).

Yu and Russell, "Structural and Functional Analysis of an mRNP Complex That Mediates the High Stability of Human β-Globin mRNA" Molecular and Cellular Biology 21(17):5879-5888 (Sep. 2001).

Zhou et al., "Regulation of the Stability of Heat-Stable Antigen mRNA by Interplay between Two Novel cis Elements in the 3' Untranslated Region" Molecular and Cellular Biology 18(2):815-826 ( Feb. 1998).

Zubiaga et al., "The Nonamer UUAUUUAUU Is the Key AU-Rich Sequence Motif That Mediates the mRNA Degradation" Molecular and Cellular Biology 15(4):2219-2230 (1995).

Giles et al. JBC 278 (5):2937-2946 (2003).

Rogers et al., "Amino Acid Sequences Common to Rapidly Degraded Proteins: The PEST Hypothesis," *Science,* 234:364-368 (1986).

* cited by examiner

Figure 1
Expression Vectors Encoding a Destabilised mRNA
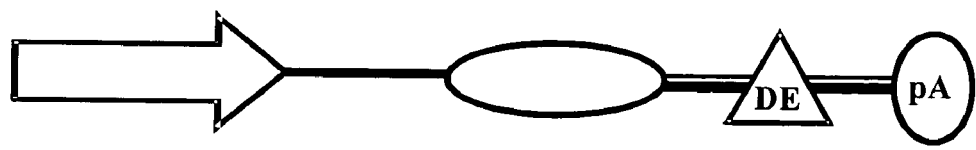
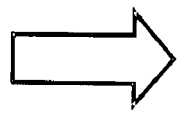 Any promoter or promoter element
 Protein or polypeptide encoding region
 mRNA destabilising element
 Polyadenylation signal
 5'-untranslated region (5'-UTR)
 3'-untranslated region (3'-UTR)

Figure 2
Transcription Reporter Vectors
Fig. 2a. Vector Series 2
Fig. 2b. Vector Series 3
Fig. 2c. Vector Series 4
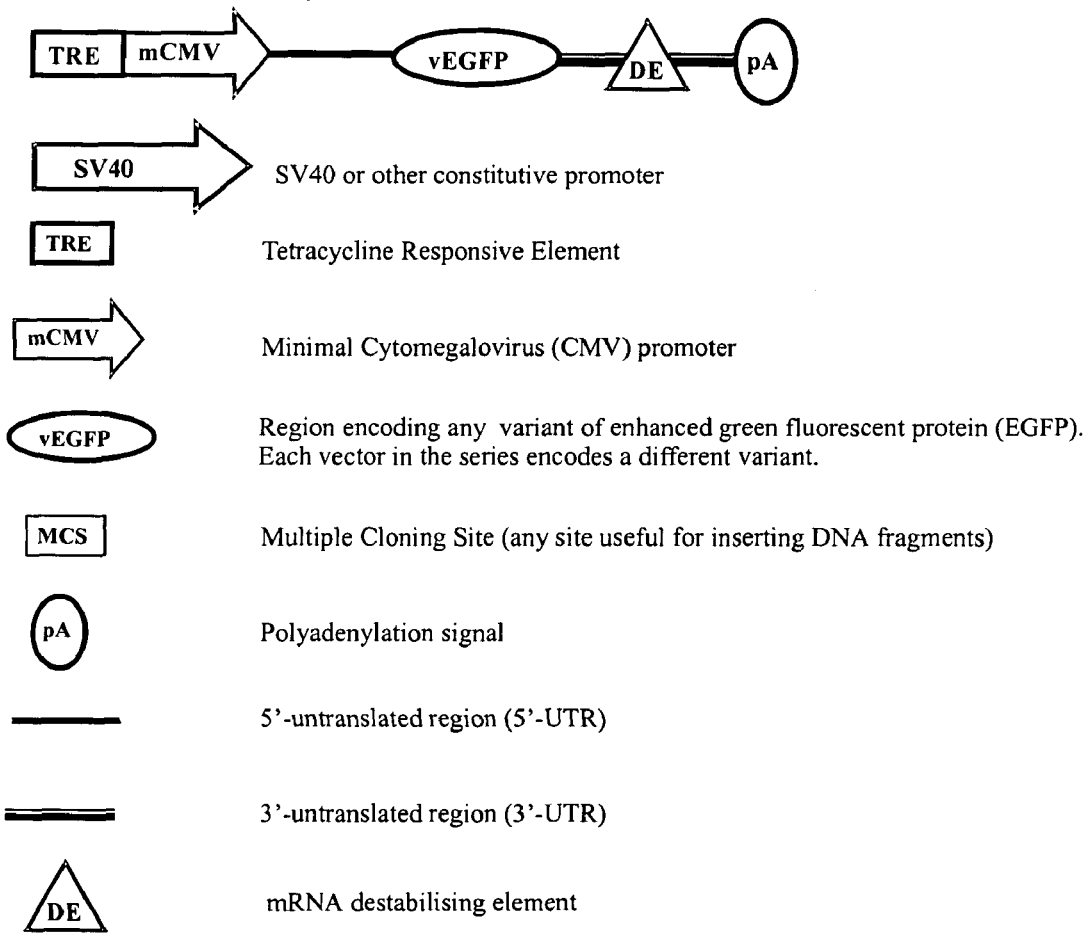

Figure 3

Bi-directional Transcription Reporter Vectors

Fig. 3a. Vector Series 5

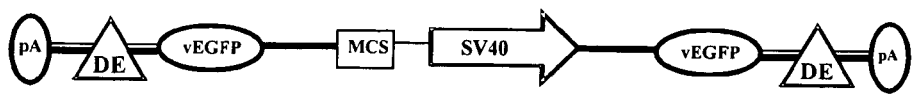

Fig. 3b. Vector Series 6

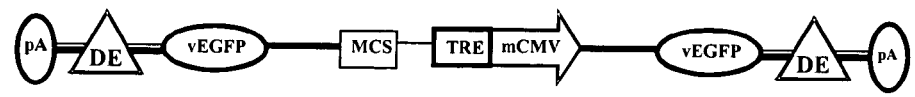

| | |
|---|---|
| SV4 ⇒ | SV40 or other constitutive |
| TRE | Tetracycline Responsive |
| mCMV ⇒ | Minimal Cytomegalovirus (CMV) |
| vEGFP | Region encoding an enhanced green fluorescent protein Each vector in the series encodes a |
| MCS | Multiple Cloning Site (any site useful for inserting |
| pA | Polyadenylation |
| — | 5'-untranslated region (5'- |
| = | 3'-untranslated region (3'- |
| △DE | mRNA destabilising |
| ___ | Spacer region to separate promoters. Can contain additional polyadenylation signals. |

Figure 4

Reporter Vectors For Studying Post-transcriptional Regulation

Fig. 4a. Vector Series 7

Fig. 4b. Vector Series 8

   Tetracycline Responsive Element

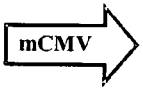   Minimal Cytomegalovirus (CMV) promoter

   Region encoding any variant of enhanced green fluorescent protein (EGFP) Each vector in the series encodes a different variant.

   Multiple Cloning Site (any site useful for inserting DNA fragments)

   Polyadenylation signal

   5'-untranslated region (5'-UTR)

   3'-untranslated region (3'-UTR)

Evidence For Errors Associated with Co-transfection in Luciferase-based

Evidence For Errors Associated with Dual Luciferase Assay.

SEQUENCE LISTING

```
<160> NUMBER OF SEQ ID NOS: 57

<210> SEQ ID NO 1
<211> LENGTH: 9
<212> TYPE: RNA
<213> ORGANISM: mammalian

<400> SEQUENCE: 1 uuauuuauu                                                                 9

<210> SEQ ID NO 2
<211> LENGTH: 9
<212> TYPE: RNA
<213> ORGANISM: mammalian

<400> SEQUENCE: 2 uuauuuaww                                                                 9

<210> SEQ ID NO 3
<211> LENGTH: 5
<212> TYPE: RNA
<213> ORGANISM: mammalian

<400> SEQUENCE: 3 auuua                                                                     5

<210> SEQ ID NO 4
<211> LENGTH: 4
<212> TYPE: RNA
<213> ORGANISM: mammalian

<400> SEQUENCE: 4 auuu                                                                      4
```

```
<210> SEQ ID NO 5
<211> LENGTH: 13
<212> TYPE: RNA
<213> ORGANISM: Artificial Sequence
<220> FEATURE:
<223> OTHER INFORMATION: AUUUAx3 Version 1

<400> SEQUENCE: 5
auuuauuuau uua                                                          13

<210> SEQ ID NO 6
<211> LENGTH: 15
<212> TYPE: RNA
<213> ORGANISM: Artificial Sequence
<220> FEATURE:
<223> OTHER INFORMATION: AUUUAx3 Version 2

<400> SEQUENCE: 6
auuuaauuua auuua                                                        15

<210> SEQ ID NO 7
<211> LENGTH: 6
<212> TYPE: DNA
<213> ORGANISM: Artificial Sequence
<220> FEATURE:
<223> OTHER INFORMATION: HindIII site

<400> SEQUENCE: 7 aagctt                                                                   6

<210> SEQ ID NO 8
<211> LENGTH: 129
<212> TYPE: DNA
<213> ORGANISM: Artificial Sequence
<220> FEATURE:
<223> OTHER INFORMATION: Clontech's d1 mutant of MODC

<400> SEQUENCE: 8
aagcttagcc atggcttccc gccggcggtg gcggcgcagg atgatggcac gctgcccatg        60
tcttgtgccc aggagagcgg gatggaccgt caccctgcag cctgtgcttc tgctaggatc       120
aatgtgtag                                                              129

<210> SEQ ID NO 9
<211> LENGTH: 56
<212> TYPE: RNA
<213> ORGANISM: Artificial Sequence
<220> FEATURE:
<223> OTHER INFORMATION: RNA destabilising linker

<400> SEQUENCE: 9
uuauuuauug gcgguuauuu auucggcguu auuuauugcg cguuauuuau uacuag            56

<210> SEQ ID NO 10
<211> LENGTH: 11
<212> TYPE: DNA
<213> ORGANISM: Artificial Sequence
<220> FEATURE:
<223> OTHER INFORMATION: EclHK1 recognition sequence
<220> FEATURE:
<221> NAME/KEY: misc_feature
<222> LOCATION: (1)..(8)
<223> OTHER INFORMATION: n = any nucleotide

<400> SEQUENCE: 10
```

```
gacnnnnngt c                                                          11

<210> SEQ ID NO 11
<211> LENGTH: 11
<212> TYPE: DNA
<213> ORGANISM: Artificial Sequence
<220> FEATURE:
<223> OTHER INFORMATION: EclHK1 recognition sequence Example 1
<220> FEATURE:
<221> NAME/KEY: misc_feature
<222> LOCATION: (4)..(5)
<223> OTHER INFORMATION: n = any nucleotide
<220> FEATURE:
<221> NAME/KEY: misc_feature
<222> LOCATION: (7)..(8)
<223> OTHER INFORMATION: n = any nucleotide

<400> SEQUENCE: 11
gacnntnngt c                                                          11

<210> SEQ ID NO 12
<211> LENGTH: 11
<212> TYPE: DNA
<213> ORGANISM: Artificial Sequence
<220> FEATURE:
<223> OTHER INFORMATION: EclHK1 recognition sequence Example 2
<220> FEATURE:
<221> NAME/KEY: misc_feature
<222> LOCATION: (4)..(5)
<223> OTHER INFORMATION: n = any nucleotide
<220> FEATURE:
<221> NAME/KEY: misc_feature
<222> LOCATION: (7)..(8)
<223> OTHER INFORMATION: n = any nucleotide

<400> SEQUENCE: 12
gacnnanngt c                                                          11

<210> SEQ ID NO 13
<211> LENGTH: 9
<212> TYPE: DNA
<213> ORGANISM: mammalian

<400> SEQUENCE: 13 ttatttatt                                                              9

<210> SEQ ID NO 14
<211> LENGTH: 75
<212> TYPE: DNA
<213> ORGANISM: mammalian

<400> SEQUENCE: 14
aaaacgtttt attgtgtttt taatttattt attaagatgg attctcagat atttatattt     60
ttattttatt ttttt                                                      75

<210> SEQ ID NO 15
<211> LENGTH: 226
<212> TYPE: DNA
<213> ORGANISM: mammalian

<400> SEQUENCE: 15
atgcatgatc aaatgcaacc tcacaacctt ggctgagtct tgagactgaa agatttagcc     60
ataatgtaaa ctgcctcaaa ttggactttg ggcataaaag aacttttta tgcttaccat    120 ctttttttt tctttaacag atttgtattt aagaattgtt tttaaaaaat tttaagattt    180
acacaatgtt tctctgtaaa tattgccatt aaatgtaaat aactttt                  226
```

<210> SEQ ID NO 16
<211> LENGTH: 73
<212> TYPE: DNA
<213> ORGANISM: mammalian

<400> SEQUENCE: 16
gtatgtttaa attatttta tacactgccc tttcttacct ttctttacat aattgaaata    60
ggtatcctga cca                                                     73

<210> SEQ ID NO 17
<211> LENGTH: 53
<212> TYPE: RNA
<213> ORGANISM: mammalian

<400> SEQUENCE: 17
aguaauauuu auauauuuau auuuuaaaa uauuuauuua uuuauuuauu uaa          53

<210> SEQ ID NO 18
<211> LENGTH: 53
<212> TYPE: DNA
<213> ORGANISM: mammalian

<400> SEQUENCE: 18
agtaatattt atatatttat atttttaaaa tatttattta tttatttatt taa          53

<210> SEQ ID NO 19
<211> LENGTH: 73
<212> TYPE: DNA
<213> ORGANISM: mammalian

<400> SEQUENCE: 19
aacgttttat tgtgttttta atttatttat taagatggat tctcagatat ttatattttt    60
attttatttt ttt                                                      73

<210> SEQ ID NO 20
<211> LENGTH: 70
<212> TYPE: DNA
<213> ORGANISM: mammalian

<400> SEQUENCE: 20
ttttattgtg tttttaattt atttattaag atggattctc agatatttat attttattt    60 tattttttt                                                           70

<210> SEQ ID NO 21
<211> LENGTH: 89
<212> TYPE: RNA
<213> ORGANISM: mammalian

<400> SEQUENCE: 21
uuucguuaac uguguaugua cauauauaua uuuuuaauu ugauuaaagc ugauuacugu    60
gaauaaacag cuucaugccu uuguaaguu                                     89

<210> SEQ ID NO 22
<211> LENGTH: 89
<212> TYPE: DNA
<213> ORGANISM: mammalian

<400> SEQUENCE: 22
tttcgttaac tgtgtatgta catatatata tttttaatt tgattaaagc tgattactgt    60

```
gaataaacag cttcatgcct ttgtaagtt                                          89

<210> SEQ ID NO 23
<211> LENGTH: 6
<212> TYPE: RNA
<213> ORGANISM: mammalian

<400> SEQUENCE: 23 aauaaa                                                                    6

<210> SEQ ID NO 24
<211> LENGTH: 89
<212> TYPE: RNA
<213> ORGANISM: Artificial Sequence
<220> FEATURE:
<223> OTHER INFORMATION: Mutant of Peng c-jun ARE

<400> SEQUENCE: 24
uuucguuaac uguguaugua cauauauaua uuuuuuaauu ugauuaaagc ugauuacugu         60
ggauccacag cuucaugccu uuguaaguu                                          89

<210> SEQ ID NO 25
<211> LENGTH: 89
<212> TYPE: DNA
<213> ORGANISM: Artificial Sequence
<220> FEATURE:
<223> OTHER INFORMATION: DNA encoding mutant of Peng c-jun ARE

<400> SEQUENCE: 25
tttcgttaac tgtgtatgta catatatata ttttttaatt tgattaaagc tgattactgt         60
ggatccacag cttcatgcct ttgtaagtt                                          89

<210> SEQ ID NO 26
<211> LENGTH: 36
<212> TYPE: RNA
<213> ORGANISM: mammalian

<400> SEQUENCE: 26
ucuauuuauu aauauuuaac auuauuuaua uauggg                                  36

<210> SEQ ID NO 27
<211> LENGTH: 36
<212> TYPE: DNA
<213> ORGANISM: mammalian

<400> SEQUENCE: 27
tctatttatt aatatttaac attatttata tatggg                                  36

<210> SEQ ID NO 28
<211> LENGTH: 124
<212> TYPE: RNA
<213> ORGANISM: mammalian

<400> SEQUENCE: 28
cucuauuuau uuaaauauuu aacuuuaauu uauuuuugga uguauuguuu acuaacuuuu         60
agugcuuccc acuuaaaaca uaucaggcuu cuauuuauuu aaauauuuaa auuuuauauu        120
uauu                                                                    124

<210> SEQ ID NO 29
<211> LENGTH: 124
<212> TYPE: DNA
<213> ORGANISM: mammalian
```

```
<400> SEQUENCE: 29
ctctatttat ttaaatattt aactttaatt tattttggga tgtattgttt actaactttt     60
agtgcttccc acttaaaaca tatcaggctt ctatttattt aaatatttaa attttatatt    120
tatt                                                                 124

<210> SEQ ID NO 30
<211> LENGTH: 46
<212> TYPE: RNA
<213> ORGANISM: mammalian

<400> SEQUENCE: 30
auaaacccua auuuuuuua uuuaaguaca uuuugcuuuu aaaguu                     46

<210> SEQ ID NO 31
<211> LENGTH: 46
<212> TYPE: DNA
<213> ORGANISM: mammalian

<400> SEQUENCE: 31 ataaaccta atttttttta tttaagtaca ttttgctttt aaagtt                     46

<210> SEQ ID NO 32
<211> LENGTH: 119
<212> TYPE: RNA
<213> ORGANISM: mammalian

<400> SEQUENCE: 32
uagaauauuu auuaccucug auaccucaac ccccauuucu auuuauuuac ugagcuucuc     60
ugugaacgau uuagaaagaa gcccaauauu auaauuuuuu ucaauauuua uuauuuuca    119

<210> SEQ ID NO 33
<211> LENGTH: 119
<212> TYPE: DNA
<213> ORGANISM: mammalian

<400> SEQUENCE: 33
tagaatattt attacctctg atacctcaac ccccatttct atttatttac tgagcttctc     60
tgtgaacgat ttagaaagaa gcccaatatt ataattttt tcaatattta ttattttca    119

<210> SEQ ID NO 34
<211> LENGTH: 105
<212> TYPE: RNA
<213> ORGANISM: mammalian

<400> SEQUENCE: 34
ucagcuauuu acugccaaag ggaaauauca uuuauuuuuu acauuauuaa gaaaaaagau     60
uuauuuauuu aagacagucc caucaaaacu ccgucuuugg aaauc                    105

<210> SEQ ID NO 35
<211> LENGTH: 105
<212> TYPE: DNA
<213> ORGANISM: mammalian

<400> SEQUENCE: 35
tcagctattt actgccaaag ggaaatatca tttatttttt acattattaa gaaaaaagat     60
ttatttattt aagacagtcc catcaaaact ccgtctttgg aaatc                    105

<210> SEQ ID NO 36
```

-continued

```
<211> LENGTH: 34
<212> TYPE: RNA
<213> ORGANISM: mammalian

<400> SEQUENCE: 36
auuauuuauu auuauuuau uauuuauuua uuua                         34

<210> SEQ ID NO 37
<211> LENGTH: 34
<212> TYPE: DNA
<213> ORGANISM: mammailan

<400> SEQUENCE: 37
attatttatt atttatttat tatttattta ttta                        34

<210> SEQ ID NO 38
<211> LENGTH: 55
<212> TYPE: RNA
<213> ORGANISM: mammalian

<400> SEQUENCE: 38 uauuuauuc cauuaaggcu auuuauuau guauuuaugu auuuauuau uuauu    55

<210> SEQ ID NO 39
<211> LENGTH: 55
<212> TYPE: DNA
<213> ORGANISM: mammalian

<400> SEQUENCE: 39
tattttattc cattaaggct atttatttat gtatttatgt atttatttat ttatt 55

<210> SEQ ID NO 40
<211> LENGTH: 9
<212> TYPE: DNA
<213> ORGANISM: mammalian

<400> SEQUENCE: 40 ttatttaww                                                    9

<210> SEQ ID NO 41
<211> LENGTH: 5
<212> TYPE: DNA
<213> ORGANISM: mammalian

<400> SEQUENCE: 41 attta                                                        5

<210> SEQ ID NO 42
<211> LENGTH: 4
<212> TYPE: DNA
<213> ORGANISM: mammalian

<400> SEQUENCE: 42 attt                                                         4

<210> SEQ ID NO 43
<211> LENGTH: 25
<212> TYPE: DNA
<213> ORGANISM: Artificial Sequence
<220> FEATURE:
<223> OTHER INFORMATION: Consensus DST sequence
<220> FEATURE:
<221> NAME/KEY: misc_feature
<222> LOCATION: (5)..(5)
<223> OTHER INFORMATION: n = from 2-9 nucleotides, wherein each
```

-continued individual nucleotide can be any nucleotide
<220> FEATURE:
<221> NAME/KEY: misc_feature
<222> LOCATION: (15)..(15)
<223> OTHER INFORMATION: n = from 3-8 nucleotides, wherein each
      individual nucleotide can be any nucleotide

<400> SEQUENCE: 43
ggagncatag attanmwwtt tgtay                                      25

<210> SEQ ID NO 44
<211> LENGTH: 25
<212> TYPE: DNA
<213> ORGANISM: Soybean
<220> FEATURE:
<221> NAME/KEY: misc_feature
<222> LOCATION: (5)..(5)
<223> OTHER INFORMATION: n = 5 nucleotides , wherein each individual
      nucleotide can be any nucleotide
<220> FEATURE:
<221> NAME/KEY: misc_feature
<222> LOCATION: (15)..(15)
<223> OTHER INFORMATION: n = 8 nucleotides , wherein each individual
      nucleotide can be any nucleotide

<400> SEQUENCE: 44
ggagncatag attanaaatt tgtac                                      25

<210> SEQ ID NO 45
<211> LENGTH: 25
<212> TYPE: DNA
<213> ORGANISM: Arabidopsis
<220> FEATURE:
<221> NAME/KEY: misc_feature
<222> LOCATION: (5)..(5)
<223> OTHER INFORMATION: n = 9 nucleotides , wherein each individual
      nucleotide can be any nucleotide
<220> FEATURE:
<221> NAME/KEY: misc_feature
<222> LOCATION: (15)..(15)
<223> OTHER INFORMATION: n = 8 nucleotides , wherein each individual
      nucleotide can be any nucleotide

<400> SEQUENCE: 45
ggaancatag atcgncaatg cgtat                                      25

<210> SEQ ID NO 46
<211> LENGTH: 30
<212> TYPE: RNA
<213> ORGANISM: mammalian

<400> SEQUENCE: 46
guucuugcuu caacaguguu ugaacggaac                                30

<210> SEQ ID NO 47
<211> LENGTH: 30
<212> TYPE: DNA
<213> ORGANISM: mammalian

<400> SEQUENCE: 47
gttcttgctt caacagtgtt tgaacggaac                                30

<210> SEQ ID NO 48
<211> LENGTH: 29
<212> TYPE: RNA
<213> ORGANISM: mammalian

<400> SEQUENCE: 48

-continued

```
gauuaucggg agcagugucu uccauaauc                                29

<210> SEQ ID NO 49
<211> LENGTH: 29
<212> TYPE: DNA
<213> ORGANISM: mammalian

<400> SEQUENCE: 49
gattatcggg agcagtgtct tccataatc                                29

<210> SEQ ID NO 50
<211> LENGTH: 226
<212> TYPE: DNA
<213> ORGANISM: mammalian

<400> SEQUENCE: 50
atgcatgatc aaatgcaacc tcacaacctt ggctgagtct tgagactgaa agatttagcc    60
ataatgtaaa ctgcctcaaa ttggactttg ggcataaaag aacttttta tgcttaccat   120 ctttttttt tctttaacag atttgtattt aagaattgtt tttaaaaaat tttaagattt   180
acacaatgtt tctctgtaaa tattgccatt aaatgtaaat aacttt              226

<210> SEQ ID NO 51
<211> LENGTH: 30
<212> TYPE: RNA
<213> ORGANISM: mammalian
<220> FEATURE:
<221> NAME/KEY: misc_feature
<222> LOCATION: (4)..(4)
<223> OTHER INFORMATION: n = from 20-40 nucleotides, wherein individual
      nucleotides are selected from any nucleotide
<220> FEATURE:
<221> NAME/KEY: misc_feature
<222> LOCATION: (19)..(19)
<223> OTHER INFORMATION: n is a, c, g, or u

<400> SEQUENCE: 51
uganccaaag gyyyuuyuna rrrccaccca                                30

<210> SEQ ID NO 52
<211> LENGTH: 30
<212> TYPE: DNA
<213> ORGANISM: mammalian
<220> FEATURE:
<221> NAME/KEY: misc_feature
<222> LOCATION: (4)..(4)
<223> OTHER INFORMATION: n = from 20-40 nucleotides, wherein individual
      nucleotides are selected from any nucleotide
<220> FEATURE:
<221> NAME/KEY: misc_feature
<222> LOCATION: (19)..(19)
<223> OTHER INFORMATION: n is a, c, g, or t

<400> SEQUENCE: 52
tganccaaag gyyyttytna rrrccaccca                                30

<210> SEQ ID NO 53
<211> LENGTH: 16
<212> TYPE: RNA
<213> ORGANISM: mammalian
<220> FEATURE:
<221> NAME/KEY: misc_feature
<222> LOCATION: (5)..(5)
<223> OTHER INFORMATION: n = any number of nucleotides, wherein
      individual nucleotides are selected from any nucleotide
<220> FEATURE:
<221> NAME/KEY: misc_feature
<222> LOCATION: (11)..(11)
```

-continued

```
<223> OTHER INFORMATION: n = any number of nucleotides, wherein
      individual nucleotides are selected from pyrimidines

<400> SEQUENCE: 53
yccancccwy yucycc                                                  16

<210> SEQ ID NO 54
<211> LENGTH: 46
<212> TYPE: DNA
<213> ORGANISM: mammalian

<400> SEQUENCE: 54
cctcctgccc gctgggcctc ccaacgggcc ctcctcccct ccttgc                 46

<210> SEQ ID NO 55
<211> LENGTH: 5
<212> TYPE: DNA
<213> ORGANISM: mammalian

<400> SEQUENCE: 55 cctcc                                                              5

<210> SEQ ID NO 56
<211> LENGTH: 9
<212> TYPE: DNA
<213> ORGANISM: mammalian

<400> SEQUENCE: 56 cctcctgcc                                                          9

<210> SEQ ID NO 57
<211> LENGTH: 14
<212> TYPE: DNA
<213> ORGANISM: mammalian

<400> SEQUENCE: 57
ccctcctccc ctgg                                                    14
```

CONSTRUCTS FOR GENE EXPRESSION ANALYSIS

This application is a continuation-in-part application of co-pending International Patent Application No. PCT/AU02/00351 filed Mar. 8, 2002, which designates the United States, and was published in English, and which claims priority under 35 U.S.C. § 119(e) to U.S. Provisional Application No. 60/274,770, filed Mar. 9, 2001

BACKGROUND OF THE INVENTION

This invention relates generally to constructs and their use in gene expression or gene regulation assays. More particularly, the present invention provides expression vectors and/or reporter vectors providing kinetics of protein expression with improved temporal correlation to promoter activity. The present invention provides, inter alia, novel vectors and cell lines useful for modulating gene expression, identifying and analysing regulatory sequences, new targets and reagents for therapeutic intervention in human diseases and for drug-screening.

Bibliographic details of the publications referred to by author in this specification are collected at the end of the description.

The rapidly increasing sophistication of recombinant DNA technology is greatly facilitating research and development in the medical and allied health fields. A particularly important area of research is the use of expression vectors to study gene expression. However, until now, a real-time analysis of gene expression has been limited by the lack of suitably designed vectors.

Reporter assays permit an understanding of what controls the expression of a gene of interest e.g., DNA sequences, transcription factors, RNA sequences, RNA-binding proteins, signal transduction pathways and specific stimuli.

Furthermore, reporter assays can be used to identify aspects of gene regulation that serve as new targets for therapeutic intervention in human disease. Reporter assays can potentially be used to screen drugs for their ability to modify gene expression. However, the cost and time required for current reporter assay systems, together with the inaccuracies caused by the lengthy response times, has limited this application.

Genomic sequences have promoter sequences, generally upstream of the coding region, which dictate the cell specificity and inducibility of transcription and thereby affect the level of expression of protein products.

Specific sequence elements, typically rich in the nucleotide bases A and U and often located in the 3'-UTR of a gene, affect the stability of the mRNA and thereby affect the level of expression of the protein product. RNA-binding proteins bind certain mRNA sequences and thereby regulate mRNA stability and protein expression. Other sequences and trans-acting proteins modulate other post-transcriptional pathways such as translational efficiency, mRNA splicing and mRNA export into the cytoplasm.

A common application of gene reporter assays is the study of DNA sequences that regulate transcription. Typically, these sequences are located in the promoter region, 5' of the transcription start site. Such DNA elements are tested by cloning them into a similar site within a reporter plasmid, such that they drive and/or regulate transcription and therefore, expression of reporter protein. The reporter protein should be distinguishable from endogenous proteins and easily quantified. Various reporter proteins are used, the most common being luciferase, chloramphenicol transferase (CAT) and β galactosidase (β-gal).

The reporter protein is quantified in an appropriate assay and often expressed relative to the level of a control reporter driven by a ubiquitous promoter such as for example the promoter SV40. The control reporter must be distinguishable from the test reporter and is contained on a separate vector that is co-transfected with the test vector and used to control for transfection efficiency. Such assays are based on the premise that cells take up proportionally equal amounts of both vectors. Transient transfections of plasmid vectors are most commonly used.

The assays described above are used to identify a promoter region or the specific elements within a promoter. Alternatively, they are used to study the response to various stimuli of a promoter or regulatory element. In some applications, the reporter constructs, or the transfected cells, are placed into an organism to study promoter function in vivo.

Another application of these reporter assays is the study or measurement of signal transduction pathways upstream of a specific promoter. For example, a promoter dependent on mitogen activated protein kinase (MAPK) for transcription can be linked to a reporter construct and used to measure the level of MAPK activation (or MAPK-dependent transcription) in cells. This technique can be utilized with a variety of informative promoters or enhancers and can be applied to cells or living organisms such as transgenic mice. For example, a photon camera can be used to measure luciferase reporter activity in whole mice containing a luciferase reporter linked to a promoter of interest (Contag, et al, 1997).

Luciferase is the most commonly used reporter assay for in vitro systems. The Dual Luciferase assay (DLA; Promega, Madison, Wis., USA), is an improvement over other luciferase based systems in that both test and control reporter can essentially be measured in the same assay. As an example of current use, a typical DLA protocol is provided as follows:

The putative promoter element is cloned upstream of a firefly luciferase reporter gene such that it drives its expression. This plasmid is transiently transfected into a cell line, along with a control plasmid containing the *Renilla* luciferase gene driven by the SV40 promoter. ~2–50% of cells take up plasmid and express the reporters for ~3 days. The kinetics of expression involve an increase during the first ~24 h as luciferase protein accumulates, followed by a decrease from ~48 h as the number of plasmids maintained within the cells declines. 24–48 h after transfection, cells are harvested and lysed. Cell lysates are incubated with substrates specific to firefly luciferase and activity (light emission) is measured using a luminometer (96 well plate or individual samples). Additional substrates are then added, which inactivate firefly luciferase but allow *Renilla* luciferase to generate light. *Renilla* luciferase activity can then be measured.

The level of firefly luciferase activity is dependent, not only on promoter activity, but also on transfection efficiency. This varies greatly, depending on the amount of DNA, the quality of the DNA preparation and the condition of the cells. The co-transfected control plasmid (*Renilla* luciferase driven by the SV40 promoter) is used to correct for these variables, based on the premise that *Renilla* luciferase activity is proportional to the amount of firefly luciferase plasmid taken up by the cells. Data are expressed as firefly luciferase activity/*Renilla* luciferase activity.

The disadvantages of the Dual Luciferase assay are as follows:
  (i) Reagents are expensive and perishable and must be freshly prepared.
  (ii) Generally this assay involves the preparation of cell lysates, which is time consuming and adds inaccuracy. e.g., loss of cells during lysis, pipetting errors, residual buffer/medium altering volumes.
  (iii) Each sample yields only one datum point being the total activity of the cell population. No information is gained concerning the percentage of cells that express the reporter, nor the amount of expression per cell.
  (iv) The transfection control (*Renilla*) does not always correct for huge variation in transfection efficiencies because:
      (a) Certain DNA preparations transfect/express poorly (perhaps due to reduced proportion of supercoiled DNA), but do not cause a corresponding decrease in the amount of co-transfected control plasmid.
      (b) There is evidence of cross-talk between the promoters of the two plasmids, such that control reporter activity is dependent on the construct with which it is co-transfected, e.g., expression of *Renilla* luciferase seems highest when co-transfected with a plasmid containing a strong promoter. Interference between promoters has also limited, if not prevented, the use of single plasmids expressing both test and control reporters.
      (c) A common application of both transcriptional and post-transcriptional studies is to measure activation/suppression by various stimuli (e.g., PMA, EGF, hormones). Unfortunately, SV40, RSV, TK and probably many other ubiquitously expressed promoters are activated by a variety of stimuli. Since these promoters are used to drive expression of the transfection control reporter (*Renilla*), these reporters do not give a true reflection of transfection efficiency following such treatments. (Ibrahim et al. 2000).
      (d) Differences in the half-lives of firefly vs *Renilla* luciferase proteins and perhaps mRNAs make the whole system very time-sensitive.
      (e) Rapidly diminishing light emission, particularly for *Renilla* luciferase, require absolute precision in the timing of measurement.
      (f) The relatively long half-lives of luciferase proteins and mRNAs effectively mask temporal changes in transcription (e.g., following various stimuli or treatments).

In existing post-transcriptional/mRNA stability reporter assays, candidate elements, thought to affect mRNA stability are cloned into the corresponding region of a reporter vector (e.g., firefly luciferase) driven by a constitutive promoter such as SV40 or RSV. Changes in expression relative to the empty vector (same vector without element of interest) are assumed to be the result of altered mRNA stability or translational efficiency. More complex assays are required to distinguish the two possibilities. As with the preliminary described transfection assays, a transfection control plasmid (e.g., *Renilla* luciferase driven by a constitutive promoter such as SV40 or RSV) is co-transfected to allow correction for transfection efficiency. These assays suffer from the following additional disadvantages:
  (1) Existing vectors were not designed for post-transcriptional studies and have no means for switching off transcription.
  (2) The purpose of these protocols is to study the post-transcriptional effects of candidate mRNA elements. However, these elements can also affect transcription of the reporter at the level of DNA. Furthermore, since the endogenous promoter of the gene of interest is not used, any transcriptional effects seen may have little physiological relevance.

Other systems for studying mRNA stability exist but involve direct measurement of the mRNA rather than a protein reporter. Due to the labour-intensive nature of protocols for quantifying mRNA, such systems are far more time consuming.

One system, for example, utilizes the c-fos promoter, which responds to serum induction with a brief burst of transcription. Putative instability elements are cloned into the 3-UTR of a Beta Globin (BBB) construct, which expresses the very stable beta globin mRNA under the control of a serum-inducible (c-fos) promoter. Transfected cells (generally NIH 3T3 cells) are first serum starved and then exposed to medium containing serum. The brief nature of the transcriptional response allows the kinetics of reporter mRNA degradation to be followed in a time course. This assay suffers from the following disadvantages:
  (i) Quantifying mRNA rather than reporter protein is very time consuming and is therefore not applicable to rapid screening.
  (ii) Can only be used in cells that support serum inducibility of the c-fos promoter. For example, many tumour cell lines maintain c-fos promoter activity in the absence of serum.
  (iii) In cells such as NIH 3T3 cells, which do have the desired serum response, serum deprivation causes a cell cycle block and subsequent addition of serum, releases the cells from this block in a synchronous manner. Therefore, mRNA stability can only be measured in specific stages of the cell cycle.
  (iv) In addition to activating the c-fos promoter, serum activates a multitude of other pathways, which introduce unwanted variables and prevent the study of more specific stimuli.

In another assay, cells are treated with drugs, such as Actinomycin D that inhibit transcription from all genes. The mRNA levels are measured in a time course to determine mRNA degradation rates. This system is used to study endogenous genes and suffers from the following disadvantages:
  (i) Transcriptional inhibitors are extremely toxic at doses required such that mRNA stability is often being measured in stressed or dying cells.
  (ii) Transcription inhibitors possess numerous unwanted activities including stabilization of certain mRNAs.
  (iii) The process blocks transcription from all genes such that many signal transduction cascades are blocked, whereas others are activated. Therefore, results may not be physiologically relevant.
  (iv) The technique is extremely labour intensive.
  (v) The technique is highly variable within and between assays.
  (vi) The technique is often not sensitive enough for transient transfection reporter assays, particularly in cells with low transfection efficiency.

There is a need therefore to develop improved vectors and systems for conducting gene expression assays and in particular post-transcriptional assays as well as assays that permit a more real-time determination of changes in gene expression.

SUMMARY OF THE INVENTION

The present invention is predicated in part on the development of a novel series of constructs and methods which permit inter alia modulation and determination of transcript stability and/or improved real-time determination of gene expression.

Accordingly, in one aspect of the present invention constructs are provided for assaying the activity of gene expression-modulating elements (e.g., transcriptional control elements and cis-acting regulatory elements) or for identifying elements of this type or agents that modulate their activity. These constructs generally comprise in operable linkage: a polynucleotide that encodes a polypeptide and a nucleic acid sequence that encodes a RNA element that modulates the stability of a transcript encoded by the polynucleotide. In some embodiments, the polypeptide has an intracellular half-life of less than about 1, 2 or 3 hours.

In some embodiments, the RNA element is a destabilising element that reduces the stability of the transcript. Suitably, in these embodiments, the nucleic acid sequence is, or is derived from, a gene selected from c-fos, c-jun, c-myc, GM-CSF, IL-3, TNF-alpha, IL-2, IL-6, IL-8, IL-10, Urokinase, bcl-2, SGLT1 (Na(+)-coupled glucose transporter), Cox-2 (cyclooxygenase 2), IL-8, PAI-2 (plasminogen activator inhibitor type 2), beta1-adrenergic receptor or GAP43. Illustrative examples of such nucleic acid sequences include, but are not limited to, the nucleotide sequences set forth in SEQ ID NOS 1 to 23, especially in SEQ ID NO:1, 13, 19 or 49, or biologically active fragments thereof, or variants or derivatives of these.

In other embodiments, the RNA element is a stabilising element that increases the stability of the transcript. Suitably, in these embodiments, the nucleic acid sequence is, or is derived from, a gene selected from alpha2 globin, alpha1 globin, beta globin, growth hormone, erythropoietin, ribonucleotide reductase R1 or m1 muscarinic acetylcholine.

In some embodiments, the polynucleotide and the nucleic acid sequence are heterologous to each other.

In some embodiments, the polypeptide comprises a protein-destabilising element, which is suitably selected from a PEST sequence, an ubiquitin, a biologically active fragment of an ubiquitin, or variant or derivative of these.

In some embodiments, the polypeptide is a reporter protein, which is suitably selected from an enzymatic protein or a protein associated with the emission of light (e.g., a fluorescent or luminescent protein). Illustrative examples of suitable reporter proteins include, but are not limited to, Luciferase, GFP, SEAP, CAT, or biologically active fragments thereof, or variants or derivatives of these. In other embodiments, the polypeptide is a protein having at least a light-emitting activity and a selection marker activity. In these embodiments, the polypeptide is suitably encoded by a chimeric gene which includes a coding sequence from a gene encoding a light-emitting protein and a coding sequence from a gene encoding a selectable marker protein. In certain embodiments, the light-emitting protein is selected from Green Fluorescent Protein, Luciferase and their biologically active fragments, variants and derivatives and the selectable marker protein is selected from kanamycin kinase, neomycin phosphotransferase, aminoglycoside phosphotransferase, puromycin N-acetyl transferase, puromycin resistance protein and their biologically active fragments, variants and derivatives.

In some embodiments, the constructs further comprise one or more of the following: a transcriptional control element for regulating expression of the polynucleotide and of the nucleic acid sequence; a cis-acting regulatory element (e.g., a transcriptional enhancer) for modulating the activity of the transcriptional control element; a reporter gene; at least one cloning site for introducing a sequence of nucleotides; a polyadenylation sequence; a selectable marker; an origin of replication; a translation modulating element (e.g., a translational enhancer) for modulating translation of a transcript encoded by the polynucleotide and an intron or other post-transcriptional regulatory element (e.g., woodchuck post-transcriptional regulatory element from woodchuck hepatitis virus, which is an example of a mRNA nuclear export signal) for modulating other aspects of post-transcriptional gene regulation. In certain illustrative examples, the constructs comprise in operable linkage: a polynucleotide that encodes a polypeptide and a nucleic acid sequence that encodes a RNA element that modulates the stability of a transcript encoded by the polynucleotide, wherein the construct lacks, but comprises a site for introducing, a gene expression-modulating element in operable connection with the polynucleotide and the nucleic acid sequence. In other illustrative examples, the constructs comprise a gene expression-modulating element in operable linkage with a polynucleotide that encodes a polypeptide and with a nucleic acid sequence that encodes a RNA element that modulates the stability of a transcript encoded by the polynucleotide, wherein the construct further comprises a site for introducing a post-transcriptional control element. In these examples, the polypeptide desirably has an intracellular half-life of less than about 1, 2 or 3 hours and more desirably comprises a protein-destabilising element.

In embodiments in which a construct comprises a cloning site, the cloning site is suitably selected from a multiple cloning site or a site that is cleavable enzymatically, chemically or otherwise to provide a linearised vector into which PCR amplification products are clonable directly.

The constructs are typically in the form of a vector. In some embodiments, the constructs are suitable for assaying the activity of a transcriptional control element or the activity of a cis-acting regulatory element or both.

In a related aspect, the present invention provides constructs for assaying the activity of gene expression-modulating elements (e.g., transcriptional control elements and cis-acting regulatory elements) or for identifying elements of this type or agents that modulate their activity. These constructs generally comprise in operable linkage: a polynucleotide that encodes a polypeptide comprising a protein-destabilising element, and a nucleic acid sequence that encodes a RNA element that modulates the stability of a transcript encoded by the polynucleotide. In some embodiments, the polypeptide is a reporter protein.

In another aspect, the present invention provides a cell comprising one or more constructs as broadly described above. Typically, the cell is selected from prokaryotic (e.g., bacterial) or eukaryotic cells (e.g., mammalian including human cells).

In yet another aspect, the present invention provides a genetically modified non-human organism comprising one or more constructs as broadly described above.

Still another aspect of the present invention provides methods for assaying the activity of a transcriptional control element. These methods generally comprise: (1) expressing from the transcriptional control element a polynucleotide that encodes a polypeptide and that is operably connected to a nucleic acid sequence that encodes a RNA element that modulates the stability of a transcript encoded by the polynucleotide; and (2) measuring the level or functional activity of the polypeptide produced from the expression. In some embodiments, the expression of the polynucleotide is carried out in the presence and absence of a test agent. In these embodiments, the methods further comprise comparing the level or functional activity of the polypeptide produced in the presence and absence of the test agent. Suitably, the expression of the polynucleotide is carried out in a first cell type or condition and in a second cell type or condition, wherein a difference in the level or functional activity of the polypeptide in the presence of the test agent between the cell types or conditions provides information on the effect of the test agent on those cell types or conditions (e.g., mode of action or specificity). In some embodiments, the activity of the transcriptional control element is a measure of a cellular event, which includes but is not limited to cell cycle progression, apoptosis, immune function, modulation of a signal transduction pathway, modulation of a regulatory pathway, modulation of a biosynthetic pathway, toxic response, cell differentiation and cell proliferation.

In some embodiments, the methods comprise: (1) expressing from a first transcriptional control element in a first construct a first polynucleotide that encodes a first polypeptide and that is operably connected to a nucleic acid sequence that encodes a RNA element that modulates the stability of a transcript encoded by the first polynucleotide; (2) measuring the level or functional activity of the first polypeptide produced from the first construct; (3) expressing from a second transcriptional control element in a second construct a second polynucleotide that encodes a second polypeptide and that is operably connected to a nucleic acid sequence that encodes a RNA element that modulates the stability of a transcript encoded by the second polynucleotide, wherein the expression of the second polynucleotide is carried out in the presence or absence of the test agent, and wherein the second transcriptional control element is different than the first transcriptional control element; (4) measuring the level or functional activity of the second polypeptide produced from the second construct; and (5) comparing the level or functional activity of the second polypeptide with the level or functional activity of the first polypeptide in the presence or absence of the test agent. The first construct and the second construct may be in the form of separate constructs or a single chimeric construct. For example, the first and second constructs may be present on the same vector or on separate vectors. Desirably, the first polypeptide and the second polypeptide are detectably distinguishable. The first construct and the second construct may be contained within a single cell or within different cells. In some embodiments, at least one of the first and second polypeptides has an intracellular half-life of less than about 1, 2 or 3 hours.

Still another aspect of the present invention provides methods for identifying an agent that modulates the activity of a gene expression-modulating element (e.g., transcriptional control elements and cis-acting regulatory elements). These methods generally comprise: (a) expressing under the control of the gene expression-modulating element a polynucleotide that encodes a polypeptide and a nucleic acid sequence that encodes a RNA element that modulates the stability of a transcript encoded by the polynucleotide in the presence and absence of a test agent; (b) measuring the level or functional activity of the polypeptide in the presence and absence of the test agent; and (c) comparing those levels or functional activities, wherein a difference between the level or functional activity of the polypeptide in the presence and absence of the test agent indicates that the test agent modulates the activity of the gene expression-modulating element. In some embodiments, the polypeptide comprises a protein-destabilising element. Suitably, the polypeptide has an intracellular half-life of less than about 1, 2 or 3 hours. In some embodiments, the polypeptide is a reporter protein.

In yet another aspect, the present invention provides constructs for identifying or assaying the activity of a cis-acting regulatory element. These constructs generally comprise a transcriptional control element in operable linkage with: a polynucleotide that encodes a polypeptide and a nucleic acid sequence that encodes a RNA element that modulates the stability of a transcript encoded by the polynucleotide, wherein the constructs further comprise a site for introducing cis-acting regulatory element or a nucleotide sequence suspecting of being a cis-acting regulatory element in operable linkage with the transcriptional control element. In illustrative examples, the constructs lack, but comprise a site for introducing, a cis-acting regulatory element in said operable linkage. In some embodiments, the transcriptional control element is a minimal promoter. In some embodiments of this type, the polypeptide comprises a protein-destabilising element. Suitably, the polypeptide has an intracellular half-life of less than about 1, 2 or 3 hours. In some embodiments, the polypeptide is a reporter protein. In some embodiments, the activity of the cis-acting regulatory element is a measure of a cellular event, which includes but is not limited to cell cycle progression, apoptosis, immune function, modulation of a signal transduction pathway, modulation of a regulatory pathway, modulation of a biosynthetic pathway, toxic response, cell differentiation and cell proliferation.

A further aspect of the present invention provides methods for assaying the activity of a post-transcriptional control element. These methods generally comprise: (1) expressing from a transcriptional control element a polynucleotide that encodes a polypeptide and that is operably linked to: a nucleic acid sequence that encodes the post-transcriptional control element; and (2) measuring the level or functional activity of the polypeptide produced from the expression. In some embodiments, the polypeptide comprises a protein-destabilising element. Suitably, the polypeptide has an intracellular half-life of less than about 1, 2 or 3 hours. In some embodiments, the polypeptide is a reporter protein. In some embodiments, the expression of the polynucleotide is carried out in the presence and absence of a test agent. In these embodiments, the methods desirably further comprise comparing the level or functional activity of the polypeptide produced in the presence and absence of the test agent. In some of these embodiments, the expression of the polynucleotide is carried out in a first cell type or condition and in a second cell type or condition, wherein a difference in the level or functional activity of the polypeptide in the presence of the test agent between the cell types or conditions provides information on the effect of the test agent on those cell types or conditions (e.g., mode of action or specificity). In some embodiments, the activity of the post-transcriptional control element is a measure of a cellular event, which includes but is not limited to cell cycle progression, apoptosis, immune function, modulation of a signal transduction pathway, modulation of a regulatory pathway, modulation of a biosynthetic pathway, toxic response, cell differentiation and cell proliferation.

In some embodiments, the methods comprise: (a) expressing from a first transcriptional control element in a first construct a first polynucleotide that encodes a first polypeptide and that is operably linked to: a nucleic acid sequence that encodes the post-transcriptional control element, wherein the expression of the first polynucleotide is optionally carried out in the presence or absence of a test agent; (b)

measuring the level or functional activity of the first polypeptide produced from the first construct; (c) expressing from a second transcriptional control element in a second construct a second polynucleotide, which encodes a second polypeptide but which is not operably linked to the nucleic acid sequence that encodes the post-transcriptional control element, wherein the second polypeptide is the same as, or different than, the first polypeptide, wherein the second transcriptional control element is the same as, or different than, the first transcriptional control element and wherein the expression of the second polynucleotide is optionally carried out in the presence or absence of the test agent; (d) measuring the level or functional activity of the second polypeptide produced from the second construct; and (e) comparing the level or functional activity of the second polypeptide with the level or functional activity of the first polypeptide optionally in the presence or absence of the test agent. In these embodiments, the first construct and the second construct may be in the form of separate constructs or a single chimeric construct. For example, the first and second constructs may be present on the same vector or on separate vectors. The first and second constructs may be contained within a single cell or within different cells. In certain embodiments, the first polypeptide and the second polypeptide are detectably distinguishable. Suitably, at least one of the first and second polypeptides has an intracellular half-life of less than about 1, 2 or 3 hours. In some embodiments of this type, one or both of the first and second polypeptides comprise(s) a protein-destabilising element. In some embodiments, the transcriptional control element is modulatable, including inducible or repressible promoters. In these embodiments, the methods desirably further comprise (1) inducing or repressing the first or second transcriptional control element; and (2) measuring changes in the level or functional activity of the first or second polypeptide over time.

In still a further aspect, the present invention provides methods for identifying a nucleotide sequence that encodes a post-transcriptional control element that modulates the expression of a RNA transcript from a first polynucleotide that encodes a polypeptide. These methods generally comprise: (i) expressing from a first transcriptional control element in a first construct the first polynucleotide, which is operably connected to a test nucleotide sequence suspected of encoding the post-transcriptional control element; (ii) expressing from a second transcriptional control element in a second construct a second polynucleotide, which encodes a second polypeptide, but which is not operably connected to the test nucleotide sequence, wherein the second polypeptide is the same as, or different than, the first polypeptide and wherein the second transcriptional control element is the same as, or different than, the first transcriptional control element; and (iii) comparing the level or functional activity of the polypeptides from the first and second constructs, wherein a difference between the level or functional activity of the first polypeptide and the level or functional activity of the second polypeptide indicates that the test nucleotide sequence encodes a post-transcriptional control element. In some embodiments, at least one of the first and second polypeptides has an intracellular half-life of less than about 1, 2 or 3 hours. In some embodiments, at least one of the first and second polypeptides comprises a protein-destabilising element. In some embodiments, the first and second polypeptides are reporter proteins. In some embodiments, the transcriptional control element is modulatable, including inducible or repressible promoters. In these embodiments, the methods desirably further comprise (1) inducing or repressing the first or second transcriptional control element; and (2) measuring changes in the level or functional activity of the first or second polypeptide over time.

In still another aspect, the present invention provides methods for identifying an agent that modulates the activity of a post-transcriptional control element that modulates the expression of a RNA transcript from a polynucleotide that encodes a polypeptide. These methods generally comprise: (a) expressing from a transcriptional control element the polynucleotide, which is operably connected to a nucleic acid sequence that encodes the post-transcriptional control element, wherein the expression of the polynucleotide is carried out in the presence and absence of a test agent; (b) measuring the level or functional activity of the polypeptide in the presence and absence of the test agent; and (c) comparing those levels or functional activities, wherein a difference between the level or functional activity of the polypeptide in the presence and absence of the test agent indicates that the test agent modulates the activity of the post-transcriptional control element. In some embodiments, the expression of the polynucleotide is carried out in a first cell type or condition and in a second cell type or condition, wherein a difference in the level or functional activity of the polypeptide in the presence of the test agent between the cell types or conditions provides information on the effect of the test agent on those cell types or conditions (e.g., mode of action or specificity). In some embodiments, the polypeptide comprises a protein-destabilising element. Suitably, the polypeptide has an intracellular half-life of less than about 1, 2 or 3 hours. In some embodiments, the polypeptide is a reporter protein. In some embodiments, the transcriptional control element is modulatable, including inducible or repressible promoters. In these embodiments, the methods desirably further comprise (1) inducing or repressing the first or second transcriptional control element; and (2) measuring changes in the level or functional activity of the first or second polypeptide over time.

In some embodiments, these methods comprise (i) expressing from a first transcriptional control element a first polynucleotide, which encodes a first polypeptide and which is operably connected to a nucleic acid sequence that encodes the post-transcriptional control element, wherein the expression of the first polynucleotide is carried out in the presence and absence of a test agent; (ii) measuring the level or functional activity of the polypeptide in the presence and absence of the test agent; (iii) expressing from a second transcriptional control element in a second construct a second polynucleotide, which encodes a second polypeptide, but which is not operably connected to the nucleic acid sequence, wherein the second polypeptide is the same as, or different than, the first polypeptide, wherein the second transcriptional control element is the same as, or different than, the first transcriptional control element and wherein the expression of the second polynucleotide is carried out in the presence or absence of the test agent; (iv) measuring the level or functional activity of the second polypeptide from the second construct in the presence or absence of the test agent; and (v) comparing the level or functional activity of the second polypeptide with the level or functional activity of the first polypeptide in the presence or absence of the test agent. In these embodiments, the first construct and the second construct may be in the form of separate constructs or a single chimeric construct. For example, the first and second constructs may be present on the same vector or on separate vectors. The first and second constructs may be contained within a single cell or within different cells. In some embodiments, at least one of the first and second polypeptides comprises a protein-destabilising element. Suitably, one or both of the first and second polypeptides has/have an intracellular half-life of less than about 1, 2 or 3 hours. Typically, the first polypeptide and the second polypeptide are detectably distinguishable. In some embodiments, the first and second polynucleotides are transcribed from the same transcriptional control element, illustrative examples of which include a bi-directional promoter.

In some embodiments, the transcriptional control element is modulatable. For example, the transcriptional control element may be repressible (e.g., a TRE or derivative thereof) or inducible. In these embodiments, the methods further comprise (A) inducing or repressing the first transcriptional control element; and (B) measuring a change in the level or functional activity of the polypeptide over time.

Still another aspect of the present invention provides constructs for identifying or assaying the activity of a post-transcriptional control element that modulates the expression of a transcript. These constructs generally comprise a transcriptional control element that is operably connected to: a polynucleotide from which the transcript is transcribed and which encodes a polypeptide having an intracellular half-life of less than about 3 hours; and a cloning site for introducing a nucleotide sequence that encodes, or is suspected to encode, the post-transcriptional control element. Suitably, the polypeptide has an intracellular half-life of less than about 1 or 2 hours. In some embodiments of this type, the polypeptide comprises a protein-destabilising element. In some embodiments, the polypeptide is a reporter protein.

Yet another aspect of the present invention provides constructs for identifying or assaying the activity of a post-transcriptional control element that modulates the expression of a transcript. These constructs generally comprise a transcriptional control element that is operably connected to: a polynucleotide from which the transcript is transcribed and which encodes a polypeptide comprising a protein-destabilising element; and a cloning site for introducing a nucleotide sequence that encodes, or is suspected to encode, the post-transcriptional control element. Suitably, the polypeptide has an intracellular half-life of less than about 1, 2 or 3 hours. In some embodiments, the polypeptide is a reporter protein.

Another aspect of the present invention provides methods for identifying a transcriptional control element. These methods generally comprise: (1) subjecting a construct to conditions sufficient for RNA and protein synthesis to occur, wherein the construct comprises in operable linkage: a nucleotide sequence suspected of having transcriptional control activity; a polynucleotide that encodes a polypeptide and a nucleic acid sequence that encodes a RNA element that modulates the stability of a transcript encoded by the polynucleotide; and (2) detecting the polypeptide produced from the construct. In some embodiments, the polypeptide comprises a protein-destabilising element. Suitably, the polypeptide has an intracellular half-life of less than about 1, 2 or 3 hours.

Yet another aspect of the present invention provides methods for identifying a cis-acting regulatory element that modulates the activity of a transcriptional control element. These methods generally comprise: (1) subjecting a construct to conditions sufficient for RNA and protein synthesis to occur, wherein the construct comprises in operable linkage: a nucleotide sequence suspected of having cis-acting regulatory activity; the transcriptional control element; a polynucleotide that encodes a polypeptide and a nucleic acid sequence that encodes a RNA element that modulates the stability of a transcript encoded by the polynucleotide; and (2) detecting the polypeptide produced from the construct. In some embodiments, the polypeptide comprises a protein-destabilising element. Suitably, the polypeptide has an intracellular half-life of less than about 1, 2 or 3 hours. In some embodiments, the polypeptide is a reporter protein.

In a further aspect, the present invention provides methods for assaying the activity of a transcriptional control element. These methods generally comprise: (i) expressing from the transcriptional control element a polynucleotide that encodes a polypeptide comprising a protein-destabilising element and that is operably connected to a nucleic acid sequence that encodes a RNA element that modulates the stability of a transcript encoded by the polynucleotide; and (ii) measuring the level or functional activity of the polypeptide produced from the construct.

BRIEF DESCRIPTION OF THE DRAWINGS

FIG. 1 is a schematic representation of expression vectors encoding a destabilising mRNA.

FIG. 2 is a schematic representation of transcription reporter vectors; FIG. 2a shows vector series 2; FIG. 2b shows vector series 3 and FIG. 2c shows vector series 4.

FIG. 3 is a schematic representation of Bi-directional transcription reporter vectors; FIG. 3a shows vector series 5 and FIG. 3b shows vector series 6.

FIG. 4 is a schematic representation of reporter vectors for studying post-transcriptional regulation; FIG. 4a shows vector series 7 and FIG. 4b shows vector series 8.

FIG. 5A shows that *Renilla* luciferase activity was dependent on the amount of DNA transfected. However, firefly luciferase activity (as shown in FIG. 5B) did not increase with increasing amounts of DNA, perhaps because the firefly DNA preparation was of poor quality. Consequently, the firefly/*Renilla* ratio (as shown in FIG. 5C), which would typically be used as a measure of the firefly promoter activity, varied considerably depending on the amount of DNA used. These data demonstrate that co-transfections with *Renilla* plasmids do not adequately control for the transfection efficiency of the firefly plasmid.

FIGS. 22A and 22B are graphical representations showing a time-course similar to that described in FIG. 15. BTY1N4 represents the EYFP reporter, with both protein- and mRNA-destabilising elements as described in FIG. 18. BTpuroY1N4 was constructed by inserting the puromycin coding sequence, in frame, at the 5' end of the coding sequence in BTY1N4, such that the reporter protein produced is a fusion of the puromycin-resistance protein, EYFP and the MODC destabilising sequence. As seen in FIG. 18, reporter levels from BTY1N4 decay rapidly after doxycycline (drug). As shown in FIG. 22A, a similar rate of decay was seen with the puromycin-fusion reporter, either when expressed transiently (BTpuroY1N4) or stably (BTpuroY1N4 stable cell line). The fact that we were able to select a stable cell line in puromycin shows that the puromycin resistance gene is active in this fusion protein and the detectable levels of fluorescence show that the EYFP component maintains fluorescent activity. The decay curves demonstrate that rapid decay of our destabilised reporters is reproducible in stably transfected cells and is not compromised with the fusion protein. Similarly, the neomycin-EYFP-MODC fusion protein (BTneoY1N4) also conferred antibiotic resistance (not shown) and expressed detectable levels of fluorescence that decayed rapidly after drug. FIG. 22B shows a similar but separate experiment utilising the same BTY1N4 and BTpuroY1N4 constructs. The wild-type ubiquitin sequence, followed by an arginine was cloned in frame and upstream of the coding sequence in these vectors to create BTuY1N4 and BTupuroY1N4 respectively. Upon translation of these reporters, the ubiquitin polypeptide is cleaved, to create a reporter protein with an N-terminal arginine and associated leader sequence that directs decay via the N-end rule. In particular, BTuY1N4 decayed extremely fast, reaching 50% of initial values after only ~1.7 hrs. This demonstrates that enhanced decay can be achieved by incorporating 2 different protein degradation signals.

FIGS. 15–22) confirm that both activation and inhibition of transcription are more easily detected and accurately quantified using the destabilised reporter vectors, compared to standard reporter vectors.

FIG. 26A) as compared to the standard vector (BNL; FIG. 26B). This is evidenced by the faster and more pronounced change in reporter levels following drug treatment.

FIG. 27A) as compared to the standard *Renilla* vector (BTRn; FIG. 27B).

FIG. 28A shows the ratio of green fluorescence to red fluorescence (in the absence of drug), expressed relative to the ratio with Promega 5'-UTR construct. The poor level of translation with the synthetic 5'-UTR, as well as the translational enhancer activities of Hsp70 and beta-globin 5'-UTRs are clearly evident. Interestingly, the puro-green construct appears to express at even higher levels. FIG. 28B shows that following a block in transcription, EGFP fluorescence decays at a similar rate with all constructs. This demonstrates that the different "steady state" expression levels seen in FIG. 28A are not caused by an effect of the 5'-UTR on mRNA (or protein) stability.

DETAILED DESCRIPTION OF THE INVENTION

1. Definitions and Abbreviations

Figure 5:
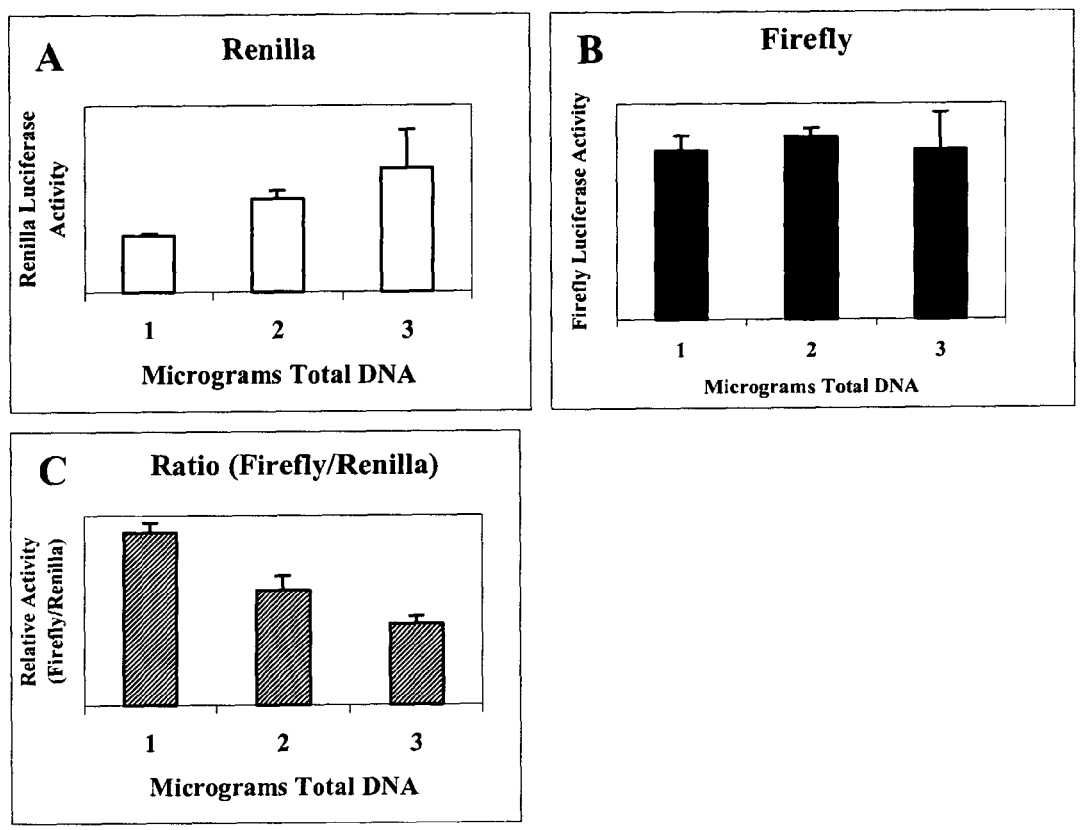
FIG. 5 is a graphical representation showing reporter activity as a function of the amount of DNA transfected. A single DNA preparation of a plasmid encoding firefly luciferase was mixed at a 30:1 ratio with a separate plasmid encoding *Renilla* luciferase. Both DNA preparations appeared normal in spectrophotometry (OD260/280) and on ethidium bromide stained agarose gels (data not shown). Different volumes of this mixture were transfected into cells such that the total quantity of DNA was 1, 2 or 3 micrograms but the ratio of firefly to *Renilla* plasmids remained the same. Specifically.
Figure 6:
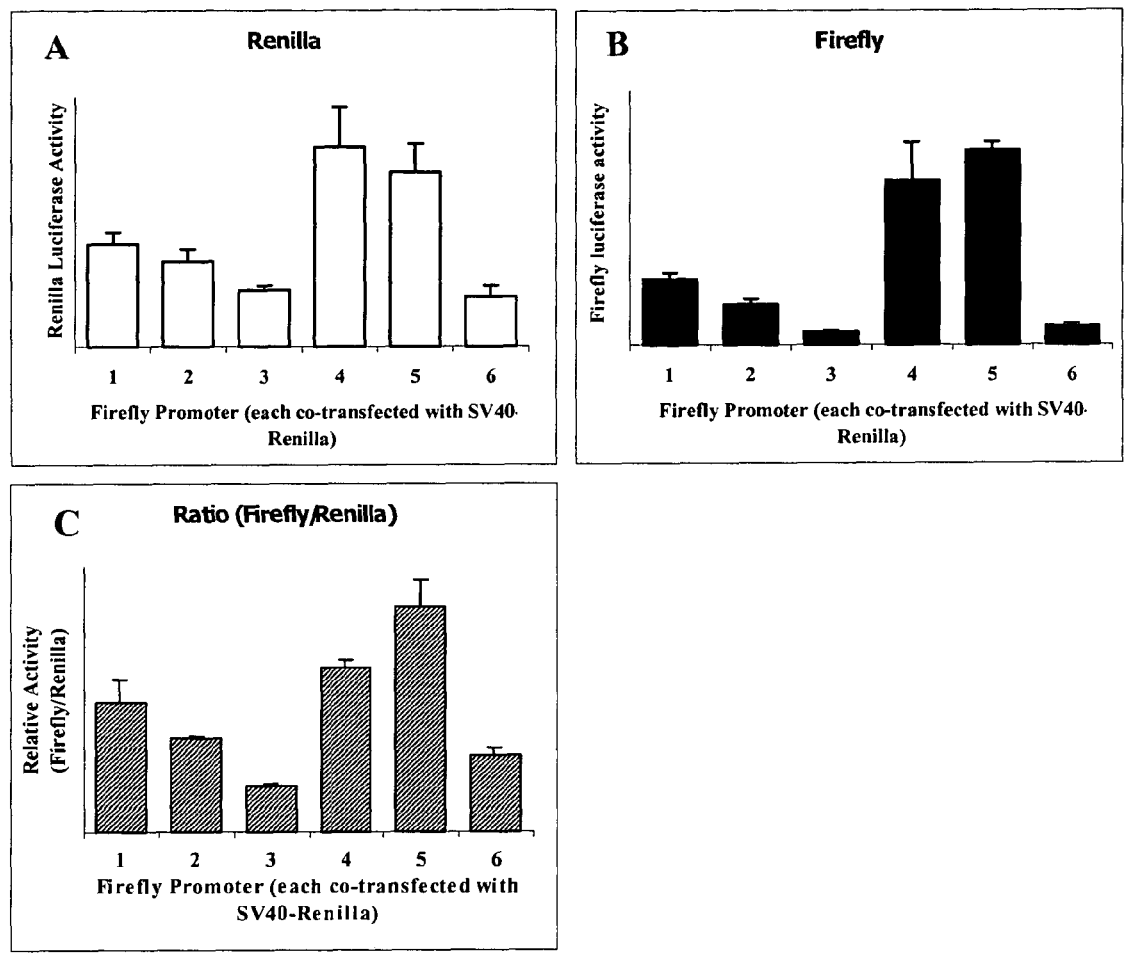
FIG. 6 is a graphical representation showing reporter activity for various promoter systems using the Dual Luciferase Assay. Six different promoter fragments (numbered 1–6) were cloned into pGL3 firefly luciferase plasmids. One microgram of each clone was co-transfected with 30 ng of *Renilla* (transfection control) plasmid, driven by an SV40 promoter. Firefly and *Renilla* luciferase activities were measured using the Dual Luciferase Assay (Promega, Madison, Wis., USA). Results are expressed as *Renilla* luciferase activity (A), Firefly luciferase activity (B) and firefly divided by *Renilla* activity (C). Similar results were seen in multiple experiments using at least 2 different preparations of each construct. *Renilla* luciferase activity (as shown in FIG. 6A) is intended as a transfection control and analysis of this result alone would suggest an unusually high variation in transfection efficiency. For example, *Renilla* luciferase activity is 3.5 fold higher when co-transfected with construct 4 compared to co-transfection with construct 3. Variations in DNA quality or errors in the quantification of DNA seem unlikely as sources of error since the same pattern was seen with a separate set of DNA preparations (data not shown). Firefly luciferase activity (as shown in FIG. 6B) is influenced by both transfection efficiency and differences between promoters 1–6. The pattern of differences is similar to that seen with *Renilla* (FIG. 6A). For example, 3 and 6 are low whilst 4 and 5 are high. However these differences between constructs are more marked with firefly (e.g., construct 4 is 12 fold higher than construct 3), suggesting that the activity of promoters 1–6 is somehow affecting expression of *Renilla* (or vice versa). Firefly/*Renilla* (FIG. 6C) is considered to be a measure of true firefly promoter activity (1–6) after correction for transfection efficiency (*Renilla*). Again a similar pattern is seen, suggesting that indeed 3 and 6 are the weakest promoters whilst 4 and 5 are the strongest. Whilst it is possible that promoter activity (FIG. 6C) coincidentally correlated with transfection efficiency (FIG. 6A), this possibility seems extremely unlikely given that similar results were obtained with numerous different constructs and multiple different preparations of the same construct. It seems more likely that the level of expression of *Renilla* luciferase is affected by the strength of the promoter construct with which it is co-transfected. Consequently, apparent differences between promoters 1–6 are likely to be an underestimation of the true differences.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "5'-UTR" is meant the 5' (upstream) untranslated region of a gene. Also used to refer to the DNA region encoding the 5'-UTR of the mRNA.

By "3'-UTR" is meant the region of a polynucleotide downstream of the termination codon of a protein-encoding region of that polynucleotide, which is not translated to produce protein.

By "about" is meant a quantity, level, value, dimension, size, or amount that varies by as much as 30%, preferably by as much as 20%, and more preferably by as much as 10% to a reference quantity, level, value, dimension, size, or amount.

By "ARE" is meant an AU-rich element in mRNA i.e., a sequence that contains a high proportion of adenine and uracil nucleotides. Also used to refer to the DNA region encoding such a mRNA element.

By "biologically active fragment" is meant a fragment of a full-length reference polynucleotide or polypeptide which fragment retains the activity of the reference polynucleotide or polypeptide, respectively.

By "CAT" is meant chloramphenicol acetyltransferase.

As used herein, the term "cis-acting sequence," "cis-acting regulatory element," "cis-regulatory region," "regulatory region" and the like shall be taken to mean any sequence of nucleotides, which when positioned appropriately relative to a transcriptional control element or to a transcribable sequence, is capable of modulating, at least in part, the activity of the transcriptional control element or the expression of the transcribable sequence. Those skilled in the art will be aware that a cis-acting regulatory element may be capable of activating, silencing, enhancing, repressing or otherwise altering the level of expression and/or cell-type-specificity and/or developmental specificity of a gene sequence at the transcriptional or post-transcriptional level. In some embodiments of the present invention, the cis-acting regulatory element is an activator sequence that enhances or stimulates the activity of a transcriptional control element or the expression of a transcribable sequence. In other embodiments, the cis-acting regulatory element modulates mRNA stability, mRNA processing and export or translation.

By "d1EGFP" is meant a variant of EGFP that is fused to a mutated PEST sequence and consequently has a half-life of only about 1 hour. Similarly, d1ECFP and d1EYFP are also available. A destabilised variant of DsRed could be made in the same way. Henceforth referred to as d1DsRed.

By "d2EGFP" is meant a mutant form of EGFP variants that is fused to a PEST sequence and consequently has a half-life of only 2 hours. Similarly, d2ECFP (cyan) and d2EYFP (yellow) are also available. A destabilised variant of DsRed could possibly be made in the same way. Henceforth referred to as d2DsRed.

By "dEGFP" is meant a general term for all destabilised variants of EGFP (including all colours) formed. (Li et al).

By "derivative" is meant a polynucleotide or polypeptide that has been derived from a reference polynucleotide or polypeptide, respectively, for example by conjugation or complexing with other chemical moieties or by post-transcriptional or post-translational modification techniques as would be understood in the art.

By "DNA" is meant deoxyribonucleic acid.

By "DsRed" is meant the red fluorescent protein isolated from the IndoPacific sea anemone relative *Discosoma* species.

By "ECFP" is meant the mutant form of EGFP with altered excitation/emission spectra that fluoresces cyan coloured light.

By "EGF" is meant epidermal growth factor

By "EGFP" is meant the enhanced green fluorescent protein. A mutant form of GFP with enhanced fluorescence. (Cormack et al).

By "ErbB2" is meant the second member of the epidermal growth factor receptor family. Also known as HER-2.

By "exon" is meant the sequences of a RNA primary transcript that are part of a messenger RNA molecule, or the DNA that encodes such sequences. In the primary transcript neighbouring exons are separated by introns.

By "expression vector" is meant a vector that permits the expression of a polynucleotide inside a cell. Expression of a polynucleotide includes transcriptional and/or post-transcriptional events By "EYFP" is meant a mutant form of EGFP with altered excitation/emission spectra that fluoresces yellow coloured light.

By "firefly luciferase" is meant the enzyme derived from the luc gene of the firefly, which catalyses a reaction using D-luciferin and ATP in the presence of oxygen and $Mg^{++}$ resulting in light emission.

By "flow cytometry" is meant a method, in which live or fixed cell suspensions are applied to a flow cytometer that individually measures an activity or property of a detectable label associated with the cells of the suspension. Labelling of cells can occur, for example, via fluorescent compounds or by antibodies covalently attached to a specific fluorescent compound. Several different excitation/emission wavelengths can be tested simultaneously to measure different types of fluorescence. Sub-populations of cells with desired characteristics (fluorescence, cell size) can be gated such that further statistical analyses apply only to the gated cells. Flow cytometers equipped with a cell sorting option can physically separate cells with the desired fluorescence and retrieve those (live) cells in a tube separate from the remainder of the initial cell population. Also referred to as FACS (fluorescence activated cell sorting).

The term "gene" as used herein refers to any and all discrete coding regions of a host genome, or regions that code for a functional RNA only (e.g., tRNA, rRNA, regulatory RNAs such as ribozymes etc) as well as associated non-coding regions and optionally regulatory regions. In certain embodiments, the term "gene" includes within its scope the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The gene sequences may be cDNA or genomic DNA or a fragment thereof. The gene may be introduced into an appropriate vector for extrachromosomal maintenance or for integration into the host.

By "GFP" is meant a fluorescent protein (Tsien et al), which is isolatable from the jellyfish *Aequoria victoria*, and which can be used as a reporter protein. DNA constructs encoding GFP can be expressed in mammalian cells and cause the cells to fluoresce green light when excited with specific wavelengths. The term "GFP" is used herein to refer to all homologues and analogues, including colour variants and fluorescent proteins derived from organisms other than *Aequoria victoria* (e.g., DSRed and HcRed, Clonetech; hrGFP, Stratagene).

By "half-life" is meant the time taken for half of the activity, amount or number of molecules to be eliminated. Thus, the "mRNA half-life" is the time taken for half of the existing mRNA molecules to decay. mRNA half-life can be measured by blocking transcription (e.g. with Actinomycin D) and measuring the rate of decay of the mRNA in the absence of any new mRNA being formed. Alternatively, the intracellular half-life of a polypeptide refers to the time taken for half of the activity, amount or number of polypeptide molecules in a cell or population of cells to decay. Polypeptide half-life can be measured by blocking translation (e.g. with cyclohexamide) and measuring the rate of decay of the polypeptide (or its functional activity) in the absence of any new polypeptide being formed. However, the use of polypeptide levels or activities as a measure of gene expression at earlier stages such as transcription, suffers from long time delays between the actual effect (altered transcription) and the measurable effect (altered protein levels). A major cause of this delay is the relatively slow decay of both the mRNA and the protein. The effects of this delay include: minor or transient changes in transcription are difficult to detect; kinetic assays are highly inaccurate; and assays require long incubation times. Accordingly, the true measure of the time delay between altered transcription and altered protein levels would be the rate of decay of the polypeptide after a block in transcription, which would incorporate the combined effects of protein stability and mRNA stability. This measurement is referred to herein as the "effective half-life" of a polypeptide.

By "intron" is meant a non-coding sequence within a gene, or its primary transcript, that is removed from the primary transcript and is not present in a corresponding messenger RNA molecule.

By "luciferase" is meant any reporter enzyme that catalyses a reaction, which leads to light emission. Exogenous substrates are added and the reaction is quantified using a luminometer. The substrate requirements for firefly and *Renilla* luciferases are different, allowing the two to be distinguished in the Dual Luciferase Assay (Promega, Madison, Wis., USA).

By "MAPK" is meant a mitogen activated protein kinase. Includes several different kinases involved in intracellular signal transduction pathways that lead to growth or apoptosis (cell death). The term "MAPK" is sometimes used in reference to two specific MAPKs, Erk1 and Erk2 (extracellular regulated kinases 1 and 2).

By "mCMV" is meant a minimal CMV promoter. In some embodiments, a minimal mCMV promoter does not activate transcription on its own but can be linked to a TRE to provide tetracycline (and doxycycline)-dependent transcription or linked to other enhancer elements to provide transcription that is dependent on the activity of that enhancer.

By "MCS" is meant a multiple cloning site, which is a region of a nucleic acid molecule comprising a plurality of sites cleavable by different enzymes or chemicals for inserting polynucleotides into the nucleic acid molecule. Typically, a MCS refers to a region of a DNA vector that contains unique restriction enzyme recognition sites into which a DNA fragment can be inserted. The term "MCS" as used herein, also includes any other site that assists the insertion of DNA fragments into the vector. For example, a T overhang (Promega, Madison, Wis., USA), which allows direct insertion of fragments generated by polymerase chain reaction (PCR).

By "mRNA" is meant messenger RNA, which is a "transcript" produced in a cell using DNA as a template, which itself encodes a protein. mRNA is typically comprised of a 5'-UTR, a protein encoding (i.e., coding) region and a 3'-UTR. mRNA has a limited half-life in cells, which is determined, in part, by stability elements, particularly within the 3'-UTR but also in the 5'-UTR and protein encoding region.

By "MODC" is meant mouse ornithine decarboxylase or a portion, variant or derivative thereof containing a PEST sequence.

By "modulating" is meant increasing or decreasing, either directly or indirectly, the stability or activity of a molecule of interest.

By "operably connected" or "operably linked" and the like is meant a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame. A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein. "Operably connecting" a promoter to a transcribable polynucleotide is meant placing the transcribable polynucleotide (e.g., protein encoding polynucleotide or other transcript) under the regulatory control of a promoter, which then controls the transcription and optionally translation of that polynucleotide. In the construction of heterologous promoter/structural gene combinations, it is generally preferred to position a promoter or variant thereof at a distance from the transcription start site of the transcribable polynucleotide, which is approximately the same as the distance between that promoter and the gene it controls in its natural setting; i.e.: the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e. the genes from which it is derived.

The term "pA" as used herein refers to a polyadenylation site, which is a DNA sequence that serves as the site to cleave and add to the immature mRNA, a polyA tail. Various pA sequences from SV40 virus genes or the β galactosidase gene or other sources, including synthetic polyadenylation sites can be used in expression vectors for this purpose.

The term "PEST" refers to an amino acid sequence that is enriched with the amino acids proline (P), glutamic acid (E), serine (S) and threonine (T). Proteins containing PEST sequences have shortened half-lives.

By "plasmid" is meant a circular DNA vector. Plasmids contain an origin of replication that allows many copies of the plasmid to be produced in a bacterial (or sometimes eukaryotic) cell without integration of the plasmid into the host cell DNA.

By "PMA" is meant phorbol myristoloic acid.

By "polynucleotide" or "nucleic acid" is meant linear sequences of nucleotides, including DNA or RNA, which may be double-stranded or single-stranded.

By "polypeptide," "peptide" or "protein" is meant a polymer of amino acids joined by peptide bonds in a specific sequence.

By "promoter" is meant a region of DNA, generally upstream (5') of a coding region, which controls at least in part the initiation and level of transcription. Reference herein to a "promoter" is to be taken in its broadest context and includes the transcriptional regulatory sequences of a classical genomic gene, including a TATA box and CCAAT box sequences, as well as additional regulatory elements (i.e., activating sequences, enhancers and silencers) that alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Promoters according to the invention may contain additional specific regulatory elements, located more distal to the start site to further enhance expression in a cell, and/or to alter the timing or inducibility of expression of a structural gene to which it is operably connected. The term "promoter" also includes within its scope inducible, repressible and constitutive promoters as well as minimal promoters. Minimal promoters typically refer to minimal expression control elements that are capable of initiating transcription of a selected DNA sequence to which they are operably linked. In some examples, a minimal promoter is not capable of initiating transcription in the absence of additional regulatory elements (e.g., enhancers or other cis-acting regulatory elements) above basal levels. A minimal promoter frequently consists of a TATA box or TATA-like box. Numerous minimal promoter sequences are known in the literature. For example, minimal promoters may be selected from a wide variety of known sequences, including promoter regions from fos, CMV, SV40 and IL-2, among many others. Illustrative examples are provided which use a minimal CMV promoter or a minimal IL2 gene promoter (−72 to +45 with respect to the start site; Siebenlist, 1986).

By "Renilla luciferase" is meant a polypeptide, which is derivable from sea pansy (Renilla reniformis), and which utilizes oxygen and coelenterate luciferin (coelenterazine) to generate light emission.

By "reporter vector" is meant an expression vector containing a "reporter gene" that encodes a polypeptide (or mRNA) that can be easily assayed. Typically, the reporter gene is linked to regulatory sequences, the function or activity of which, is being tested.

By "reporter" is meant a molecule, typically a protein or polypeptide, which is encoded by a reporter gene and measured in a reporter assay. Current systems generally utilize an enzymatic reporter and measure reporter activity.

By "RNA" is meant ribonucleic acid.

By "rtTA" is meant reverse tTA (see below), which binds the TRE and activates transcription only in the presence of tetracycline or doxycycline.

By "SEAP" is meant secreted alkaline phosphatase reporter gene.

By "SKBR3" is meant the human breast cancer cell line that overexpresses ErbB2.

By "stringent conditions" is meant temperature and ionic conditions under which only nucleotide sequences having a high frequency of complementary bases will hybridise. The stringency required is nucleotide sequence dependent and depends upon the various components present during hybridisation and subsequent washes, and the time allowed for these processes. Generally, in order to maximise the hybridisation rate, non-stringent hybridisation conditions are selected; about 20 to 25° C. lower than the thermal melting point ($T_m$). The $T_m$ is the temperature at which 50% of specific target sequence hybridises to a perfectly complementary probe in solution at a defined ionic strength and pH. Generally, in order to require at least about 85% nucleotide complementarity of hybridised sequences, highly stringent washing conditions are selected to be about 5 to 15° C. lower than the $T_m$. In order to require at least about 70% nucleotide complementarity of hybridised sequences, moderately stringent washing conditions are selected to be about 15 to 30° C. lower than the $T_m$. Highly permissive (low stringency) washing conditions may be as low as 50° C. below the $T_m$, allowing a high level of mismatching between hybridised sequences. Those skilled in the art will recognise that other physical and chemical parameters in the hybridisation and wash stages can also be altered to affect the outcome of a detectable hybridisation signal from a specific level of homology between target and probe sequences.

The term "SV40/CMV/RSV" is used herein to refer to promoter elements derived from simian virus, cytomegalovirus and Rous sarcoma virus respectively. Generally, these promoters are thought to be constitutively active in mammalian cells.

By "TetO" is meant the Tet operator DNA sequence derived from the E. coli tetracycline-resistance operon.

By "Tet-Off Cell Lines" is meant cell lines stably expressing tTA such that tetracycline or doxycycline will shut off transcription from TRE promoters.

By "Tet-On Cell Lines" is meant cell lines stably expressing rtTA such that tetracycline or doxycycline will turn on transcription from TRE promoters.

By "transcription" is meant the process of synthesizing a RNA molecule complementary to the DNA template.

By "transfection" is meant the process during which a plasmid or DNA fragment is inserted into a eukaryotic cell. Typically, 2–50% of cells take up the plasmid and express the protein product for ~3 days without incorporating the plasmid DNA into the cell's chromosomes (=transient transfection). A small proportion of these cells will eventually incorporate the plasmid DNA into their genome and permanently express the protein product (=stable transfection).

As used herein the term "transgenic" refers to a genetically modified animal in which the endogenous genome is supplemented or modified by the random or site-directed integration of a foreign gene or sequence.

The "transgenic animals" of the invention are suitably produced by experimental manipulation of the genome of the germline of the animal. These genetically engineered animals may be produced by several methods including the introduction of a "transgene" comprising nucleic acid (usually DNA) into an embryonal target cell or integration into a chromosome of the somatic and/or germ line cells of an animal by way of human intervention. A transgenic animal is an animal whose genome has been altered by the introduction of a transgene.

By "translation" is meant the process whereby a mRNA molecule is used as a template for protein synthesis.

By "TRE" is meant any tetracycline responsive element (Gossen et al), generally combined with a minimal promoter such that transcription occurs only via the binding of exogenous factors (e.g., tTA or rtTA) to the TRE. Preferred embodiments of this invention utilize a TRE comprised of 7 repeats of the tetO sequence linked to a minimal CMV promoter (mCMV) (Clontech Laboratories Inc., Palo Alto, Calif., USA).

By "tTA" is meant tetracycline-controlled transactivator, which is comprised of the Tet repressor protein (TetR) and the VP16 activation domain, such that it binds the TRE and activates transcription, only in the absence of tetracycline or doxycycline.

By "TS" is meant thromboxane synthase promoter.

By "variant" is meant a polynucleotide or polypeptide displaying substantial sequence identity with a reference polynucleotide or polypeptide, respectively. Variant polynucleotides also include polynucleotides that hybridise with a reference sequence under stringent conditions. These terms also encompasses polynucleotides which differ from a reference polynucleotide by the addition, deletion or substitution of at least one nucleotide. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants. With regard to variant polypeptides, it is well understood in the art for example that some amino acids may be changed to others with broadly similar properties without changing the nature of the activity of the polypeptide (conservative substitutions).

By "vector" is meant a vehicle for inserting a foreign DNA sequence into a host cell and/or amplifying the DNA sequence in cells that support replication of the vector. Most commonly a plasmid but can also be a phagemid, bacteriophage, adenovirus or retrovirus.

By "vEGFP," "EGFP I" or "variant of EGFP" is meant different colour variants and/or different half-life variants of EGFP.

By "vGFP" is meant all variants of GFP; including homologues and analogues such as DsRed, also EGFP variants or destabilised GFP variants.

2. Constructs and Methods of the Present Invention

The present invention provides inter alia expression constructs which modulate the stability of transcripts and consequently, the amount or activity of polypeptide produced by the constructs. Although constructs which increase the stability of a transcript are clearly encompassed by the present invention, certain embodiments focus on destabilising transcripts. Here transcript stability can be reduced by the addition of one or more destabilising elements to, or by the removal of one or more stability elements (e.g., a poly A tail) from, a transcribable polynucleotide. Compared to existing expression constructs, the construct of the present invention provides kinetics of protein expression with improved temporal correlation to the promoter activity, e.g., by reducing the time lag between decreased promoter activity and decreased levels of a corresponding expression product or by reducing the steady state level of the expression product such that increased promoter activity results in a larger and/or faster increase in levels of the expression product relative to that present before the increase in promoter activity.

Accordingly, one aspect of the present invention is directed to a construct comprising in operable linkage: a polynucleotide that encodes a polypeptide and a nucleic acid sequence that encodes a RNA element that modulates the stability of a transcript encoded by the polynucleotide.

The term "modulates" in the context of transcript stability refers to increasing or decreasing the stability of a transcript and optimal amounts of modulation depends upon the particular application. Without limiting the present invention to any one particular theory or mode of operation, where the RNA element is a sequence of nucleotides which destabilises the transcript, it is envisaged that the element directly or indirectly targets the transcript for degradation.

As used herein the term "destabilising element" refers to a sequence of amino acids or nucleotides which reduces the half-life of a protein or transcript, respectively, inside a cell. Accordingly, a "RNA destabilising element" comprises a sequence of nucleotides which reduces the intracellular half-life of a RNA transcript and a "protein-destabilising element" comprises a sequence of amino acids which reduces the intracellular half-life of a protein. mRNA destabilising elements improve the temporal correlation between altered promoter activity (or mRNA processing events) and altered cytoplasmic mRNA levels. Protein destabilising elements improve the temporal correlation between altered cytoplasmic mRNA levels and altered reporter levels or activity. The extent of the reduction sought at each level depends upon the particular application. In certain embodiments the combination of RNA destabilisation and protein destabilisation significantly improves the temporal correlation between promoter activity (or mRNA processing) and reporter levels or activity in expression constructs compared to constructs without destabilisation elements or with only one type of destabilising element. In other embodiments, the protein destabilising elements improve the temporal correlation between altered mRNA stability, processing or translation and altered reporter levels or activity. In relation to increasing transcript stability, optimum levels of stability will again depend upon the application.

A "RNA stabilising element" is a sequence of nucleotides which increases the intracellular half-life of a RNA molecule which is suitably, but not exclusively selected from mRNA, heterogenous nuclear RNA (hnRNA), small nuclear RNA (snRNA), small nucleolar RNA (snoRNA), small cytoplasmic RNA (scRNA), ribosomal RNA (rRNA), translational control RNA (tcRNA), transfer RNA (tRNA), eRNA, messenger-RNA-interfering complementary RNA (micRNA) or interference RNA (iRNA) and mitochondrial RNA (mtRNA). In certain embodiments the RNA molecules are mRNA molecules.

In the context of reducing the intracellular half-life of a molecule selected from a RNA transcript or an encoded protein of interest, (a) one or more destabilising elements are typically added and/or (b) one or more stabilising elements are typically removed in order to confer a level of enhanced degradation on the molecule, which thereby reduce(s) the intracellular half-life of the molecule to a half-life that is suitably less than about 24, 10 or 5 hours, desirably less than about 3, 2 or 1 hour(s), or even less than about 30, 15, 10, 5 or 3 minutes. The half-life of a RNA transcript or an encoded protein of interest advantageously corresponds to the lowest half-life that provides a steady-state expression level of at least about 10-fold the minimum detectable level of the transcript or encoded protein.

The intracellular or intracellular-like conditions are typically physiological for the cell type. The temperature of the intracellular or intracellular-like conditions is usually physiological for the cell type. Exemplary temperatures for mammalian cells range generally from about 30° C. to about 42° C., and typically from about 35° C. to about 37° C.

At a minimum, enhanced ribonucleic or proteolytic degradation of a RNA transcript or polypeptide, respectively, refers to a level of ribonucleic or proteolytic degradation that is at least about 5, 10, 20, 40, 50, 60, 70, 80, 90, 100, 150, 200, 400, 600, 1,000, 2,000, 4,000, 6,000, 8,000, 10,000, 12,000% greater than that of the RNA transcript or polypeptide in the absence of the destabilising element(s) or in the presence of a stabilising element(s) as the case may be. Assays for measuring RNA degradation are known to those of skill in the art. For example, RNA degradation can be measured using a range of assays disclosed for example by Ross, J (1995) or by Liu, J et al. (JBC 2000), which are based on the use of transcriptional inhibitors (Actinomycin D, DRB, cordycepin, alpha-amanitin), pulse labelling (radioactive nucleosides), cell-free decay methods (polysomes, cytosol or reticulocytes), or short-term promoter activation (fos promoter, see below). Assays for measuring degradation of proteins are also known to persons of skill in the art. For example, proteolytic degradation may be measured in vitro using a mammalian cell lysate assay including, but not restricted to, the reticulocyte lysate assay of Bachmair et al in U.S. Pat. No. 5,646,017. Alternatively, proteolytic degradation may be measured in vivo using cyclohexamide or pulse-chase protocols as for example disclosed by Vazhappilly, R and Sucher, N (2002) or by Saito, T et al. (1998). In certain embodiments, intracellular half-lives of polypeptides are determined using blockers of translation (e.g., cyclohexamide).

The RNA destabilising elements can be derived from any source and in particular the 3'-UTR or 5'-UTR regions of short-lived mRNAs often contain destabilising sequences. As used herein, the term "derived from" shall be taken to indicate that a particular integer or group of integers has originated from the species specified, but has not necessarily been obtained directly from the specified source. For example, RNA destabilising sequences may be cloned from short-lived RNAs such as but not limited to RNAs from the c-fos, c-jun, c-myc, GM-CSF, IL-3, TNF-alpha, IL-2, IL-6, IL-8, IL-10, Urokinase, bcl-2, SGLT1 (Na(+)-coupled glucose transporter), Cox-2 (cyclooxygenase 2), IL8, PAI-2 (plasminogen activator inhibitor type 2), beta1-adrenergic receptor and GAP43 (5'-UTR and 3'-UTR) genes. Alternatively, RNA destabilising sequences may be selected from AU-rich elements (AREs) and/or U-rich elements (UREs), including but not limited to single, tandem or multiple or overlapping copies of the nonamer UUAUUUA(U/A)(U/A) [SEQ ID NO:2] (where U/A is either an A or a U) (Lagnado et al 1994) and/or the pentamer AUUUA [SEQ ID NO:3] (Xu et al 997) and/or the tetramer AUUU [SEQ ID NO:4] (Zubiaga et al. 1995). The term "tandem copies" allows for both duplication and/or non-duplication of one or more of the outer nucleotides. For example, tandem copies of the pentamer AUUUA [SEQ ID NO:3], includes sequences such as AUUUAUUUAUUUA [SEQ ID NO:5] as well as AUUUAAUUUAAUUUA [SEQ ID NO:6]. RNA destabilising elements have also been described for example from phosphoenolpyruvate carboxy kinase mRNA (PEPCK), the *Drosophila* Bicoid gene, the human thioredoxin gene, heat stable antigen gene and soybean 10A5 gene.

Iron responsive elements and iron regulatory protein binding sites may also be advantageously incorporated into the instant constructs to modulate RNA stability or translational efficiency experimentally or in response to stimuli. Histone RNAs, particularly their 3'-UTRs, are especially useful for modulating RNA stability in a cell-cycle dependent fashion.

Also contemplated are modifications to or permutations of the elements listed above. Accordingly, biologically active fragments as well as variants and derivatives of the destabilising elements referred to above are encompassed by the present invention. For example, RNA destabilising elements may be identified and/or modifications made thereto using a computational approach and database analysis (Dandekar T et al).

In a related embodiment the present invention contemplates a construct comprising in operable linkage: a polynucleotide which encodes a polypeptide and a nucleic acid sequence which encodes a stabilising RNA element that enhances the stability of a transcript encoded by polynucleotide. In illustrative examples the nucleic acid sequence is, or is derived from, a gene selected from alpha2 globin, alpha1 globin, beta globin, or growth hormone, which are examples of long-lived mRNAs. As used herein, underscoring or italicising the name of a gene shall indicate the gene, in contrast to its protein product, which is indicated by the name of the gene in the absence of any underscoring or italicising. For example, "alpha2 globin" shall mean the alpha2 globin gene, whereas "alpha2 globin" shall indicate the protein product of the "alpha2 globin" gene.

The ability to destabilise a transcript and to reduce the amount of protein produced by a cell will clearly be useful for a wide range of applications, including methods for assaying the activity of gene expression-modulating elements (e.g., transcriptional control elements and cis-acting regulatory elements) or for identifying elements of this type or agents that modulate their activity. Thus, another aspect of the present invention contemplates a construct comprising in operable linkage a polynucleotide which encodes a polypeptide and a nucleic acid sequence which encodes a RNA destabilising element that reduces the stability of a transcript encoded by the polynucleotide. In illustrative examples, the nucleic acid sequence is, or is derived from, a gene selected from c-fos, c-jun, c-myc, GM-CSF, IL-3, TNF-alpha, IL-2, IL-6, IL-8, IL-10, Urokinase, bcl-2, SGLT1 (Na(+)-coupled glucose transporter), Cox-2 (cyclooxygenase 2), IL-8, PAI-2 (plasminogen activator inhibitor type 2), beta1-adrenergic receptor or GAP43. In certain embodiments, the nucleic acid sequence is selected from any one of SEQ ID NOS 1 to 23, especially from SEQ ID NO: 1, 13, 19 or 49, or biologically active fragments thereof, or variants or derivatives of these.

In certain embodiments, the nucleic acid sequence encoding the RNA destabilising element is linked to a sequence encoding a protein of interest, which in turn is linked to a promoter of interest that is optionally modulatable (i.e., inducible or repressible) such that expression is turned on and then turned off. In this application, the RNA destabilising elements typically serve to shorten the period of expression of a functional mRNA or protein. This may be applied in vitro or in vivo. For example, a cell cycle-specific promoter could be combined with the RNA destabilising elements to express a protein of interest, exclusively in certain stages of the cell cycle. The protein of interest may be a functional protein or a reporter protein. In the latter example, reporter levels can be used as an indicator of cell-cycle stage or cell proliferation. Similarly, the reporter levels may be used to give a measure of other cellular events relating to the activity of the promoter of interest. Such events include, but are not limited to, apoptosis, immune function, modulation of a signal transduction pathway, modulation of a regulatory pathway, modulation of a biosynthetic pathway, toxic response and cell differentiation. In certain embodiments in which the activity of a cis-acting regulatory element (e.g., an enhancer or post-transcriptional control element) is of interest, the reporter levels may also give a measure of cellular events (as discussed for the promoter of interest) relating to the activity of that cis-acting regulatory element. By extension, reporter levels may be used as an indirect measure of action of a compound or treatment on a cellular event.

One particular application is in the area of determining gene expression. Specifically, by reducing the time lag between altered transcription and altered levels of the resultant polypeptide in a cell, it is possible to more accurately determine promoter or enhancer activity. In this application a reporter gene, whose expression is modulated by regulatory elements within the construct, is used to determine promoter or enhancer activity. Thus, another aspect of the present invention contemplates a construct comprising in operable linkage: a polynucleotide which encodes a reporter polypeptide and a nucleic acid sequence which encodes a RNA destabilising element that reduces the stability of a transcript encoded by the polynucleotide.

In some embodiments the RNA destabilising sequences are incorporated into the region encoding the 3'-UTR of the reporter mRNA. Alternatively or in addition, destabilising elements are incorporated into the 5'-UTR and/or protein coding region, which is suitably not essential to, or does not interfere with, the selected activity of the encoded protein.

In a related embodiment the RNA destabilising sequences are used to alter the kinetics of expression of a polypeptide from a gene of interest when for example there is a need to accurately monitor, limit or reduce its expression. Typically for this application, RNA destabilising elements are used in conjunction with protein-destabilising elements.

The constructs of the present invention have applications in a variety of gene expression systems where it is desirable to have a brief period of mRNA or protein expression or to minimise the time lag between changes in promoter activity and the resultant changes in mRNA/protein levels.

In certain embodiments, the constructs are designed for use in eukaryotic cell systems. It should be noted however that the RNA destabilising elements may be used in a wide range of eukaryotic (e.g., mammals and plants) systems including cells, tissues or whole organisms defined as yeast, insect, nematode, fish, bird or mammal. For use in plants, different promoters and possibly different reporters and RNA destabilising elements (e.g., DST sequences) may be used.

In some embodiments, the polynucleotide whose transcript is stabilised or destabilised by the RNA element encodes a reporter molecule or a destabilised variant thereof. Reporter molecules are well known in the art. Suitably, the reporter molecules are reporter proteins illustrative examples of which include, but are not limited to, Luciferase, Green Fluorescent Protein, Red Fluorescent Protein, SEAP, CAT, or biologically active fragments thereof, or variants or derivatives of these.

In other embodiments, the polynucleotide whose transcript is stabilised or destabilised by the RNA element encodes a protein having at least a light-emitting activity and a selection marker activity. Suitably, the polynucleotide comprises a chimeric gene, which includes a coding sequence from a gene encoding a light-emitting protein and a coding sequence from a gene encoding a selectable marker protein. Illustrative examples of light-emitting proteins include fluorescent proteins (e.g., Green Fluorescent Protein, Red Fluorescent Protein and their variants and derivatives) and luminescent proteins (e.g., Luciferases such as *Renilla* luciferase and *Photinus* Luciferase and their variants and derivatives). Illustrative examples of selectable marker proteins are positive selectable marker proteins including, but not limited to, proteins encoded by antibiotic resistance genes (e.g., hygromycin resistance genes, neomycin resistance genes, tetracycline resistance genes, ampicillin resistance genes, kanamycin resistance genes, phleomycin resistance genes, bleomycin resistance genes, geneticin resistance genes, carbenicillin resistance genes, chloramphenicol resistance genes, puromycin resistance genes, blasticidin-5-deaminase genes), heavy metal resistance genes, hisD genes, hypoxanthine phosphoribosyl transferase (HPRT) genes and guanine phosphoribosyl transferase (Gpt) genes. In certain embodiments, the light-emitting protein is selected from Green Fluorescent Protein, Luciferase or biologically active fragments thereof, or variants or derivatives of these and the selectable marker protein is selected from kanamycin kinase, neomycin phosphotransferase, aminoglycoside phosphotransferase, puromycin N-acetyl transferase, puromycin resistance protein or biologically active fragments thereof, or variants or derivatives. Chimeric genes of this type can be constructed using standard recombinant or synthetic techniques, as described for example in U.S. Patent Application Publication No. 2002/0150912 and in European Patent Application No. 1 262 553.

Another aspect of the present invention contemplates the combination of a protein-destabilising element (e.g., a DNA/RNA sequence encoding an intracellular protein degradation signal or degron which may be selected from a destabilising amino acid at the amino-terminus of a polypeptide of interest, a PEST region or a ubiquitin) and a RNA destabilising element (e.g., multiple copies of the nonamer UUAUUUAUU [SEQ ID NO: 1]), such that both RNA and protein are destabilised. For example, one such embodiment incorporates into a construct a PEST sequence immediately upstream of the translation stop codon and 4 nonamers located downstream of the stop codon (suitably 20 nt or more from stop codon). In this way, reporter protein may be destabilised both at the protein level and the RNA (especially mRNA) level.

The destabilised reporter protein may be any suitable protein. For example, destabilised GFP proteins are suitable, such as for example d1EGFP, d1EYFP and d1ECFP comprising the d1 mutant of MODC. The destabilised luciferase protein has been described by Leclerc G. et al. The MODC from d1EGFP is also contemplated.

Any method of destabilising a polypeptide of interest is contemplated by the present invention. For example, a polypeptide of interest can be modified to include a destabilising amino acid at its amino-terminus so that the protein so modified is subject to the N-end rule pathway as disclosed, for example, by Bachmair et al in U.S. Pat. No. 5,093,242 and by Varshavsky et al. in U.S. Pat. No. 5,122,463. In some embodiments, the destabilising amino acid is selected from isoleucine and glutamic acid, especially from histidine tyrosine and glutamine, and more especially from aspartic acid, asparagine, phenylalanine, leucine, tryptophan and lysine. In certain embodiments, the destabilising amino acid is arginine. In some proteins, the amino-terminal end is obscured as a result of the protein's conformation (i.e., its tertiary or quaternary structure). In these cases, more extensive alteration of the amino-terminus may be necessary to make the protein subject to the N-end rule pathway. For example, where simple addition or replacement of the single amino-terminal residue is insufficient because of an inaccessible amino-terminus, several amino acids (including lysine, the site of ubiquitin joining to substrate proteins) may be added to the original amino-terminus to increase the accessibility and/or segmental mobility of the engineered amino terminus.

Modification or design of the amino-terminus of a protein can be accomplished at the genetic level. Conventional techniques of site-directed mutagenesis for addition or substitution of appropriate codons to the 5' end of an isolated or synthesised antigen-encoding polynucleotide can be employed to provide a desired amino-terminal structure for the encoded protein. For example, so that the protein expressed has the desired amino acid at its amino-terminus the appropriate codon for a destabilising amino acid can be inserted or built into the amino-terminus of the protein-encoding sequence. Where necessary, a nucleic acid sequence encoding the amino-terminal region of a protein can be modified to introduce a lysine residue in an appropriate context. This can be achieved most conveniently by employing DNA constructs encoding "universal destabilising segments". A universal destabilising segment comprises a nucleic acid construct which encodes a polypeptide structure, preferably segmentally mobile, containing one or more lysine residues, the codons for lysine residues being positioned within the construct such that when the construct is inserted into the coding sequence of the protein-encoding polynucleotide, the lysine residues are sufficiently spatially proximate to the amino-terminus of the encoded protein to serve as the second determinant of the complete amino-terminal degradation signal. The insertion of such constructs into the 5' portion of a protein-encoding polynucleotide would provide the encoded protein with a lysine residue (or residues) in an appropriate context for destabilisation.

In other embodiments, the polypeptide of interest is modified to contain a PEST region, which is rich in an amino acid selected from proline, glutamic acid, serine and threonine, which region is optionally flanked by amino acids comprising electropositive side chains. In this regard, it is known that amino acid sequences of proteins with intracellular half-lives less than about 2 hours contain one or more regions rich in proline (P), glutamic acid (E), serine (S), and threonine (T) as for example shown by Rogers et al. (1986, *Science* 234 (4774): 364–368).

In still other embodiments, the polypeptide of interest is conjugated to a ubiquitin or a biologically active fragment thereof, to produce a modified polypeptide whose rate of intracellular proteolytic degradation is increased, enhanced or otherwise elevated relative to the unmodified polypeptide.

The constructs of the present invention, which contain RNA and/or protein-destabilising sequences, are particular useful for assaying the activity of gene expression-modulating elements (GEMEs) including, but not limited to, transcriptional control elements and cis-acting regulatory elements. These assays provide a more 'real-time' analysis of GEME activity than provided by existing assays and typically comprise: (1) expressing at least in part from a GEME of interest a reporter polynucleotide operably linked to a RNA destabilising element in a test construct and (2) measuring the level or functional activity of the reporter polypeptide produced from the test construct. Generally, control assays are also performed using a control construct comprising a GEME that is different than the GEME of interest. In these embodiments, it is desirable that the reporter polypeptide produced from the test construct is detectably distinguishable from the reporter polypeptide produced from the control construct. The test construct and the control construct may be in the form of separate constructs or a single chimeric construct. They may also be contained within a single cell or within different cells.

The constructs of the present invention are also useful in screening for drugs or treatments that alter the activity of gene expression-modulating elements including transcriptional control elements (e.g., promoters) and cis-acting regulatory elements (e.g., enhancers). Compared to existing constructs, a near "real-time" measurement of drug action can be obtained. Accordingly, yet another aspect of the present invention contemplates methods for identifying an agent that modulates the activity of a GEME of interest. These methods generally comprise expressing at least partly under the control of the GEME of interest in a test construct a reporter polynucleotide operably linked to a RNA stability modulating element in the presence and absence of a test agent. The level or functional activity of the reporter polypeptide in the presence and absence of the test agent is then measured and compared. A difference between the level or functional activity of the reporter polypeptide in the presence and absence of the test agent indicates that the test agent modulates the activity of the GEME of interest. Generally, control constructs are also used in these assays, which comprise a GEME that is different than the GEME of interest. In these embodiments, the reporter polypeptide produced from the test construct is suitably detectably distinguishable from the reporter polypeptide produced from the control construct. The test construct and the control construct may be in the form of separate constructs or a single chimeric construct. They may also be contained within a single cell or within different cells. In some of these embodiments, the test construct may be contained within a first cell type or exposed to a first condition and within a second cell type or exposed to a second condition, wherein a difference in the level or functional activity of the polypeptide in the presence of the test agent between the cell types or conditions provides information on the effect of the test agent on those cell types or conditions (e.g., mode of action or specificity).

In some embodiments, the constructs of the present invention comprise one or more elements in any order selected from the group consisting of:
  (i) a multiple cloning site for introducing a sequence of nucleotides, which site is suitably cleavable enzymatically or otherwise biochemically to provide a linearised vector into which PCR amplification products are clonable directly (e.g., an Ec1HK1 site);
  (ii) a reporter gene;
  (iii) a promoter and/or enhancer for regulating expression of a transcribable polynucleotide (e.g., the polynucleotide that encodes the polypeptide);
  (iv) a polyadenylation sequence;
  (v) a selectable marker gene; and
  (vi) an origin of replication.

In certain embodiments, the constructs of the present invention are in the form of vectors or sets of vectors, particularly but not exclusively plasmids, with applications in the study or measurement or monitoring of gene expression (e.g., promoter or enhancer activity). The vectors are suitably in the form of prokaryotic or eukaryotic vectors. Many other vectors could also be used such as for example viruses, artificial chromosomes and other non-plasmid vectors.

In some embodiments, pairs or sets of plasmids are provided, each containing one or more of the RNA destabilising sequences described above in operable linkage with a polynucleotide encoding a destabilised reporter protein such as, for example, d1EGFP, d1EYFP, d1ECFP or d1HcRed. One plasmid (the control) from each pair or set contains a promoter 5' of the reporter encoding region. The promoter comprises one or more elements which are modulatable (i.e., inducible or repressible) by exogenous treatments (e.g., the TRE combined with a minimal promoter such as mCMV; see FIG. 2c). Alternatively, a constitutively active promoter such as TS, SV40, CMV, TK or RSV is used (see FIG. 2b). In plant systems the Top-ten promoter could replace TRE, and the 35S promoter of cauliflower mosaic virus can replace SV40 etc. *Agrobacterium tumefaciens* can be used in plants to facilitate gene transfer. The other plasmid(s) in the pair or set are identical to the control plasmid, except that a cloning site (MCS) replaces the promoter, and the reporter encoding region encodes a reporter similar to but distinguishable from the control reporter (see FIG. 2a). In some embodiments, the control plasmid encodes a destabilised variant of EGFP (e.g., d1EGFP, d1EYFP or d1ECFP) and the other vectors (test vectors) each encode a different colour variant from the same list or d1HcRed or other destabilised fluorescent protein (same protein half-life). In other embodiments, a control and one of the test reporters are incorporated into a single vector, such as for example a bi-directional plasmid (see FIG. 3).

In the above embodiments, both control and test plasmids encode a destabilised mRNA, which in turn encodes a destabilised protein. Thus the time lag between decreased promoter activity and decreased reporter protein levels is significantly reduced compared to the time lag with existing constructs. Similarly, increased promoter activity is more readily and quickly detectable due to the reduced levels of pre-existing mRNA and protein. Other differences between the control and test constructs, which can lead to errors, are minimised by using fluorescent proteins that differ from each other by only a few small mutations. Compared to luciferase or other enzyme based assays, the fluorescent reporters described here, offer several other advantages including:

Several different reporters can be measured in the same cells/samples.

Live cells can be measured, allowing multiple time points of the same samples or further manipulation post-measurement e.g., measurement of the same cells before and after treatment with a drug.

Successfully transfected cells can be visualised by fluorescent microscopy. Therefore poor transfections can be identified simply by looking at the cells under a microscope, without further investment of resources.

No substrates are required, therefore the method is less technically demanding, faster, less expensive and more accurate.

Both control and test reporter expression can be measured simultaneously by flow cytometry (see advantages of flow cytometry below).

Embodiments utilising TREs as the control promoter can only be used in Tet-On or Tet-Off cell lines, but as compared to other control promoters, exhibit less interference from or to the test promoter and are less affected by various stimuli used to examine inducibility of the test promoter. Thus, they provide a more accurate measurement of transfection efficiency and relative test promoter activity. Control reporter expression can be switched on or off as required and used to confirm the lack of promoter cross-talk or compensate for it if present.

In other embodiments, the control and one of the test reporters described above are both incorporated into a single vector, preferably a bi-directional plasmid. Interference between the two promoters, which is a major drawback of previous dual promoter vectors, is minimised by using TREs in the control promoter and/or insulator DNA (U.S. Pat. No. 5,610,053). Such a single vector system reduces the inaccuracies of co-transfection studies.

The invention also provides constructs in which informative promoters or enhancers or their fragments are placed upstream of a reporter polynucleotide. Informative promoters include, but are not restricted to, cell cycle-dependent promoters (e.g., cyclin A, B, or D1, histone or topoisomerase I promoters), promoters activated by apoptotic (cell death) pathways and promoters/fragments linked to mitogenic signals (Table 1). Examples of informative enhancers that can be used include any of those used in Clontech's Mercury Pathway Profiling Systems. Clontech's Mercury In Vivo Kinase Assay Kits represent another example of how the present invention can be used. In this example the promoter element is a TRE that is combined in cells with a chimeric TetR-transactivator protein that permits transcription from the TRE only when a specific kinase is active and can phosphorylate the transactivator domain of the fusion protein. Thus, the present invention can be used to provide a more real-time measurement of specific kinase activity.

Even still another aspect of the present invention contemplates a cell transfected or transduced with a construct or vector as described herein.

In some embodiments, the constructs or construct-containing cells are introduced into an organism to allow measurement of reporter activity in vivo. Methods for introducing foreign nucleic acid into the nucleome of an organism or for introducing cells into an organism are known to those of skill in the art. In some embodiments of this type, destabilised luciferase rather than destabilised EGFP variants may be the preferred reporter. For example, transgenic mice expressing destabilised luciferase under the control of an informative promoter, can be used to measure the activity of that promoter in the tissues of a live mouse, using a photon camera (photon camera analysis is described by Contag, et al, 1997). The RNA destabilising sequences serve to improve the temporal correlation between promoter activity and reporter levels, thus providing a significant improvement to applications such as drug screening, which benefit from a near real-time measurement of promoter activity.

In some applications it is desirable to express, either in vitro in cell-based systems or in vivo in mammalian systems, both a reporter molecule and a functional gene product. This may involve two separate mRNAs, each containing a mRNA destabilising element. Alternatively, mRNA destabilising elements may be incorporated into a single destabilised transcript that gives rise to two separate proteins (e.g., using an internal ribosome entry site; IRES) or a fusion protein comprised of the reporter and the functional gene product.

The invention also provides cell lines stably expressing the constructs of the invention (with or without a control). Such cells have applications in areas such as drug screening. For example, cells containing a MAPK-dependent reporter vector provide a rapid and inexpensive method for testing the efficacy of drugs designed to inhibit MAPK or any pathway upstream of MAPK-dependent transcription in those cells. In SKBR3 human breast cancer cells, for example, MAPK activity is dependent on signalling from the overexpressed ErbB2 protein. Therefore, drugs that inhibit ErbB2, would cause a decrease in the fluorescence of SKBR3 cells containing such a construct but not in cells lacking ErbB2. Alternatively, cells could be tested ±drug and ±a specific ligand or treatment that leads to MAPK activation via a different pathway, in order to monitor inhibition of that pathway. Cell lines (or organisms) stably expressing a vector linked to a cell-cycle-regulated promoter can be used as very fast, simple and inexpensive means for measuring cell-cycle progression or cell proliferation. Such cell lines have obvious utility in drug screening and are contemplated in the present invention. Examples of cell-cycle regulated promoters are readily available, for example, (Lee, H et al. 1995), (Stein, J et al. 1996) and (Huet, X et al. 1996).

Other embodiments of the present invention are directed to constructs for the study of post-transcriptional regulation, particularly mRNA stability. These constructs typically comprise a reporter polynucleotide operably linked to a transcriptional control element. In illustrative examples of these constructs, the reporter polynucleotide encodes a destabilised reporter protein, such as but not limited to a destabilised variant of EGFP (e.g., d1EGFP, d1EYFP, d1ECFP), with a different colour variant in each separate vector. The TRE (linked to a minimal promoter such as mCMV) is 5' of the reporter encoding region and drives transcription in a tetracycline (or doxycycline) dependent fashion. Other inducible promoter systems can also be used.

Typically the constructs for studying post-transcriptional regulation comprise sites for inserting known or suspected post-transcriptional control elements. In some embodiments, the RNA destabilising elements described above are not included and in their place, MCSs are located, primarily in the 3'-UTR (see FIG. 4a) but also in the 5'-UTR and/or coding region. In some embodiments, sequences thought to affect mRNA stability can be tested by cloning them into the appropriate cloning site of a construct containing one colour variant and measuring the rate of decrease in reporter levels after blocking transcription with tetracycline or doxycycline (see FIG. 7). If desired, the rate of decay can be compared between the "test construct" and the "control construct," (which suitably encodes a different colour reporter protein and does not contain the sequence being tested) in the same cells. The MCS may usefully comprise or work in conjunction with restriction endonuclease sites which allow direct cloning of PCR products having overhangs (see below).

In related embodiments, the invention provides methods for assaying the activity of a post-transcriptional control element or for identifying a post-transcriptional control element or for identifying an agent that modulates elements of this type. These methods generally comprise: (1) expressing from a transcriptional control element in a test construct a reporter polynucleotide that is operably linked to a nucleic acid sequence that encodes, or is suspected to encode, a post-transcriptional control element; and (2) measuring the level or functional activity of the reporter polypeptide produced from the test construct. Often these methods will include the use of control constructs, which do not comprise the nucleic acid sequence that encodes, or is suspected to encode, the post-transcriptional control element. The control constructs may comprise the same or different transcriptional control element as the test construct. In these embodiments, the reporter polypeptide produced from the test construct is suitably detectably distinguishable from the reporter polypeptide produced from the control construct. The test construct and the control construct may be in the form of separate constructs or a single chimeric construct. They may also be contained within a single cell or within different cells. In some embodiments, the transcriptional control element is modulatable, including inducible or repressible promoters. In these embodiments, the methods desirably further comprise (1) inducing or repressing the transcriptional control element of the test construct, and optionally of the control construct; and (2) measuring changes in the level or functional activity of the reporter polypeptide produced from the test construct, and optionally from the test construct, over time.

In certain embodiments, which are directed to identifying agents that modulate a post-transcriptional control element of interest, the expression of the reporter polynucleotide is carried out in the presence and absence of a test agent and the levels or functional activities of the reporter polypeptide produced in the presence and absence of the test agent are compared. A difference between the level or functional activity of the reporter polypeptide in the presence and absence of the test agent indicates that the test agent modulates the activity of the post-transcriptional control element. In some of these embodiments, the test construct may be contained within a first cell type or exposed to a first condition and within a second cell type or exposed to a second condition, wherein a difference in the level or functional activity of the polypeptide in the presence of the test agent between the cell types or conditions provides information on the effect of the test agent on those cell types or conditions (e.g., mode of action or specificity).

In other related embodiments, one or more RNA destabilising element(s) are included to assist scientists specifically searching for RNA stabilising elements. RNA stabilising elements are useful for increasing levels of expressed protein for example during protein purification where high levels or protein are required or when a promoter is weak. Similarly, other embodiments include RNA stabilising element(s) to assist scientists specifically searching for RNA destabilising elements.

In still other embodiments, the control and one of the test reporters are both incorporated into a single vector, desirably a bi-directional plasmid (see FIG. 4b). Interference between the two promoters and moreover, transcription effects of the element or various stimuli tested, is circumvented by using a TRE or similar element to drive both reporters and by measuring reporter levels after addition of doxycycline (or tetracycline), which shuts off transcription from the vector.

A related aspect of the present invention extends to a genetically modified non-human organism comprising a construct as broadly described above. Accordingly, the present invention is directed towards genetically modified animals that contain one or more constructs of the invention in their nucleomes, and especially in their genomes. The genetic modification is generally in the form of a transgene and thus the genetically modified animal of the present invention is a transgenic animal that comprises at least one transgene in its cells, which includes a construct as broadly described above. The transgene is suitably contained within somatic cells of the animal, although it may also be contained within its germ cells. Usually, the transgenic animal is a mammal, which is suitably selected from the order Rodentia. In some embodiments, the transgenic mammal is a mouse, although rats are also of particular utility. However, it will be understood that the present invention is not restricted to these species. For example, the transgenic animal may be a goat, cow, sheep, dog, guinea pig or chicken.

The genetically modified animals of the present invention may be prepared by any number of means. In one method, a nucleic acid targeting construct or vector is prepared comprising two regions flanking the transgene wherein the regions are sufficiently homologous with portions of the genome of an animal to undergo homologous recombination with those portions. Alternatively, constructs for random integration need not include regions of homology to mediate recombination. Conveniently, markers for positive and negative selection are included in the constructs to permit selection of recombinant host cells. The targeting DNA construct is generally introduced into an embryonic stem (ES) cell or ES cell line. Methods for generating cells having gene modifications through homologous recombination are known in the art.

In order that the invention may be readily understood and put into practical effect, particular preferred embodiments will now be described by way of the following non-limiting example.

EXAMPLES

Example 1

Cloning DNA Elements into Vectors

Cloning is carried out according to existing methods, using restriction enzyme sites in the MCS or direct ligation of PCR products in the case of vectors with a "T overhang" in the MCS. With respect to post-transcriptional reporter vectors, however, the inclusion of a MCS in the 3'-UTR or other regions is a significant improvement over current vectors, which were designed for transcriptional or other studies and do not contain convenient cloning sites in these locations.

Example 2

Transfection

Co-transfection of control and test vectors is performed as per existing methods (e.g., Fugene [Boehringer Mannheim, Mannheim, Germany] or electroporation), except in the case of the single (e.g., bi-directional) vector systems described above, which require only one vector and thus eliminate inaccuracies associated with co-transfection

Example 3

Measurement of Reporter Expression

An immediate advantage of the vGFP system is that reporter expression can be visualized directly in living cells, simply by viewing the tissue culture plate or flask under a fluorescent microscope. Therefore, poor transfections can be identified and discarded before any additional time is wasted. Quantitative measurement can be performed using a fluorometer (e.g., 96 well plate format) and since live cells can be measured, the same samples can be measured repeatedly e.g., in a time course.

A further advantage compared to luciferase and other enzyme based assays is that flow cytometry can also be used to measure reporter levels.

Example 4

Advantages of Using Flow Cytometry to Measure Reporter Levels (i) Two or more reporters (control and test) as well as additional parameters, can be measured individually in every cell at a rate of >2,000 cells per second. Therefore, in this application, the method yields thousands to hundreds of thousands of data points per sample versus one datum point for existing luciferase assays.

(ii) Accurate measurement of transfection efficiency: This is useful for optimising transfection protocols. In addition to allowing comparison of different methods, it is also possible to measure both expression per cell and the proportion of cells expressing. This helps the investigator to determine the cause of any problems.

(iii) Identification of co-transfection errors: Co-transfection studies are based on the premise that cells will take up and express an amount of control reporter, which is proportional to the amount of test plasmid taken up by the same cells. This is not always the case. By using the flow cytometry method described here, it is possible to correlate test versus control expression levels in different cells of the same sample. Invalid samples can be identified by the lack of a good linear relationship between test and control reporter levels. Such errors go unnoticed in current methods.

(iv) Simultaneous measurement of additional parameters: Fluorescent labelled antibodies can be used to quantify specific proteins on a cell by cell basis and this can be correlated with reporter levels to determine whether that protein affects gene expression via the element cloned into the reporter construct. Alternatively, the protein of interest can be expressed as a vGFP-fusion protein (the protein of interest fused to a GFP variant) via transfection of an appropriate expression vector (inducible or non-inducible). Levels of the specific protein can then be correlated with the expression of a different GFP variant linked to a regulatory element of interest (co-transfected or transfected at a different time). In a third application, the vGFP reporter is linked to regulatory elements (e.g., promoters) thought to be cell cycle specific. Transfected cells are stained with a fluorescent DNA dye such as propidium iodide to measure DNA content, which is then correlated with reporter expression. In principle, several of the DNA constructs described herein, each containing a different vGFP, could be co-expressed and independently measured. Furthermore, other fluorescent markers could be used in conjunction with these vectors (singly or in multiples).

(v) Cell Sorting: Using a cell sorter, it is possible to isolate viable vGFP expressing cells from the non-expressors. This technique can be used to select stably expressing cells or to remove non-expressors prior to assay initiation. Similarly, it is possible to remove cells expressing very low and/or very high levels of vGFP. This can be used to generate a more homogeneous population and/or to remove cells expressing levels so high that they may not be physiological relevant or may perturb normal cellular function and/or may otherwise adversely affect the data obtained from the DNA vectors described herein.

It is important to note that transient and stable transfections of expression vectors result in a cell population with very heterogeneous levels of expression. In general a thousand fold difference between the highest and lowest expressor is not unusual. The present invention not only offers a method for selecting homogeneous populations when required (see v above), but can also utilise heterogeneity to the benefit of the scientist. For example, identifying co-transfection errors. Another example of this relates to (iv) above. To determine whether protein X affects transcription from promoter Y, then cells are transfected with a reporter construct expressing d1EGFP under the control of promoter Y. If required, cell sorting can be used to isolate cells transiently or stably expressing appropriate levels of d1EGFP. These cells are in turn transiently transfected with a vector expressing a protein X-EYFP fusion protein. During flow cytometry, EGFP is plotted on one axis and EYFP on the other. A positive correlation would indicate that protein X increases transcription from promoter Y and a negative correlation would indicate that protein X inhibits transcription from promoter Y.

Currently, scientists attempting to establish such a correlation would select several different clones of high versus low expressors of protein X. Each clone would then be separately transfected with a promoter Y-luciferase construct and the luciferase activities measured. The use of cell clones requires months of preparation and introduces many variables including pre-existing heterogeneity amongst the host cells and variable sites of vector integration (vector DNA may interfere with a specific gene at the integration site and this site is different for every clone). Furthermore, such a method yields very few data points, with each datum point obtained from a different transfection of a different clone. Thus, the new system is not only more versatile but is quicker and more accurate than existing methods.

Example 5

Laser Scanning Cytometry (LSC)

Unlike flow cytometry, LSC measures multi-colour fluorescence and light scatter of cells on slides, and records the position and time of measurement for each cell analysed. This technique provides data equivalent to flow cytometry but has the advantage of being microscope slide based (Darzynkiewicz et al., 1999; Kamentsky et al., 1997). Owing to the fluorescence of GFP and its variants, the techniques described for flow cytometry are also applicable to LSC.

Example 6

Specific Methods for Post-Transcriptional Assays

These are best summarised by using the example of a study aimed at determining whether a specific 3'-UTR fragment affects mRNA stability. Although this example is one of transient expression, stable transfection could also be used.
(i) The 3'-UTR fragment is ligated into the 3'-UTR cloning site of the test vector and co-transfected with the control vector into a Tet-Off cell line. In the case of the bi-directional vector, no control vector is required. Indeed, the typical application does not require a control reporter or vector since rate of decay can be measured in samples from within the same transfection. 5'-UTR fragments can be tested by inserting them into vectors with a 5'-UTR cloning site.
(ii) The cells are grown in the absence of doxycycline (or tetracycline) for 6–48 h to allow expression of both vectors. Alternatively, cells are grown with low doses of doxycycline (or tetracycline), for 6–48 h to block transcription and then switched to medium without doxycycline (or tetracycline) for 2–12 h to provide a brief burst of transcription.
(iii) High doses of doxycycline (or tetracycline) are then applied to shut off transcription from both vectors.
(iv) The fluorescence of both reporters is measured (by flow cytometry, fluorometry or LSC) in a time course following addition of doxycycline (or tetracycline).

If the cloned element confers mRNA instability, a more rapid decrease in "test" fluorescence will be seen compared to "control" fluorescence of the same cells or sample. Similar studies can be used to test a mRNA element's response to certain stimuli or its effect in different cells or cells expressing different amounts of a specific protein, such as a RNA-binding protein. Applying the stimulus after doxycycline will determine whether pre-existing transcripts are affected by the stimulus. Inserting the element in different locations (e.g., 5'-UTR, 3'-UTR) will determine whether its function is dependent on position. Inserting a protein/polypeptide coding sequence (in frame) within the reporter-coding region of the vector, can be used to determine the effect of that sequence on mRNA and protein stability.

RNA can be extracted from transfected cells and used to measure reporter mRNA directly.

Example 7

Transcription Reporter Vectors

The vectors are plasmids suitable for expansion in *E. coli* and expression of a fluorescent reporter in eukaryotic cells. The plasmids may be used in sets. Each set is comprised of one or more "control" vectors and one or more "test" vectors. Every vector within a set expresses a similarly destabilised mRNA and a similarly destabilised fluorescent reporter protein. In addition to the standard features of such plasmids (ampicillin resistance, origin of replication etc.), each plasmid contains the following construct (see also FIGS. 2 and 3):
  5'—MCS/promoter—transcription start site—5'-UTR—ATG—vEGFP encoding region—stop codon—3'-UTR with mRNA destabilising element—polyadenylation signal
  Where:
  MCS/promoter denotes either a multiple cloning site (test vectors; see FIG. 2*a*) or a constitutively active promoter such as SV40 (control vectors; see FIG. 2*b*) or an inducible promoter such as TRE-mCMV (control vector; see FIG. 2*c*).
  ATG denotes a translation start codon.
  Stop codon denotes a translation stop codon.
  5'-UTR denotes a 5' untranslated region.
  3'-UTR with mRNA destabilising element denotes a 3' untranslated region containing one or more of the mRNA destabilising elements outlined.
  vEGFP denotes a destabilised variant of EGFP. One set of plasmids is provided for each type of destabilising modification (e.g., 1 hr half-life, 2 hr half-life). Within each set of plasmids, one vector is provided for each different colour variant. For example, one set contains vectors expressing d1EGFP, d1EYFP, d1ECFP whereas another set expresses the d2 variants.

In other examples, the control and one of the test reporters described above are both incorporated into a single vector, preferably a bi-directional plasmid (see FIG. 3).

Example 8

Post-Transcription Reporter Vectors

Similar to the transcription reporter "control" vectors that contain a TRE-mCMV promoter, except that the mRNA destabilising element in the 3'-UTR is replaced with a MCS (see FIG. 4*a*). In some embodiments, MCS are also located in the 5' UTR and/or coding region.

Such a construct can be used as a "test" or a "control" vector for the post-transcriptional assays outlined herein.

In other examples, the control and one of the test reporters described above are both incorporated into a single vector, preferably a bi-directional plasmid (see FIG. 4*b*).

Example 9

Reporter Vectors for Assaying Specific Pathways

Vectors similar to those described herein, into which a regulatory element has been inserted into the MCS for the purpose of studying or measuring the function of said regulatory element. For example, plasmids similar to the transcription reporter plasmids outlined herein, except that they contain within the MCS, a promoter or promoter element(s) or enhancer(s) that are responsive to pathways such as those referred to in Table 1 and/or contain any of the following cis-acting enhancer elements as described in Clontech's Mercury Pathway Profiling Systems: AP1, CRE, E2F, GRE, HSE, ISRE, Myc, NFAT, NFκB, p53, Rb, SRE. The reporter is preferably a destabilised version of GFP, luciferase or SEAP.

Cell Lines and Mice for Assaying Specific Pathways

Cell lines or genetically modified mice stably expressing one or more of the vectors described herein.

Example 10

Method of Use

The vectors described in this invention are used for experimentation in essentially the same manner as the existing vectors that they replace, with the exception of the new methods described herein.

Method of Construction

The vectors and DNA constructs outlined here are assembled using standard cloning techniques. The SV40 and TRE-mCMV promoters described here as well as the more standard components of plasmid vectors (e.g., origin of replication, antibiotic resistance or another selection gene) are readily available in a variety of common vectors. DNA sequences encoding the destabilised variants of EGFP (e.g., d1EGFP, d1EYFP, d1ECFP and d2EGFP, d2EYFP, d2ECFP) are available from Clontech (Clontech Laboratories Inc., Palo Alto, Calif., USA). DNA sequences encoding destabilised DsRed variants are constructed by fusing to the 3' end of the DsRed encoding region, sequences encoding the degradation domains (or mutants thereof) from short-lived proteins. For example, amino acids 422–461 from mouse ornithine decarboxylase, which contains a PEST sequence. Such sequences could potentially be derived from existing dEGFP variants.

Example 11

Summary

In summary the present vectors and methods are now available:

Expression vectors or parts thereof that incorporate one or more mRNA instability elements in order to provide a relatively short-lived mRNA. Compared to existing expression vectors, the vectors claimed here provide kinetics of protein expression that correlate more closely with promoter activity. For example, the time lag between decreased promoter activity and decreased mRNA and protein levels is substantially reduced.

Expression vectors or parts thereof encoding a destabilised mRNA that in turn, encodes a destabilised protein. Compared to existing vectors, the vectors claimed here provide kinetics of protein expression that correlate more closely with promoter activity.

Expression vectors or parts thereof in which the mRNA destabilising elements are comprised of sequences cloned from short-lived mRNAs such as c-fos, examples of short-lived mRNAs include; c-fos, c-myc, GM-CSF, IL-3, TNF-alpha, IL-2, IL-6, IL-8, Urokinase, bcl-2, SGLT1 (Na(+)-coupled glucose transporter), Cox-2 (cyclooxygenase 2), IL8, PAI-2 (plasminogen activator inhibitor type 2), beta1-adrenergic receptor, GAP43 (5'-UTR and 3'-UTR) AU-rich elements (AREs) and/or U-rich elements, including but not limited to single, tandem or multiple or overlapping copies of the nonamer UUAUUUA(U/A)(U/A) [SEQ ID NO:2] (where U/A is either an A or a U) (Lagnado et al 1994) and/or the pentamer AUUUA [SEQ ID NO:3] (Xu et al 997) and/or the tetramer AUUU [SEQ ID NO:4] (Zubiaga et al. 1995). Also included are minor modifications to or permutations of the elements listed above. The term "tandem copies," allows for both duplication and/or non-duplication of one or more of the outer nucleotides. For example, tandem copies of the pentamer AUUUA [SEQ ID NO:3], includes sequences such as AUUUAUUUAUUUA [SEQ ID NO:5] as well as AUUUAAUUUAAUUUA [SEQ ID NO:6]. The 3'-UTR or 5'-UTR regions of short-lived mRNAs often contain destabilising sequences.

Expression vectors or parts thereof in which the mRNA destabilising elements were identified or validated using the vectors described herein, which provide substantially improved methods for identifying such elements.

Expression vectors or parts thereof, in which the destabilised mRNA encodes a short-lived reporter protein such as a destabilised variant of EGFP or luciferase. Compared to existing reporter vectors, the vectors claimed here provide kinetics of reporter expression that correlate more closely with promoter activity. For example, the time lag between decreased promoter activity and decreased mRNA and protein levels is substantially reduced.

Sets of reporter vectors or parts thereof that encode similarly destabilised mRNAs (similar to other vectors in the same set), which in turn, encode similarly (similar to other vectors in the same set) destabilised variants of EGFP or DsRed or other fluorescent markers. One or more vectors (control vectors) within each set contain a constitutive promoter (e.g., SV40, CMV, RSV, TK, TS; see FIG. 2b) or an inducible promoter (e.g., TRE-mCMV; see FIG. 2c), whereas the other vectors (test vectors) within each set contain a cloning site (e.g., MCS) in place of the promoter (e.g., see FIG. 2a). Applications of these vectors include but are not limited to the study or measurement of promoter activity. For example, a promoter element of interest can be cloned into the MCS of a test vector encoding d1EGFP and reporter expression measured relative to that of a control vector expressing d1EYFP. Also claimed is each individual vector described well as bi-directional vectors or other single vector systems that incorporate one test and one control reporter construct within the same vector (e.g., FIG. 3a and FIG. 3b). Compared to existing sets of reporter vectors, the vector sets claimed here offer the following advantages:

(a) A measurement of promoter activity that is closer to real-time.

(b) Decreased errors due to the closer similarity between control and test constructs.

(c) Decreased errors resulting from cross talk between test promoters and the control promoters. By utilising inducible promoters in the control vectors, such cross talk is minimised and/or identified and corrected for via measurement with and without induction.

(d) Can be used in conjunction with the flow cytometry/LSC methods described.

Reporter vectors or sets of reporter vectors or parts thereof that utilise an inducible promoter, preferably but not exclusively the tetracycline responsive element (TRE), to drive expression of a destabilised fluorescent reporter protein (preferably but not exclusively destabilised EGFP variants). Such vectors contain cloning sites in the 3'-UTR (e.g., FIG. 4a) and/or 5'-UTR and/or reporter coding region, such that regulatory elements or putative regulatory elements can be cloned into a vector expressing one color fluorescent reporter and, if required, compared to a control vector which expresses a different color reporter and does not contain the element of interest. Such vectors have applications in the study or measurement of post-transcriptional regulation, since transcription can be shut off as desired via the inducible promoter. The advantages offered by these vectors include those listed in b–d, the ability to separate post-transcriptional effects from transcriptional effects and also:

(a) incorporation of convenient cloning sites, not present in other vectors; and (b) the technique is more rapid than any existing method.

Single vector systems that essentially link one test and one control construct and described (e.g., FIG. 4b). Both test and control reporters are driven by an inducible promoter and the cloning sites allow ligation of regulatory elements into the test construct only. In addition to the advantages of vectors outlined, the single vector systems eliminate problems and inaccuracies associated with co-transfection of separate test and control vectors.

The use of flow cytometry or LSC to measure the levels of 2 or more fluorescent reporters expressed via the vectors outlined. In this application, the method yields thousands to hundreds of thousands of data points per sample versus one datum point for existing enzyme-based assays. Two or more reporters (control and test) as well as additional parameters (e.g., DNA content, levels of other proteins) can be measured individually in every cell. Also encompassed is the use of flow cytometry to correlate the levels of 2 or more reporters in multiple cells within the same sample and the utilisation of such data to optimise transfection protocols and/or identify problems associated with co-transfection. For example, invalid samples can be identified by the lack of a good linear relationship between test and control reporter levels. Such errors go unnoticed in current methods.

Methods for utilising the post-transcriptional reporter vectors claimed. These methods are best summarised by using the example of a study aimed at determining whether a specific 3'-UTR fragment affects mRNA stability. Although this example is one of transient expression, stable transfection could also be used.

(i) The 3'-UTR fragment is ligated into the 3'-UTR cloning site of the test vector and co-transfected with the control vector into a Tet-Off cell line. In the case of the single vector system, no control vector is required. 5'-UTR fragments can be tested by inserting them into vectors with a 5'-UTR cloning site.

(ii) The cells are grown in the absence of doxycycline (or tetracycline) for 6–48 h to allow expression of both vectors. Alternatively, cells are grown with low doses of doxycycline (or tetracycline), for 6–48 h to block transcription and then switched to medium without doxycycline (or tetracycline) for 2–12 h to provide a brief burst of transcription.

(iii) High doses of doxycycline (or tetracycline) are then applied to shut off transcription from both vectors.

(iv) The fluorescence of both reporters is measured (by flow cytometry, fluorometry or LSC) in a time course following addition of doxycycline (or tetracycline).

If the cloned element confers mRNA instability, a more rapid decrease in "test" fluorescence will be seen compared to "control" fluorescence of the same cells or sample. Similar studies can be used to test a mRNA element's response to certain stimuli or its effect in different cells or cells expressing different amounts of a specific protein, such as a RNA-binding protein. Applying the stimulus after doxycycline will determine whether pre-existing transcripts are affected by the stimulus. Inserting the element in different locations (e.g., 5'-UTR, 3'-UTR) will determine whether its function is dependent on position. Inserting a protein/polypeptide coding sequence (in frame) within the reporter protein-coding region of the vector can be used to determine the effect of that sequence on mRNA and protein stability.

RNA can be extracted from transfected cells and used to measure reporter mRNA directly.

Cell lines transiently or stably expressing one or more of the expression constructs or parts thereof claimed.

Cell lines transiently or stably expressing one or more of the expression constructs or parts thereof claimed, wherein the expression construct contains a regulatory element that serves as a marker for the activation of signal transduction pathways associated with human disease and/or response to drug treatment. Such pathways include, but are not restricted to the list in Table 1 and those indicated elsewhere in this document (e.g., CRE, SRE, AP1, cyclin A, B and D1 promoters).

Transgenic mice, knock-in mice or other genetically modified mice expressing one or more of the expression constructs or parts thereof claimed.

Transgenic mice, knock-in mice or other genetically modified mice expressing one or more of the expression constructs or parts thereof claimed, wherein the expression construct contains a regulatory element that serves as a marker for the activation of signal transduction pathways associated with human disease and/or response to drug treatment. Such pathways include, but are not restricted to the list in Table 1.

Destabilised variants of DsRed or the mutant DsRed1-E5. These can be constructed by fusing to the C-terminus of DsRed, degradation domains (or mutants thereof) from various unstable proteins. For example, amino acids 422–461 of mouse ornithine decarboxylase, which contains a PEST sequence (Li et al. 1998). Additional destabilising elements can also be added. Also contemplated are DNA constructs encoding destabilised variants of DsRed.

Vectors encoding destabilised variants of DsRed outlined, including such vectors also containing the mRNA instability elements outlined.

The following method for creating Tet-Off or Tet-On cell lines:

The tTA or rtTA expression vector, preferably a retrovirus, adenovirus or plasmid, is stably expressed in the cell line of interest using standard techniques and expressing cells are isolated via a drug resistance marker. These cells are then transiently transfected with a TRE-vGFP construct and subjected to several rounds of cell sorting by flow cytometry. For example, good Tet-Off cells would show no fluorescence in the presence of doxycycline and are sorted as such. After a further 5–48 hr without doxycycline, green cells are sorted. Finally, the cells are grown for a week or more without doxycycline and sorted a final time to eliminate stably transfected (green) cells.

Example 12

Vectors Incorporating mRNA and Protein-Destabilising Elements

The coding region of interest (e.g., a reporter such as EGFP or luciferase) could include combined sequence of a protein-destabilising element (e.g., d1 mutant of MODC; Clontech, but also including other PEST sequences or other protein-destabilising elements such as ubiquitination sites) and a mRNA destabilising element (e.g., AU-rich element).

For example, the stop codon of luciferase and DsRed is replaced with a Hind3 site (AAGCTT [SEQ ID NO:7]) to allow the addition of the sequence: AAGCTTAGCCATG-GCTTCCCGCCGGCGGTGGCGGCGCAGGATGATGG-CACGCTGCCCA TGTCTTGTGCCCAGGAGAGCGG-GATGGACCGTCACCCTGCAGCCTGTGCT-TCTGCTAG GATCAATGTGTAG [SEQ ID NO:8] which is Clontech's d1 mutant of MODC that confers a 1-hr half life to EGFP. This is followed by a linker (which becomes part of the 3'-UTR and then: UUAUUUAUU GGCGG UUAU-UUAUU CGGCG UUAUUUAUU GCGCG UUAU-UUAUU ACUAG [SEQ ID NO:9] which contains 4 nonamers and connects to the XbaI site of the parent vector (pGL3; Promega) also in the 3'-UTR but further downstream.

Example 13

Direct Ligation of PCR Products

Inclusion into the MCS of a vector of two separate but nearby RE recognition sites, which, when cut with that/those RE(s), leave a 3' overhang of a single T nucleotide at both ends of the remaining vector. For example, the recognition sequence for Ec1HK1 is GACNNN, NNGTC [SEQ ID NO:10] (cuts between $3^{rd}$ and $4^{th}$ N from 5' leaving a 3' overhang of a single N at each end). Two of these sites are incorporating into the MCS, such that the short region between them is released by digestion with Ec1HK1, leaving a linearised vector with a 3' overhang of a single N at each end. In this example, the upstream recognition sequence should be 5'GACNNTNNGTC3' [SEQ ID NO:11] and the downstream sequence 5'GACNNANNGTC3' [SEQ ID NO:12]. After cutting with Ec1HK1, the large vector fragment will contain a single 3' T overhang at both ends (similar to Promega's pGEM-T Easy vector). This facilitates the direct ligation of PCR products that are produced with a polymerase such as Taq, that yields a 5' A overhang. This constitutes a significant improvement over standard MCSs, which do not support direct ligation of PCR products without inclusion of RE sites into PCR primers and subsequent digestion of PCR product. This is also a significant improvement over the pGEM-T Easy vector, which cannot be amplified (supplied as linear) and is useful only for subcloning (i.e., PCR products are typically ligated into pGEM-T Easy, amplified and then removed by RE digestion and subsequently cloned into the expression vector of interest). Thus, the present MCS permits direct ligation of PCR products without the need for digesting them with a RE (which is often problematic) or subcloning them into an intermediate vector.

Example 14

Destabilised Reporter Model Shows Improved Real-Time Analysis

Plasmid reporter vectors were assembled in a pGL3-Basic (Promega) backbone (ampicillin resistance gene etc.) using standard cloning techniques. A tetracycline-responsive element (TRE), derived from Clontech's pTRE-d2EGFP vector was inserted into the MCS. In some constructs the luciferase-coding region was replaced with the d1EGFP- or d2EGFP-coding sequence (including Kozak sequence) as defined by Clontech. This was achieved by PCR using appropriate primers with convenient 5' flanking RE sites. In some constructs, specific examples of mRNA destabilising elements were cloned into the 3'-UTR-encoding region. Typically, these sequences were prepared by synthesising and then hybridising the sense and antisense sequences. Flanking sequences provided overhanging "sticky ends" that are compatible with those generated when the 3'-UTR-encoding region is cut with specific restriction enzymes. Following digestion of the vector with these enzymes and subsequent purification, the hybridised oligomers were ligated into the vector using standard techniques. PCR of genomic DNA or cDNA from an appropriate source was used as an alternative method for obtaining the larger destabilising elements such as c-myc-ARE. Very small elements (e.g., 1 or 2 nonamers) were incorporated into a reverse PCR primer that contained a 5' flanking RE site and a 3' flanking region complementary to the pre-existing 3'-UTR in the vector template. Following PCR with an appropriate forward primer (complementary to the protein-coding region and overlapping an endogenous RE site), the PCR product was digested with the appropriate RE sites and ligated into the original vector.

Nomenclature:

B=Vector backbone derived from Promega's pGL3-Basic;

T=Tetracycline-responsive element (TRE), derived from Clontech's pTRE-d2EGFP vector and used as a promoter to drive transcription of the reporter;

G1=GFP with 1 hr half-life used as reporter i.e., d1EGFP protein encoding sequence as defined by Clontech;

G2=GFP with 2 hr half-life used as reporter i.e., d2EGFP protein encoding sequence as defined by Clontech;

L=Luciferase used as reporter i.e., The Firefly luciferase encoding sequence from pGL3-Basic (Promega);

R=DsRed2 used as the reporter;

R1=DsRed fused at the carboxy-end to the same MODC mutant as present in d1EGFP;

N6=6 copies of the nonamer TTATTTATT [SEQ ID NO:13] inserted into the 3'-UTR-encoding region.

N4=4 copies of the nonamer TTATTTATT [SEQ ID NO:13] inserted into the 3'-UTR-encoding region;

N2=2 copies of the nonamer TTATTTATT [SEQ ID NO:13] inserted into the 3'-UTR-encoding region;

N1=1 copy of the nonamer TTATTTATT [SEQ ID NO:13] inserted into the 3'-UTR-encoding region;

fos=The c-fos ARE as defined by Shyu et al (1989) inserted into the 3'-UTR-encoding region i.e., 5'AAAACGTTTTTATTGTGTTTTTAATT-TATTTATTAA GATGGATTCTCAGATATT-TATATTTTTATTTTATTTTTTT3' [SEQ ID NO:14];

myc=the myc ARE defined as follows 5'ATGCATGAT-CAAATGCAACCTCACA ACCTTGGCTGAGTCT-TGAGACTGAAAGATTTAGCCATAATG-TAAACTGCCT CAAATTGGACTTTGGGCATAAAA-GAACTTTTTATGCTTACCATCTTTTTTT TTTCTT-TAACAGATTTGTATTTAAGAATTGTTTT-TAAAAAATTTTAAGATTT ACACAATGTTTCTCTGTAAATATTGC-CATTAAATGTAAATAACTTT3' [SEQ ID NO:15].

Method:

Five micrograms of maxiprep quality DNA was transfected into ~50% confluent 10 cm flasks of HeLa Tet-Off cells (Clontech) using Fugene reagent (Roche). ~Ten hours later, the flasks of cells were each split into ~12 small (6 cm) dishes and then incubated overnight (~12–14 hrs). At this time point (typically designated time zero or $T_0$), doxycycline was added to the culture media of most plates at a final concentration of 1 microgram per ml. Cells were trypsinised and collected at this and subsequent time points. For constructs expressing GFP, these samples were analysed by flow cytometry using standard FITC filters. Total GFP fluorescence was measured by gating out non-transfected cells (background fluorescence only) and then multiplying the mean fluorescence per cell (with background fluorescence subtracted) by the number of positive cells. RFP fluorescence (DsRed) was measured similarly using appropriate filters. Cells transfected with luciferase-encoding vectors were lysed and measured in a luminometer using Promega's Dual Luciferase Assay methods and reagents.

Data are typically expressed as the percentage of reporter (fluorescence or luminescence) remaining, relative to time zero.

Since the doxycycline added at time zero causes a block in transcription of the reporter, the rate of decrease in reporter levels indicates the time lag between altered transcription and altered reporter/protein levels. A prime purpose of the invention is to reduce this time lag and FIGS. 7, 8, 9 and 11–14 demonstrate that this is achieved.

Figure 7:
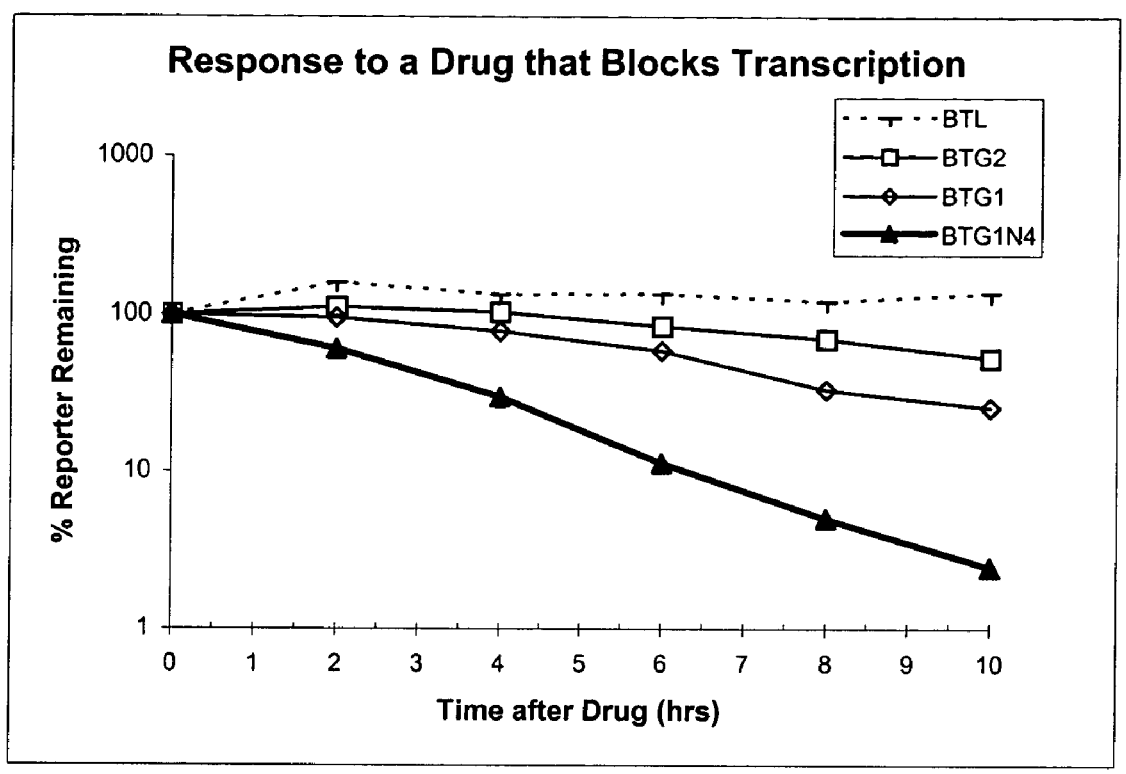
FIG. 7 is a graphical representation showing different reporter levels for BTL, BTG2, BTG1 and BTG1N4 expression vectors on a time course after blocking transcription. Tet-Off HeLa cells were transfected with the following reporter plasmids, each containing a TRE promoter linked to a reporter gene; BTL (luciferase), BTG2 (d2EGFP), BTG1 (d1EGFP) and BTG1N4 (same as BTG1 but with 4 copies of the nonamer UUAUUUAUU [SEQ ID NO:1] present in the 3'-UTR-encoding region). Ten hrs after transfection, each flask of cells was split into multiple small plates. Doxycycline (1 µg/mL) was added at 24 hrs after transfection (time zero) to block transcription of the reporter genes. Reporter levels (fluorescence or luminescence) were measured at this and subsequent time points, as described in Example 14, and presented as the percentage of time zero. No decrease in luciferase activity (BTL) was seen during the 10 hr time-course. The 2 hr half-life EGFP construct (BTG2) showed a moderate response to the doxycycline-induced block in transcription and a faster response was seen with the 1 hr half-life EGFP (BTG1). The construct containing the nonamers (BTG1N4), however, showed by far the fastest response to this block in transcription.
Figure 8:
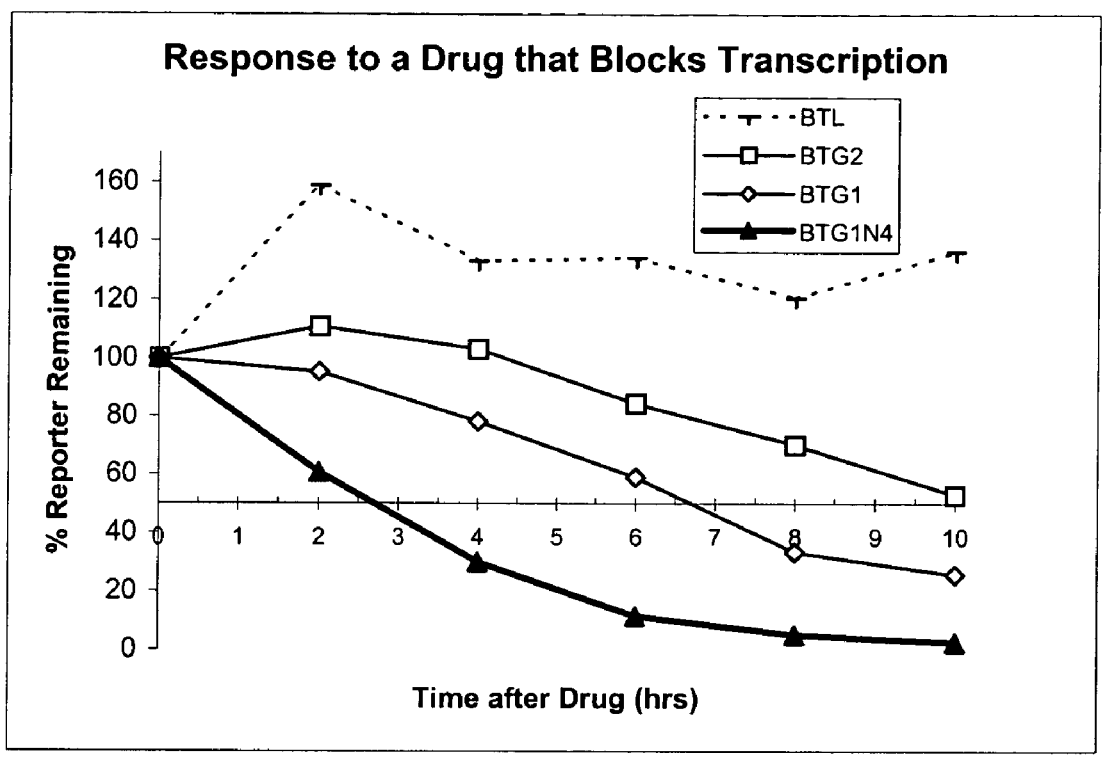
FIG. 8 is a graphical representation showing the data used for FIG. 7 displayed on a linear scale. The doxycycline-induced block in transcription is detectable as a 50% block in reporter levels after approximately 6.5 hrs with BTG1. However, this is reduced to less than 3 hrs by inclusion of the nonamers (BTG1N4).

As an example of the utility of this invention, a pharmaceutical company may wish to screen for drugs that reduce transcription of a gene involved in disease. The tetracycline/doxycycline-induced block in transcription from the TRE promoter is a model of such a system. FIGS. 7 and 8 show that with the standard luciferase reporter vectors, even a total block in transcription (with doxycycline) is not detectable as a decrease in luciferase activity within 10 hrs. The destabilised EGFP mutants represent an improvement in that the total block in transcription is detectable as a 50% decrease in EGFP fluorescence within 11 hrs (d2EGFP; BTG2) or 7 hrs (d1EGFP; BTG1). However, when the latter reporter is combined with a mRNA destabilising element such as 4 copies of the nonamer UUAUUUAUU [SEQ ID NO:1] (BTG1N4), a 50% decrease in reporter levels is detectable within 3 hrs. It follows that an increase in a transcription would also be detected sooner with constructs containing the destabilising elements (Roth, 1995).

Figure 9:
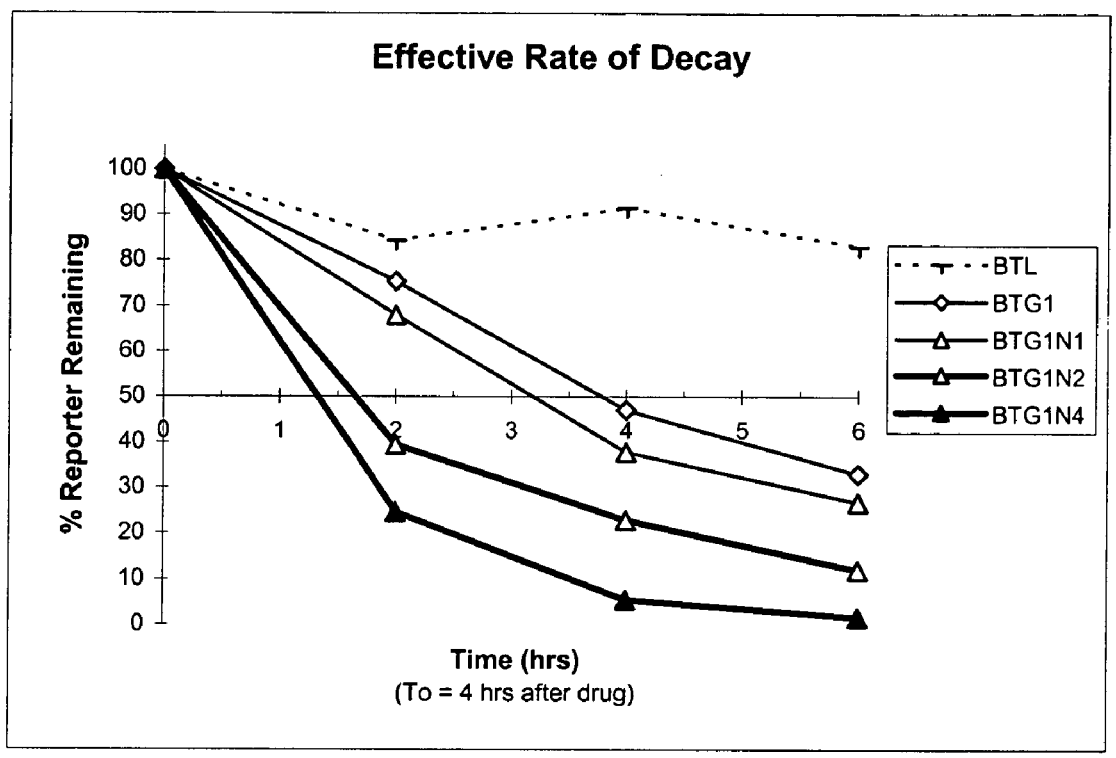
FIG. 9 is a graphical representation showing the effect of different numbers (1, 2 or 4) of nonamer RNA destabilising elements. A time-course was performed as described in FIG. 7, except with time zero defined as 4 hrs after addition of doxycycline to eliminate the effect of the delay in the action of this drug. The presence of a single nonamer (BTG1N1) was sufficient to increase the "effective rate of decay," whereas progressively stronger effects were seen with 2 nonamers (BTG1N2) and 4 nonamers (BTG1N4). The latter construct showed an "effective half-life" of ~1 hr 20 mins, which is little more than the 1 hr half-life of the protein alone.
Figure 13:
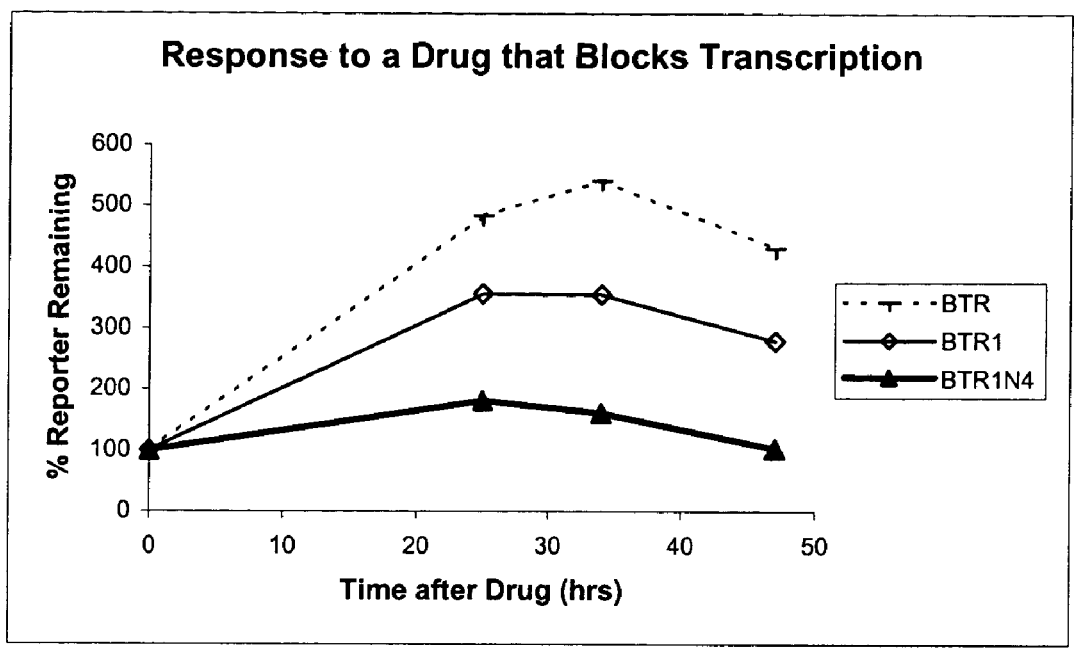
FIG. 13 is a graphical representation showing reporter levels over time using DsRed destabilised by RNA destabilising elements and protein-destabilising elements. A time course was performed as described in FIG. 7 and Example 14. The constructs used were DsRed2 (BTR), DsRed-MODC (BTR1) and DsRed-MODC containing 4 UUAUUUAUU [SEQ ID NO:1] nonamers in the 3'-UTR (BTR1N4). After blocking transcription with doxycycline, red fluorescence continues to increase with all constructs. This is substantially reduced by the protein-destabilising element and further reduced by the mRNA destabilising element.

Of course the action of doxycycline is not immediate so that part of the time lag is due to the time required for this drug to induce a 100% transcriptional block. Therefore, the "Effective rate of decay" was measured by plotting data points subsequent to and relative to the time point at 4 hrs after addition of doxycycline (FIG. 9). The effective rate of decay therefore excludes the delay in drug action and is a combined effect of protein and mRNA half-lives. FIG. 9 shows the effective rate of decay with constructs containing 1, 2 or 4 nonamers. These data show that 4 nonamers are more efficient than 2, which is more efficient than 1. Furthermore, these data show that by combining a 1 hr half-life protein (d1EGFP) with 4 nonamers, an effective rate of decay of approximately 1 hr 20 mins can be achieved. This is very close to the 1 hr half-life of the protein and demonstrates an extremely short mRNA half-life. Further reduction could be achieved by combining 2 or more different mRNA instability elements (FIG. 13). However, this is unlikely to be required for most applications. Applications that require a more moderate destabilising effect could utilise 1 or 2 nonamers, rather than 4.

Figure 10:
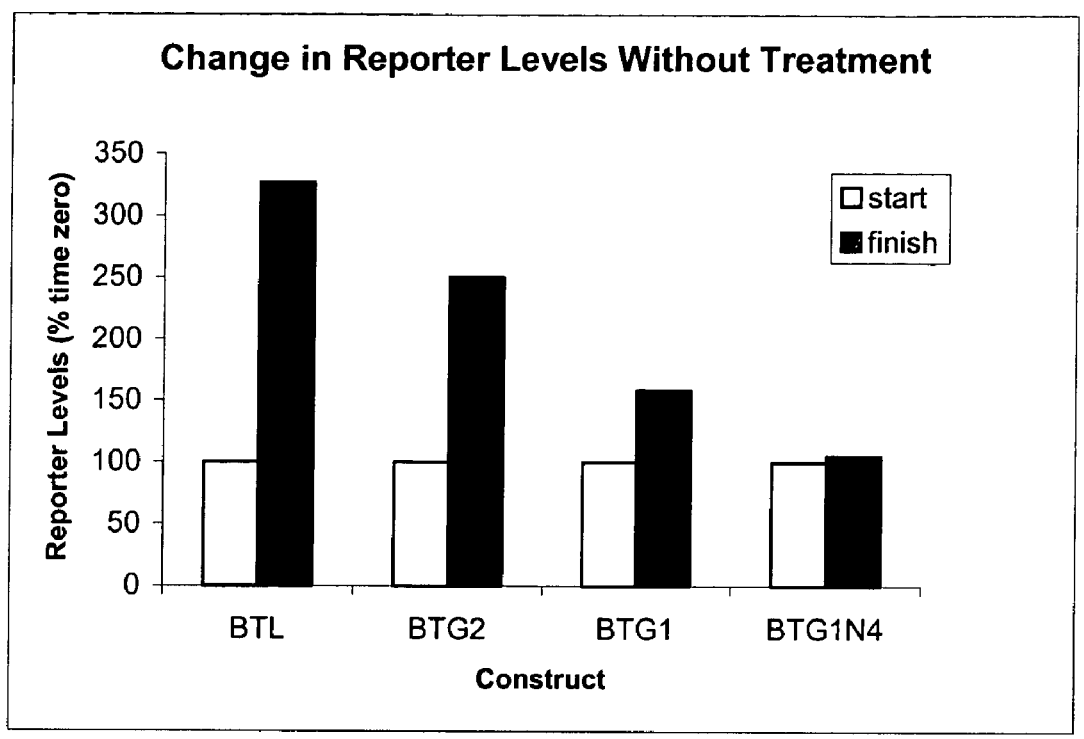
FIG. 10 is a graphical representation showing changing reporter levels over time in the absence of a transcriptional block. A time-course was performed as described in FIG. 7. However, the data presented represent samples not treated with doxycycline and measured at 24 hrs after transfection (start) or 34 hrs after transfection (finish). Consistent expression levels were seen only with BTG1N4.
Figure 11:
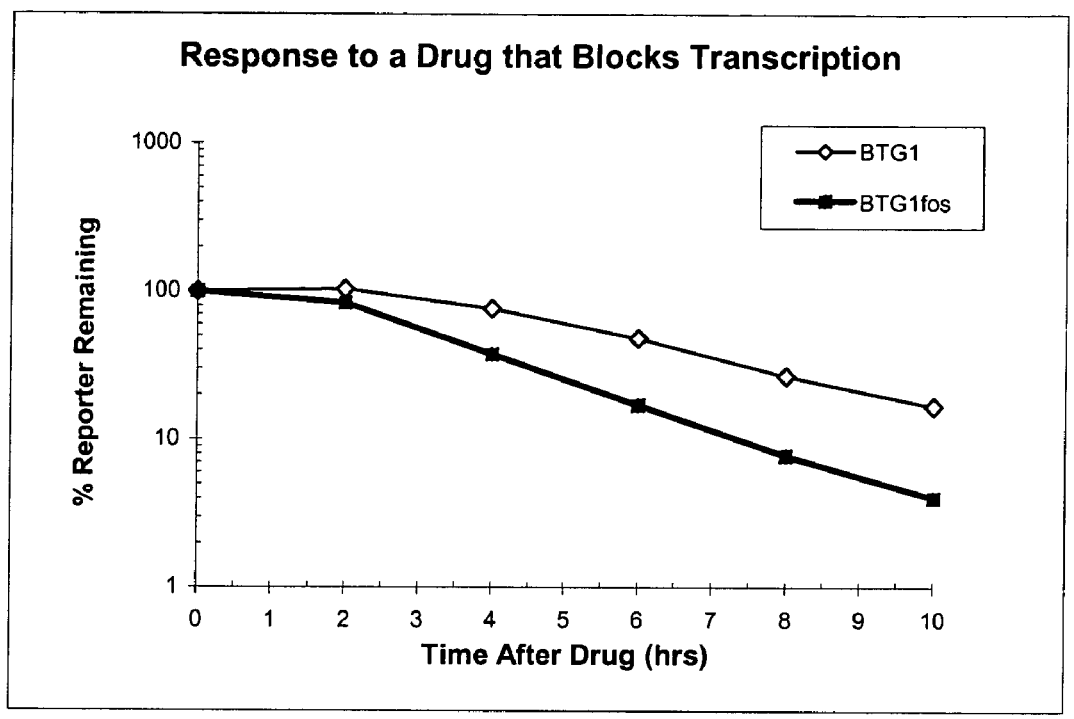
FIG. 11 is a graphical representation showing changes in reporter levels over time in the absence of a transcriptional block. A time-course was performed as described in FIG. 7. BTG1fos contains the c-fos ARE. These data demonstrate that different types of mRNA destabilising elements can be used to achieve the same effect.

With the standard luciferase reporter, luminescence actually increased after the addition of doxycycline. This is most apparent when the data is expressed on a linear scale (FIG. 8) and can be explained, in part, by the delay in the action of doxycycline. However, even from 4 hrs onwards, no decay is evident, demonstrating the inadequacy of this reporter for measuring changes in transcription over time. A further problem of this vector is revealed in FIG. 10. These data relate to changes in reporter levels over time (24–34 hrs post transfection), in the absence of any treatment or drug. Reporter levels generally increase during the first 24 hrs post transfection as the plasmids enter the cells and begin to be expressed. A decrease is generally seen from about 48 hrs as the plasmids are expelled from the cells. Therefore, measurements are typically taken between 24 and 48 hrs. In the absence of drugs or treatment, the new vector (BTG1N4), containing the instability elements, shows excellent stability of reporter levels. In contrast, the luciferase vector is clearly still ramping up expression levels. Constructs with moderate stability (e.g., BTG1) showed intermediate results. Clearly reporters with longer mRNA and protein half-lives will undergo a more lengthy ramping up phase as indicated in FIG. 10. The more stable expression levels seen with the new construct during the critical period of 24–34 hrs will facilitate accurate measurement and represent another advantage of the invention.

The rate of decrease in reporter levels can be compared between two or more constructs, which differ in their reporter mRNA sequence (e.g., in 3'-UTR) but encode the same protein or different proteins with the same half-life (e.g., d2EGFP, d2EYFP). In this context, differences in the rate of decay indicate an effect of the altered mRNA sequence on mRNA stability. For example, the presence of 4 UUAUUUAUU [SEQ ID NO:1] nonamers as DNA TTATTTATT [SEQ ID NO:13] (FIGS. 7–9) or the c-fos ARE (FIG. 11) [SEQ ID NO:14], within the 3'-UTR significantly increased the rate of mRNA decay. In addition to demonstrating the effectiveness of these elements, the methods and vectors used also represent a substantially improved system for detecting other cis-acting mRNA stability/instability elements and this process is also encompassed herein.

Figure 12:
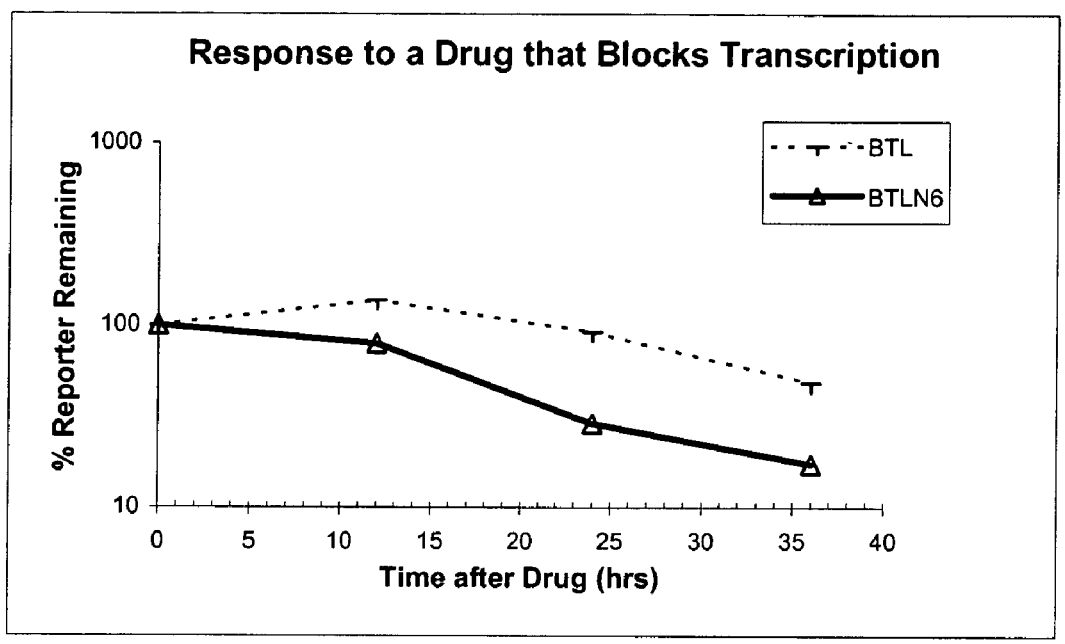
FIG. 12 is a graphical representation showing that RNA destabilising elements are useful in determining expression when a Luciferase reporter protein is used. A further enhancement would be expected using a luciferase reporter protein with protein-destabilising elements. A time-course was performed as described in FIG. 7, using two luciferase-expressing constructs. BTL contains the standard Firefly luciferase-coding region and 3'-UTR (derived from pGL3-Basic; Promega), whereas BTLN6 contains 6 copies of the nonamer UUAUUUAUU [SEQ ID NO:1] in the 3'-UTR.
Figure 14:
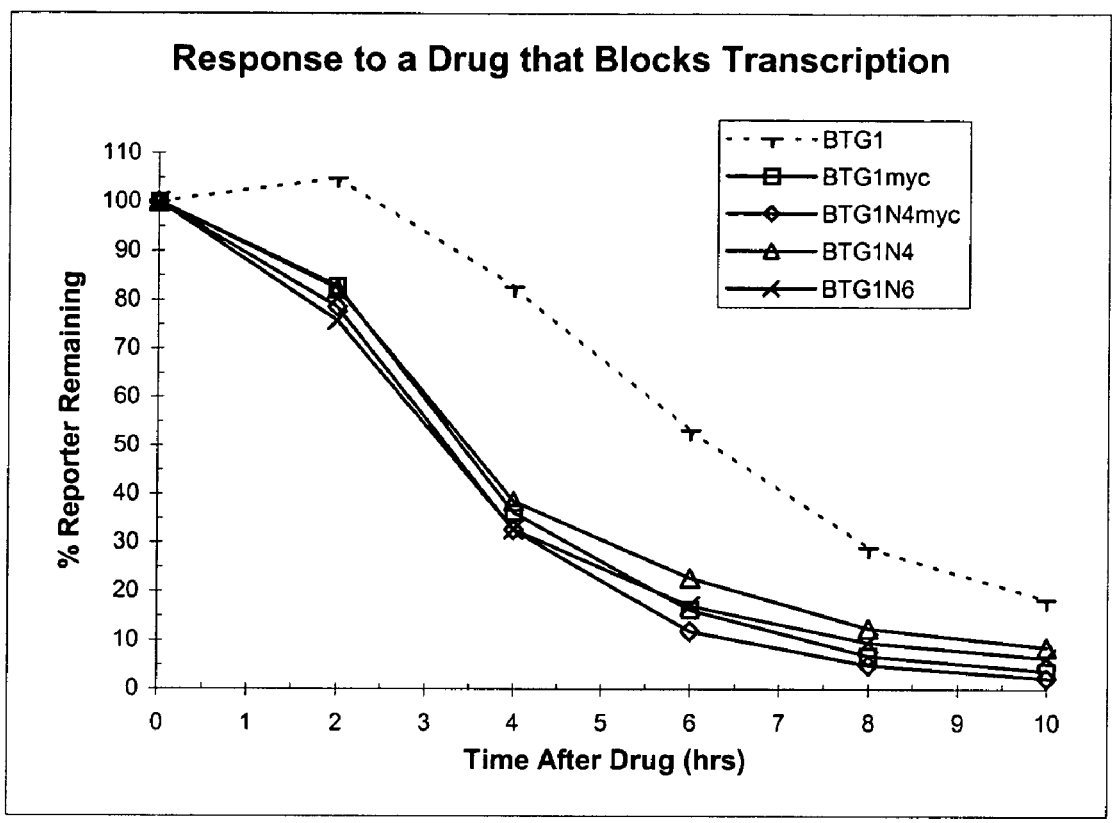
FIG. 14 is a graphical representation showing a time-course was performed as described in FIG. 7. All of the mRNA destabilising elements tested were very effective at increasing the rate of decay compared to controls (BTG1). These data show that the c-myc ARE is an effective destabilising element (BTG1myc) and that a modest increase in destabilising activity can be obtained by combining the myc ARE with 4 nonamers (BTG1N4myc). Six nonamers (BTG1N6) also appeared to destabilise somewhat more than 4 nonamers (BTG1N4).

As shown in FIGS. 12 to 14 mRNA destabilising elements work with Luciferase, GFP and DsRed not withstanding the low level of homology between these reporters. DsRed has only 23% homology with EGFP. As shown in FIG. 14 myc ARE (SEQ ID NO: 21) are effective and are also effective in combination with different destabilising elements.

Example 15 mRNA Destabilising Elements

RNA destabilising elements in accordance with the present invention can be derived inter alia from the 3'-UTR of the following genes. In most cases, the full-length 3'-UTR can be used. However, the U-rich and/or AU-rich elements can often be used alone.

(a) Phosphoenolpyruvate carboxykinase (PEPCK) mRNA destabilising elements described by Laterza OF et al. Regions within 3' half of 3'-UTR referred to as JW6 and JW7 i.e., GTATGTTTAAATTATTTTTATACACT-GCC CTTTCTTACCTTTCTTTACATAAT-TGAAATAGGTATCCTGACCA [SEQ ID NO:16].

(b) The Bicoid gene from *Drosophila melanogaster* comprises a mRNA destabilising element in first 43 nt of 3'-UTR (Surdej P. et al) such an element can be used inter alia to destabilise mRNA in insect cells.

(c) The Human Thioredoxin reductase gene (Gasdaska, J R et al). The entire 3'-UTR. Nucleotide 1933–3690 (contains 6 AU-rich elements). Segment containing 3 upstream AU repeats (nucleotide 1975–3360). There is also as Non-AU-rich destabilising element at nt 1933–2014.

(d) Heat Stable Antigen (HSA) Gene described in Zhou, Q et al. For example, nucleotides 1465–1625 in the 3'-UTR.

(e) Granulocyte-macrophage colony stimulating factor (GM-CSF) ARE described by Chyi-Ying, A et al AGUUAAUAUUUAUAUAUUUAUAUUUUAA AAUAUUUAUUUAUUUAUUUAUUUAA [SEQ ID NO:17] i.e., as DNA: AGTAATATTTATATATT-TATATTTTTAAAATATTTATTTATTTATTTATTTAA [SEQ ID NO:18].

(f) c-fos full length 3'-UTR or part thereof or ARE as defined by Shyu et al 5'AA AACGTTTTATTGT-GTTTTTAATTTATTTATTAAGATGGAT-TCTCAGAT ATTTATATTTTTATTTTATTTTTTT3' [SEQ ID NO:19] or by Peng, S et al. 5'TTTTATTGT-GTTTTTAATTTATTTATTAAGATGGAT-TCTCAGATATT TATATTTTTATTTTATTTTTTT3' [SEQ ID NO:20].

(g) c-jun ARE as described by Peng, S et al. 5'UUUCG-UUAACUGUGUAUGUA CAUAUAUAUAU-UUUUUAAUUUGAUUAAAGCUGAUUACU-GUGAAU AAACAGCUUCAUGCCUUUGUAAGUU3' [SEQ ID NO:21] Sequence as DNA: 5'TTTCGTTAACTGT-GTATGTACATATATATATTTTTAATTTGA TTAAAGCTGATTACTGTGAATAAA-CAGCTTCATGCCTTTGTAAGTT3' [SEQ ID NO:22] or the mutant thereof which does not contain a polyadenylation (AAUAAA [SEQ ID NO:23]) signal i.e., 5'UUUCGUUAACUGUGUAUGUA-CAUAUAUAUAUUUUUAAUUUGA UUAAAGCUGAUUACUGUGgAUccA-CAGCUUCAUGCCUUUGUAAGUU 3' [SEQ ID NO:24] or as DNA 5'TTTCGTTAACTGTGTATG-TACA TATATATATTTTTAATTTGAT-TAAAGCTGATTACTGTGgATccACAGC TTCAT-GCCTTTGTAAGTT3' [SEQ ID NO:25].

Sequences from the following genes, that include their respective ARE components as described by Henics, T. et al.:

(h) IFN-γ ARE: 5'UCUAUUUAUUAAUAUUUAACA-UUAUUUAUAUAU GGG3' [SEQ ID NO:26] or as DNA 5'TCTATTTATTAATATTTAAC ATTATT-TATATATGGG3' [SEQ ID NO:27].

(i) IL-2 ARE: 5'CUCUAUUUAUUUAAAUAU-UUAACUUUAAUUUAUUU UUGGAUGUAUU-GUUUACUAACUUUUAGUGCUUCCCACU-UAAAACA UAUCAGGCUUCUAUUUAUUUAAAUAU-UUAAAUUUUAUAUUUA UU3' [SEQ ID NO:28] or as DNA 5'CTCTATTTATTTAAATATTTAACT TTAATTTATTTTTGGATGTATTGTTTAC-TAACTTTTAGTGCTTCCACT TAAAACATAT-CAGGCTTCTATTTATTTAAATATT-TAAATTTTATATTT ATT3' [SEQ ID NO:29].

(j) c-myc ARE (see also SEQ ID NO:49): 5'AUAAAC-CCUAAUUUUUU UAUUUAAGUACAUUUUGCU-UUUUAAAGUU3' [SEQ ID NO:30] or as DNA 5'ATAAACCCTAATTTTTTTATTTAAGTA-CATTTTGCTTTTAAA GTT3' [SEQ ID NO:31].

(k) IL-10: 5'UAGAAUAUUUAUUACCUCUGAUAC-CUCAACCCCCAUUU CUAUUUAU-UUACUGAGCUUCUCUGUGAACGAUUUA-GAAAGAAGCC CAAUAUUAUAAUUUUUUUCAAUAUUUA-UUAUUUUCA3' [SEQ ID NO:32] or as DNA 5'TAGAATATTTATTACCTCTGATACCT-CAACCCCCA TTTCTATTTATTTACTGAGCT-TCTCTGTGAACGATTTAGAAAGAAGCC CAATATTATAATTTTTTTCAATATTTAT-TATTTTTCA3' [SEQ ID NO:33].

(l) bcl-2: Sequences from the bcl-2 3'-UTR that include all or part of the bcl-2 ARE as defined by Schiavone, N et al. 5'UCAGCUAUUUACUGCC AAAGG-GAAAUAUCAUUUAUUUUUUACAUUA-UUAAGAAAAAAGAU UUAUUUAUUUAAGA-CAGUCCCAUCAAAACUCCGUCUUUGGAAAUC 3' [SEQ ID NO:34] (M13994 from nt 2371–2475) or as DNA 5'TCAGCTATTTACTGCCAAAGGGAAATAT-CATTTATTTTTACATTAT TAAGAAAAAAGATT-TATTTATTTAAGACAGTCCCATCAAAACTCCGT CTTTGGAAATC3' [SEQ ID NO:35].

(m) TNF ARE: as described by Xu, N et al. 5'-AUUAU-UUAUUA UUUAUUUAUUAUUUAUUUAUUUA3' [SEQ ID NO:36] or as DNA 5'ATTATTTATT ATT-TATTTATTATTTATTT ATTA-3' [SEQ ID NO:37].

(n) IL-3 ARE: as described by Xu, N et al. 5'UAUUUUA-UUCCAUU AAGGCUAUUUAUUUAUGUAU-UUAUGUAUUUAUUUAUUUAUU3' [SEQ ID NO:38] or as DNA 5'-TAttTTATTCCATTAAGGC-TATTTAT TTATGTATTTATGTATTTATTTATTTATT-3' [SEQ ID NO:39].

(o) The nonamer UUAUUUAUU [SEQ ID NO:1] as DNA TTATTTATT [SEQ ID NO:13], as described by Zubiaga, A et al.

(p) The nonamer UUAUUUA(U/A)(U/A) [SEQ ID NO:2] as DNA TTATTTA(T/A)(T/A) [SEQ ID NO:40] as described by Lagnado, C et al.

(q) The pentamer AUUUA [SEQ ID NO:3] as described by Xu, N et al. or as DNA ATTTA [SEQ ID NO:41].

(r) The tetramer AUUU [SEQ ID NO:4] or as DNA ATTT [SEQ ID NO:42].

AU-rich elements (AREs) in general of both class I and class II as described by Chen, C and Shyu, A.

(s) Plants have DST (downstream sequences) which act as destabilising elements. DST sequence are defined in: Newnan, T et al. A proposed consensus DST sequence is: GGAgN$_{2-9}$cATAGATTaN$_{3-8}$(A/C)(T/A)(A/T)TttGTA(T/C) [SEQ ID NO:43].
This is based on comparison of 9 different DST sequences.
Bold=conserved in 9/9 genes.
Capital=conserved in at least 7/9 genes
N2–9=variable length region of 2–9 nucleotides; average=5.
N3–8=variable length region of 3–8 nucleotides; average=6.
Distance from stop codon=19–83 nt.
Further examples of DST sequences include the:
Soybean 10A5 gene; 5'GGAGN$_5$CATAGATTAN$_8$AAATTTGTAC3' [SEQ ID NO:44].
*Arabidopsis* SAURAC1 gene: 5'GGAAN9CATAGATCGN$_8$CAATGCGTAT3' [SEQ ID NO:45].
DST sequences are an alternative to AU-rich elements for use in plants. Both AU-rich elements and DST sequences destabilise transcripts in plants.
(t) Iron Responsive Element (IRE):
as described for example by Thomson, A et al. 1999.
IREs contain consensus CAGUG in a hairpin-loop.
Examples:
Ferritin IRE: GUUCUUGCUUCAACAGUGUUUGAACGGAAC [SEQ ID NO:46] or as DNA GTTCTTGCTTCAACAGTGTTTGAACGGAAC [SEQ ID NO:47].
Transferrin Receptor IRE: GAUUAUCGGGAGCAGUGUCUUCCAUAAUC [SEQ ID NO:48]or as DNA GATTATCGGGAGCAGTGTCTTCCATAATC [SEQ ID NO:49].
Iron Regulatory Proteins (IRPs; e.g., IRP1 and 2) bind IREs in an iron-dependent fashion. Binding is also modulated by various other stimuli and treatments (e.g., oxidative stress, nitric oxide, erythropoietin, thyroid hormone or phosphorylation by PKCs.
IREs can modulate both translational efficiency and mRNA stability. For example, the 5'-UTR IRE in Ferritin mRNA blocks translation only when bound to an IRP. The IREs in the 3'-UTR of Transferrin receptor mRNA inhibit mRNA decay when bound by an IRP. Therefore, IREs can be inserted into 5'-UTR or 3'-UTR of expression vectors to provide expression that can be controlled by modulating iron levels or other stimuli.
Destabilising elements can be used with Clontech's Mercury Pathway Profiling vectors and in vivo kinase assay kits. Clontech produce 3 different protein-destabilising elements, all containing a PEST sequence and all derived from the MODC gene. Different mutant MODCs placed at the carboxy-end of EGFP provide protein half-lives of 1 hr, 2 hr and 4 hr. mRNA destabilising elements in accordance with the present invention can be used in conjunction with these and any other protein-destabilising element (e.g., ubiquitination signals).
(u) c-myc ARE may also be defined as: 5'ATGCATGATCAAATGCAACCTCAC AACCTTGGCTGAGTCTTGAGACTGAAAGATTTAGCCATAATGTAAACTGCCTCAAATTGGACTTTGGGCATAAAAGAACTTTTTTATGCTTACCATCTTTTTTTTTTCTTTAACAGATTTGTATTTAAGAATTGTTTTAAAA AATTTTAA-GATTTACACAATGTTTCTCTGTAAATATTGCCATTAAATG TAAATAACTTT3' [SEQ ID NO:50].
(v) Another useful mRNA element can be obtained from histone mRNA, Specifically, 3'-UTR sequences including a consensus stem loop structure are described by Gallie, D et al.: UGA-N$_{20-40}$-CCAAAGGYYYUUYUN ARRRCCACCCA [SEQ ID NO:51], where Y=pyrimidine, R=purine, N=any nucleotide or as DNA TGA-N$_{20-40}$-CCAAAGGYYYTTYTNARRRCCACCCA [SEQ ID NO:52].
Such sequences can increase translational efficiency. Moreover, they are capable of directing mRNA decay specifically outside of S phase. Reporter constructs containing a cell-cycle-specific promoter, together with mRNA destabilising elements are contemplated in this invention as a tool for directing cell-cycle specific expression (e.g., of a reporter). The histone 3'-UTR element offers an alternative for use with an S-phase or late G1 specific promoter, since it will direct increased mRNA decay in G2 relative to S-phase, thus further restricting protein expression to S phase.
Yet another use of 3'-UTR elements in expression vectors is for the purpose of specifically localising the chimeric mRNA. For example, the utrophin 3'-UTR is capable of directing reporter mRNA to the cytoskeletal-bound polysomes. mRNA stabilising elements are also contained in this 3'-UTR (Gramolini, A, et al.).

Example 16 mRNA Stabilising Elements and Expression Vectors Encoding a Stabilised mRNA

Stabilising sequences may contain CT-rich elements and/or sequences derived from long-lived mRNAs (particularly 3'-UTR regions)
CT-rich elements may contain (C/U)CCAN$_x$CCC(U/A)Py$_x$UC(C/U)CC [SEQ ID NO:53] as described by Holcik and Liebhaber, 1997.
CT-rich elements may contain the following element CCTCCTGCCCGCTGGGCCTCCCAACGGGCCCTCCTCCCCTCCTTGC [SEQ ID NO:54] or parts thereof, including CCTCC [SEQ ID NO:55], CCTCCTGCC [SEQ ID NO:56] or CCCTCCTCCCCTGG [SEQ ID NO:57].
A 14-nt pyrimidine-rich region from the 3'-UTR of human beta-globin described by Yu and Russell is also contemplated for use as a stabilising element.
Examples of long-lived mRNAs from which stabilising elements may be derived include; Alpha2 globin, Alpha1 globin, beta globin. From human, mouse, rabbit or other species, bovine growth hormone 3'-UTR.
The mRNA instability elements described herein generally act in a dominant-fashion to destabilise chimeric genes. It follows, therefore that mRNA stabilising elements are often recessive-acting. For example, insertion of a c-fos ARE into the rabbit beta-globin gene, results in a destabilised transcript despite the continued presence of mRNA stability elements (Shyu, A et al. 1989). Both alpha- and beta-globin mRNAs contain stability elements that have been mapped to their respective 3'-UTRs, whereas zeta-globin mRNA lacks these elements and is less stable. Replacing the zeta-globin 3'-UTR with that of alpha globin mRNA nearly doubles mRNA stability (Russell, J et al. 1998). However, such elements do not stabilise all transcripts. Therefore, the requirements for generating an expression vector that expresses a stable mRNA differ, dependent on the original mRNA that is to be stabilised. To create such a vector it is generally preferable to include large segments from a stable gene such as alpha- or beta-globin. With these examples, such segments should preferably include the entire globin 3'-UTR, replacing the endogenous 3'-UTR. As exemplified with zeta-globin, this is sometimes sufficient. However, the further incorporation of protein-coding and/or 5'-UTR sequences is often required. Generally, it is preferable to replace any endogenous AU- or U-rich regions, which may act as dominant destabilising elements (these can be identified using the techniques described herein). Such regions in the 5'-UTR or 3'-UTR are simply replaced with alpha- or beta-globin sequences from the same relative position. Instability elements from the coding region can be rendered non-functional by mutation to synonymous codons. The globin protein-coding region can be incorporated into the coding region of the gene of interest to create an N- or C-terminal fusion protein. However this is often not desirable and it is generally sufficient to localise the globin protein-coding region (and 3'-UTR) into the 3'-UTR of the chimeric gene. This allows expression of the desired protein from a more stable transcript, thus markedly increasing levels of the protein. When the desired protein is a reporter or is fused to a reporter or can be easily distinguished from endogenous protein, the TRE vector system described herein (see FIG. 7) greatly facilitates the testing of chimeric constructs for mRNA stability.

Example 17

Further Evidence of the Versatility and Effectiveness of the System

To further demonstrate the applicability of the destabilising system to a number of different reporters and applications, the inventor constructed a wide range of reporter vectors, with and without a mRNA destabilising element (N4; 4 copies of the nonamer TTATTTATT [SEQ ID NO:13]), and with or without a protein-destabilising element (MODC PEST sequences at carboxy-end and/or ubiquitin sequences at the N-end). The TRE promoter was utilised, which is repressed in response to doxycycline and slightly enhanced by PMA or a synthetic promoter comprised of 4 copies of the NF-κB-binding sequence, which is more strongly enhanced by PMA. The inventor also utilised the following reporter proteins; EGFP, EYFP, ECFP, HcRed, firefly luciferase, Renilla luciferase and beta galactosidase.

Reporter constructs were assembled in the pGL3 vector backbone using standard cloning techniques. Essentially, the reporter genes comprised:

Sac1—promoter and 5'-UTR—Bgl2-Age1-Kozak—START—reporter protein encoding—Hind3—MODC-PEST-encoding—STOP-XbaI—N4—SV40—pA—Sal1;
for the destabilised variants and:

Sac1—promoter and 5'-UTR—Age1-Kozak-START—reporter protein encoding—STOP-XbaI—SV40 pA—Sal1;
for the standard reporter genes.

Reporter protein-encoding sequences were typically obtained by PCR of standard commercial vectors and cloned into the abovementioned vectors by utilising a forward primer containing an Age1 site and a Kozak sequence and a reverse primer containing either a Hind3 site (but no STOP codon) to create the destabilised reporter protein or an XbaI site (downstream of the STOP codon) for the stable (standard) reporter protein. The N4 mRNA destabilising sequence was conveniently included or excluded from specific vectors by substituting the XbaI-Sal1 fragments shown above that either contain or do not contain N4. In some specific vectors, N-terminal fusions were created by inserting in frame and into the Age1 site; a human ubiquitin sequence, preceded by a Kozak sequence and followed by a short N-terminal destabilising element (generated by PCR of human genomic DNA) and/or the puromycin-resistance gene (without stop codon; generated by PCR of pBabe-puro). The Quick Change method (Invitrogen) was used to make small mutations including conversion of the wild-type ubiquitin sequence to a non-cleavable mutant (Gly-Val substitution in last amino acid residue of ubiquitin).

Nomenclature (Additive to that Shown in Example 14):
B (at start of name of all vectors)=Vector backbone derived from Promega's pGL3-Basic.

Promoters:
T=Tetracycline-responsive element (TRE), including the minimal CMV promoter/5'-UTR sequence, derived from Clontech's pTRE-d2EGFP vector.
N (following B)=4 tandem copies of the NFkB-binding site followed by the minimal CMV promoter/5'-UTR.

N-Terminal Fusion Sequences:
u=ubiquitin coding sequence followed by arginine and destabilising N-terminal peptide.
mu=mutant (non-cleavable ubiquitin).
puro=sequence encoding puromycin-resistance.
neo=sequence encoding neomycin-resistance.

Parental Reporter Sequences:
G=EGFP coding (alone or as fusion).
Y=EYFP coding (alone or as fusion).
C=ECFP coding (alone or as fusion).
H=HcRed coding (alone or as fusion).
R=DsRed2 used as the reporter.
L=Firefly luciferase coding sequence (alone or as fusion).
Rn=Renilla luciferase coding sequence (alone or as fusion).
B (in middle of name)=beta-galactosidase coding sequence (alone or as fusion).

C-Terminal Fusion Sequences:
1=the mutated, MODC-derived, PEST sequence as present in d1EGFP-N1 (Clontech).
2=the mutated, MODC-derived, PEST sequence as in pTRE-d2EGFP (Clontech).

3'-UTR Additions:
N4=4 copies of the nonamer TTATTTATT [SEQ ID NO:13] inserted into the 3'-UTR-encoding region.

Figure 15:
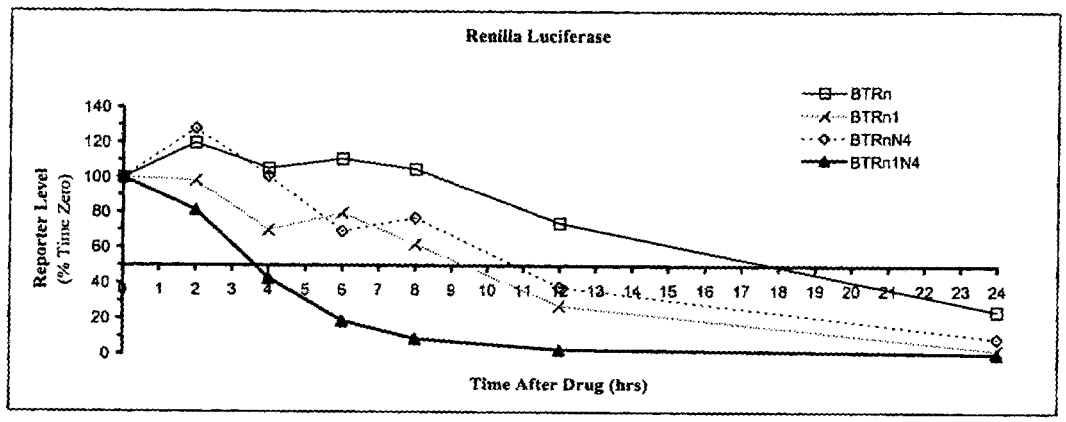
FIG. 15 is a graphical representation showing a time-course similar to that described in FIG. 7. Five micrograms of each plasmid was transfected into Tet-Off HeLa cells (Clontech) using Lipofectamine 2000 (Gibco BRL). Six to eight hours later, the contents of each flask (transfection) was split into multiple dishes. Twenty four hrs after transfection, a drug (doxycycline) known to inhibit transcription from the TRE promoter contained in each vector was added to a final concentration of one microgram per mL and the cells were harvested at the time-points shown. Reporter levels (luminescence) were measured using the Dual Luciferase Assay kit (Promega) and a luminometer (Wallac) and expressed as a % of time zero. Each plasmid was constructed using the pGL3-Basic vector backbone (initial B in plasmid name), with the TRE promoter (T in plasmid name) placed upstream of the *Renilla* luciferase coding sequence (Rn in plasmid name). Thus, BTRn contains the standard *Renilla* luciferase reporter. In BTRn1, the mutant MODC protein-destabilising sequence (identical to that in the d1EGFP vector (Clontech) was fused, in frame, to the 3' end of the *Renilla* luciferase sequence and is denoted by the number 1 immediately after the reporter (Rn) symbol. In BTRnN4, 4 copies of the mRNA destabilising nonamer TTATTTATT (denoted by N4 in the plasmid name) were placed into the 3'-UTR-encoding region. In BTRn1N4, both the protein (1)- and mRNA (N4)-destabilising sequences were incorporated. The standard *Renilla* luciferase reporter decayed very slowly, reaching 50% of initial values after 18 hrs. Modified reporter vectors incorporating either the protein-destabilising element (BTRn1) or the mRNA-destabilising element (BTRnN4) decayed more rapidly, reaching 50% values at 9–11 hrs. However, the vector containing both protein- and mRNA-destabilising elements, showed, by far, the most rapid response and reached 50% in about 3.5 hrs.
Figure 16:
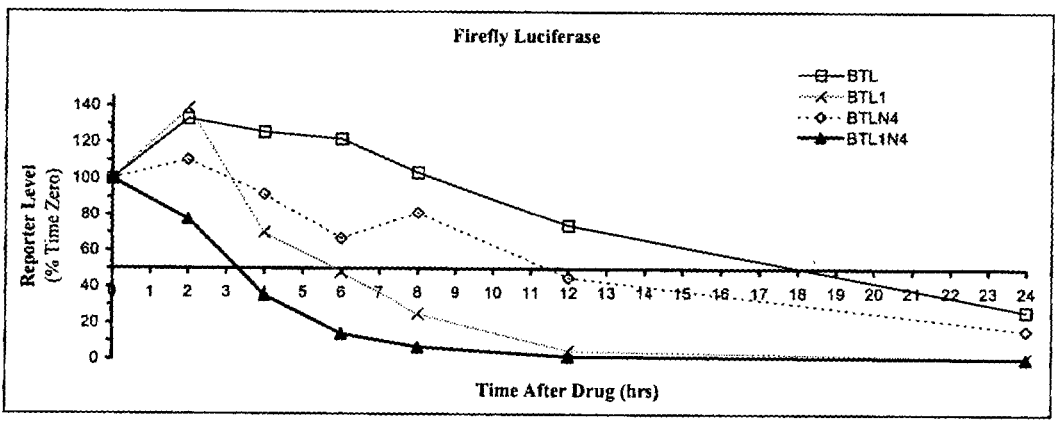
FIG. 16 is a graphical representation showing a time-course similar to that described in FIG. 15, except using plasmids containing the Firefly luciferase reporter (L in plasmid name). As seen with *Renilla* luciferase, the standard Firefly luciferase (BTL) decays slowly, taking 18 hrs to reach 50%. Modified reporter vectors incorporating either the protein-destabilising element (BTL1) or the mRNA-destabilising element (BTLN4) decayed more rapidly. However, the vector containing both protein- and mRNA-destabilising elements, showed, by far, the most rapid response and reached 50% in about 3.5 hrs.
Figure 17:
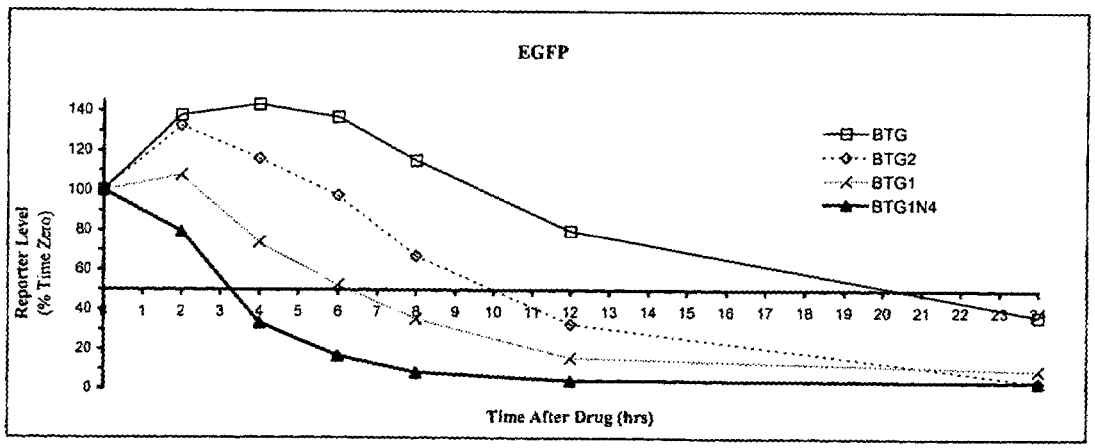
FIG. 17 is a graphical representation showing a time-course similar to that described in FIG. 15, except using plasmids containing the enhanced green fluorescent protein (EGFP) reporter (G in plasmid name). Reporter levels were measured by flow cytometry and analysed using FlowJo software. Briefly, the percentage of positive cells was determined at time zero and used to assign a "percentile" corresponding to the median of the positive cells. The fluorescence of that percentile was then measured at all time points and expressed as a percentage of the time zero value. As seen with the luciferase vectors, the standard EGFP (BTG) decays slowly, taking ~20 hrs to reach 50%. Using Clontech's destabilised, d2EGFP reporter, with a reported protein half-life of 2 hrs (BTG2), the time to 50% was reduced to ~10 hrs and this was further reduced to ~6.3 hrs by substituting in the stronger protein-destabilising motif from d1EGFP (BTG1). However, the vector further containing the mRNA-destabilising element (BTG1N4), showed, by far, the most rapid response and reached 50% in ~3.3 hrs.
Figure 18:
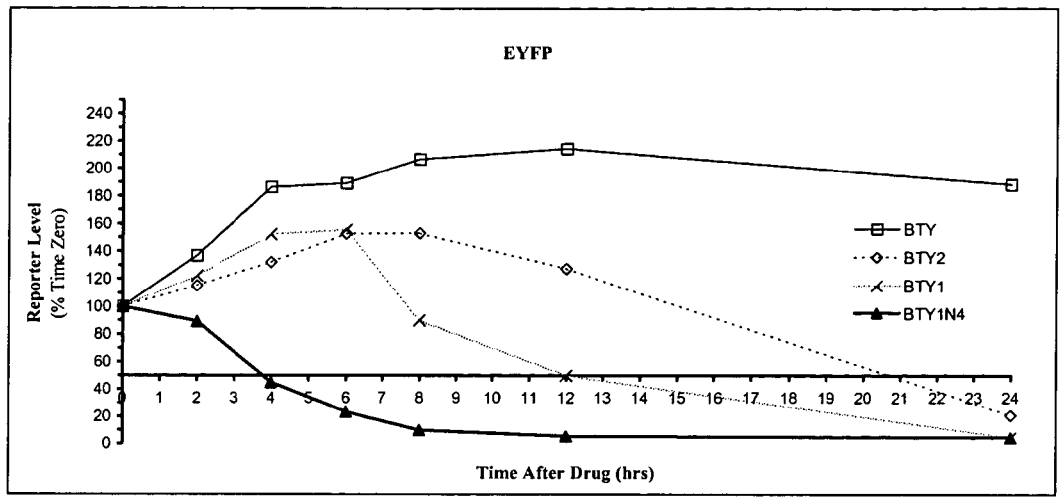
FIG. 18 is a graphical representation showing a time-course similar to that described in FIG. 15, except using plasmids containing the enhanced yellow fluorescent protein (EYFP) reporter (Y in plasmid name). As seen with other standard reporter vectors, the standard EYFP (BTY) decays slowly, taking >24 hrs to reach 50%. Using Clontech's destabilised, d2EYFP reporter, with a reported protein half-life of 2 hrs, the time to 50% was reduced to ~20.5 hrs (BTY2) and this was further reduced to ~12 hrs by substituting in the stronger protein-destabilising motif from d1EGFP (BTY1). However, the vector further containing the mRNA-destabilising element (BTY1N4) showed, by far, the most rapid response and reached 50% in ~4 hrs.
Figure 19:
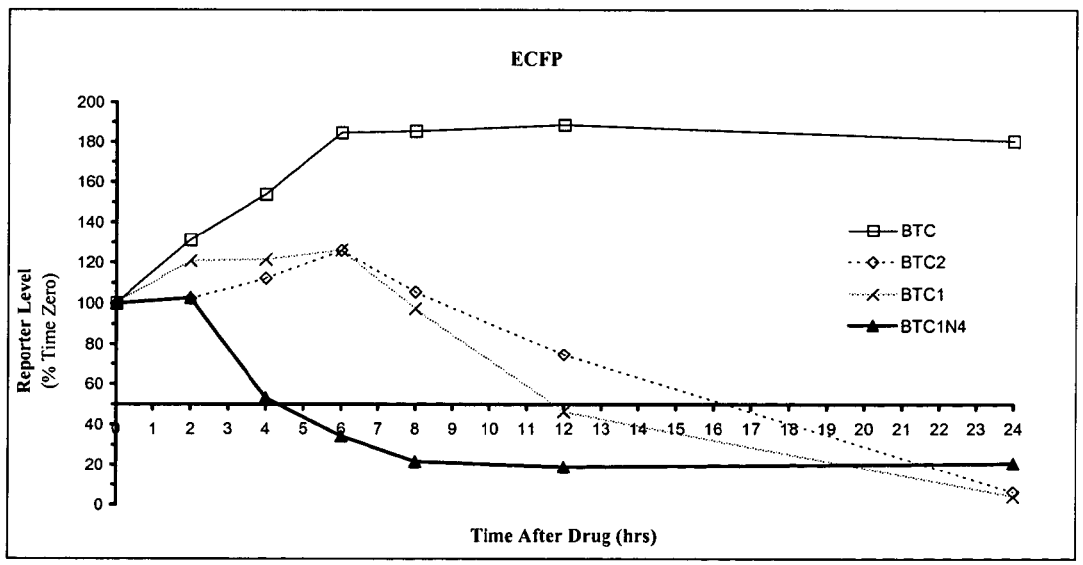
FIG. 19 is a graphical representation showing a time-course similar to that described in FIG. 15, except using plasmids containing the enhanced cyan fluorescent protein (ECFP) reporter (C in plasmid name). As seen with other standard reporter vectors, the standard ECFP (BTC) decays slowly, taking >24 hrs to reach 50%. Using Clontech's destabilised, d2ECFP reporter, with a reported protein half-life of 2 hrs, the time to 50% was reduced to ~16.5 hrs (BTC2) and this was further reduced to ~12 hrs by substituting in the stronger protein-destabilising motif from d1EGFP (BTC1). However, the vector further containing the mRNA-destabilising element (BTC1N4) showed, by far, the most rapid response and reached 50% in ~4.3 hrs.

Each TRE-containing plasmid was evaluated for its rate of response (in reporter levels) to an inhibition of transcription. Briefly, each vector in a series was transfected into Tet-Off HeLa cells, then split into multiple dishes. Reporter levels were measured during a time-course after addition of doxycycline (which inhibits transcription from TRE), as described in the legends to FIGS. 15 and 17. For convenience, FIGS. 15–24 all show the standard vectors as open squares on a thin line and the fully destabilised vector as closed triangles on a bold line.

Figure 20:
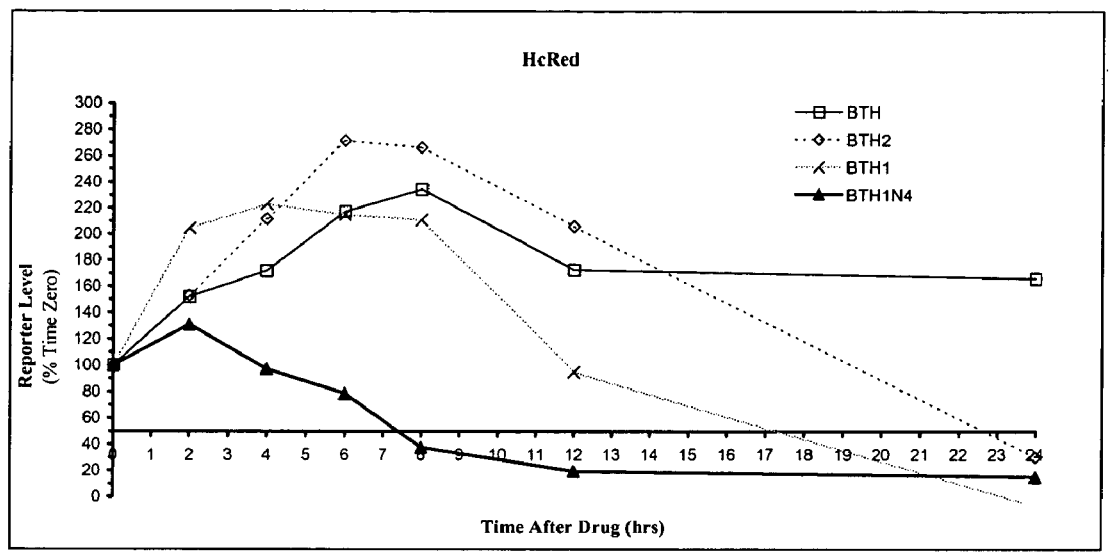
FIG. 20 is a graphical representation showing a time-course similar to that described in FIG. 15, except using plasmids containing the HcRed red fluorescent protein (Clontech) reporter (H in plasmid name). As seen with other standard reporter vectors, the standard HcRed (BTH) decays slowly, taking >24 hrs to reach 50%. Fusing this reporter gene to the MODC fragment from d2EGFP reduced this time to ~22.5 hrs (BTH2) and this was further reduced to ~17 hrs by substituting in the stronger protein-destabilising motif from d1EGFP (BTH1). However, the vector further containing the mRNA-destabilising element (BTH1N4) showed, by far, the most rapid response and reached 50% in ~7.3 hrs (4–7 hrs in repeat experiments).
Figure 21:
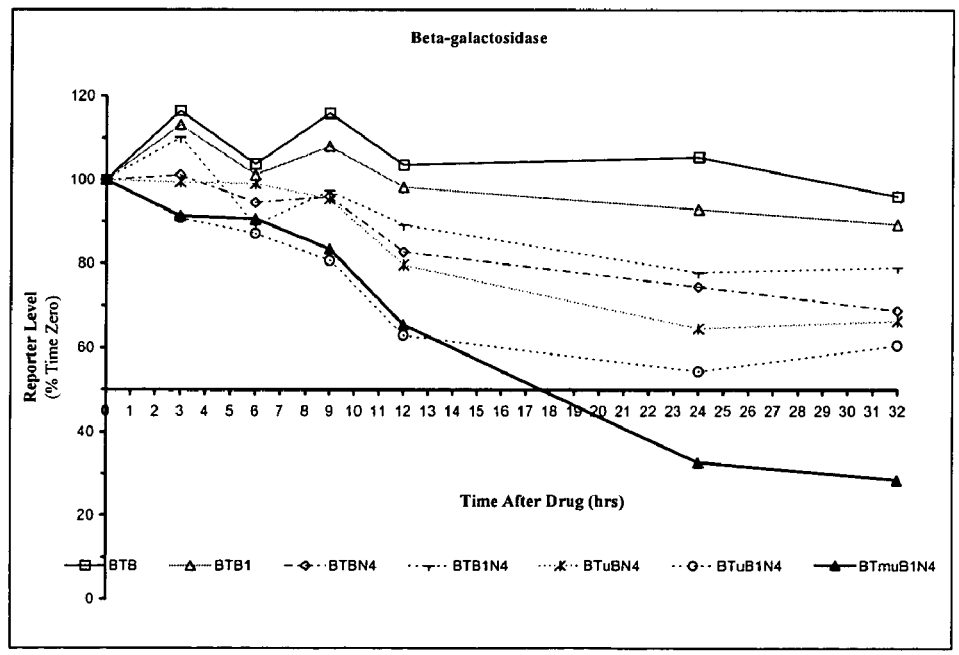
FIG. 21 is a graphical representation showing a time-course similar to that described in FIG. 15, except using plasmids containing the beta-galactosidase reporter (B in plasmid name) from pSV-beta galactosidase (Promega). The standard beta-galactosidase reporter (BTB) showed little, if any decay in activity over 32 hrs. Fusing this reporter gene to the MODC fragment from d1EGFP (BTB1) caused a slight increase in decay rate but a faster decay was seen with the vectors further containing the mRNA-destabilising element (BTB1N4) or containing the mRNA-destabilising element alone (BTBN4). These latter 2 vectors were further modified (BTuB1N4 and BTuBN4 respectively) to incorporate a ubiquitin sequence (u in reporter name), at the 5' end of the protein-coding sequence, such that upon cleavage of the ubiquitin, the remaining (modified) beta galactosidase protein contains an N-terminal amino acid sequence beginning with arginine and shown to destabilise proteins via the N-end rule. These ubiquitin-fusion vectors showed more rapid decay but the fastest decay was achieved with BTmuB1N4, which contains a mutant (non-cleavable) ubiquitin sequence at the 5' coding sequence (mu in reporter name), the MODC fragment at the 3' coding sequence and the four nonamers in the 3'-UTR sequence.
Figure 22:
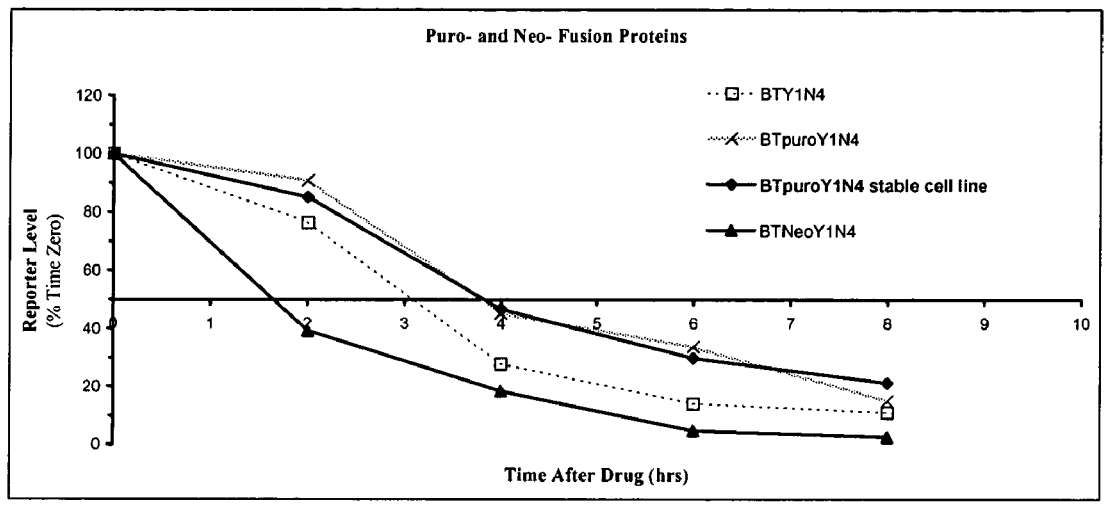
Figure 22:
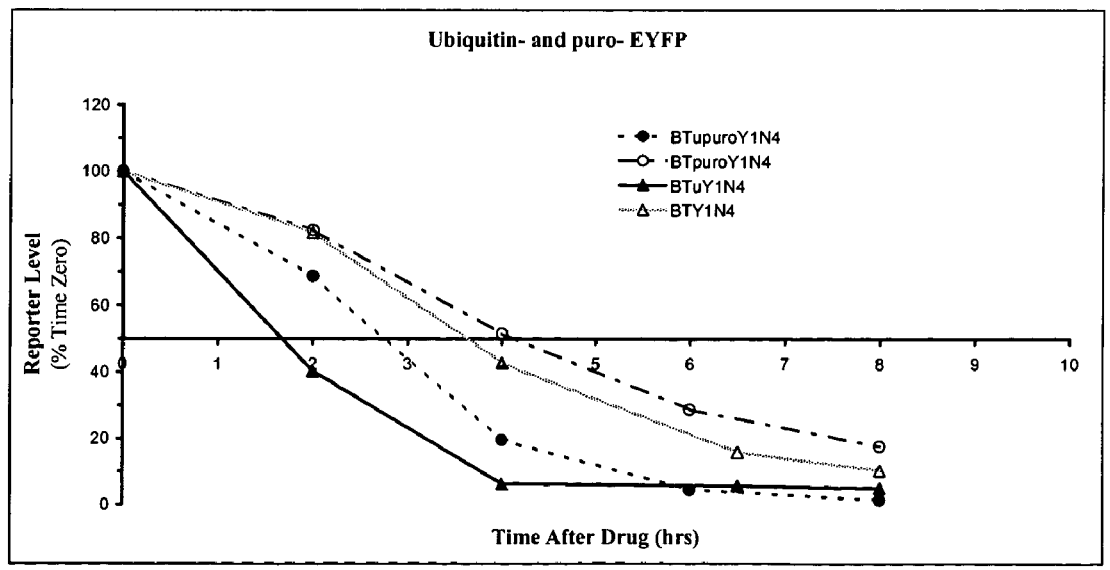
Figure 23:
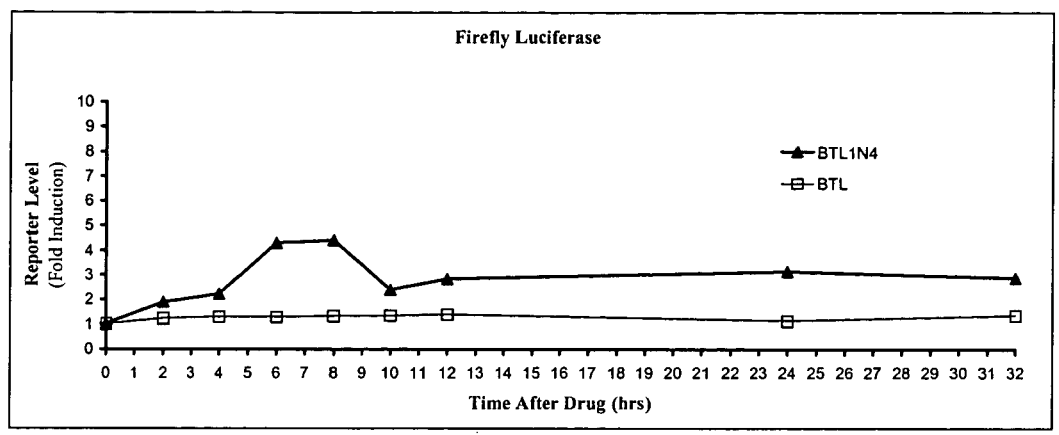
FIG. 23 is a graphical representation showing a time-course following activation of transcription via addition of a drug. In this experiment, the drug was PMA (50 ng/mL) and the vectors contained the TRE promoter followed by the firefly luciferase coding sequence, either without (BTL) or with (BTL1N4) the protein- and mRNA-destabilising elements. Two separate experiments were performed (FIGS. 23A and 23B) and both show a 4–5 fold increase in levels of the destabilised reporter (BTL1N4) following PMA. In contrast, the standard, stable reporter shows little detectable change after PMA. These data show that a moderate increase in transcription is easily detectable with BTL1N4 but is virtually undetectable with the standard reporter (BTL).
Figure 23:
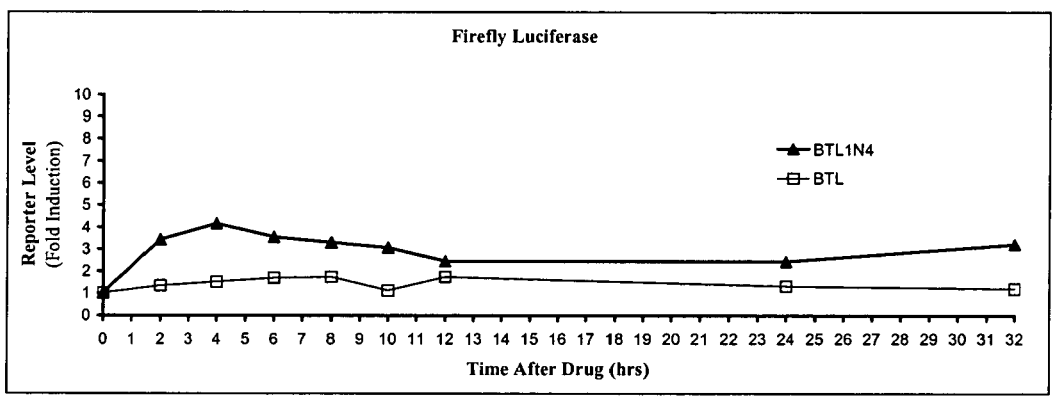

In all cases, both mRNA- and protein-destabilising elements were shown to improve the rate of response to drug (effective decay after doxycycline). In particular, the combination of the d1 MODC protein degradation signal plus the N4 mRNA-degradation signal (i.e., vectors ending in 1N4) resulted in a very rapidly responding Renilla luciferase (FIG. 15), firefly luciferase (FIG. 16), EGFP (FIG. 17), EYFP (FIG. 18), ECFP (FIG. 19) and HcRed (FIG. 20). The further addition of an N-terminal ubiquitin sequence resulted in further destabilisation of EYFP (FIG. 22B) and beta galactosidase (FIG. 21).

Figure 24:
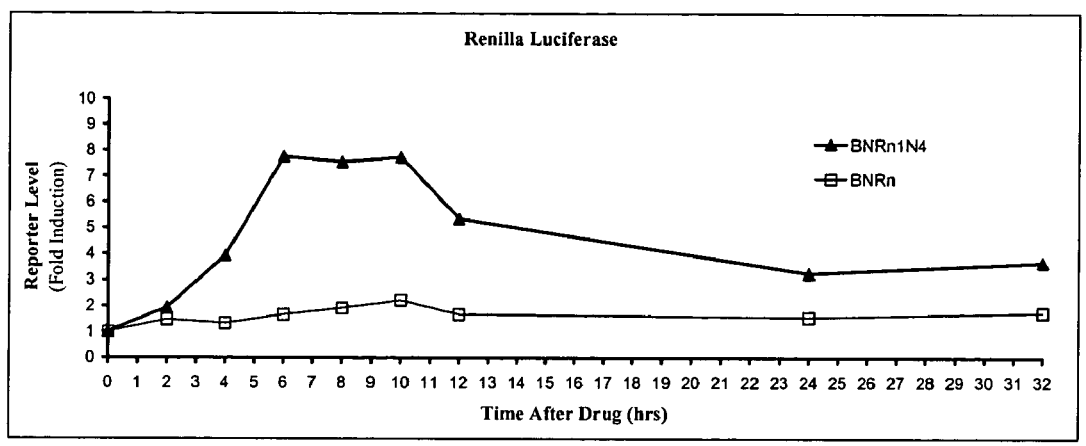
FIG. 24 is a graphical representation showing a time-course following activation of transcription via addition of a drug. As in FIG. 23, the drug was PMA (50 ng/mL). However, the vectors in this series contained the *Renilla* luciferase coding sequence, either without (BNRn) or with (BNRn1N4) the protein- and mRNA-destabilising elements. Moreover, the promoter was comprised of 4 copies of the NFkB binding sequence (N in vector name) in place of the TRE promoter. Compared to the TRE, NF-κB is more strongly activated by PMA. Two separate experiments were performed (FIGS. 24A and 24B) and both show an ~8–10 fold increase in levels of the destabilised reporter (BNRn1N4) following PMA. In contrast, the standard, stable reporter (BNRn) shows only a ~2 fold increase after PMA. These data, together with the decay data (e.g.
Figure 24:
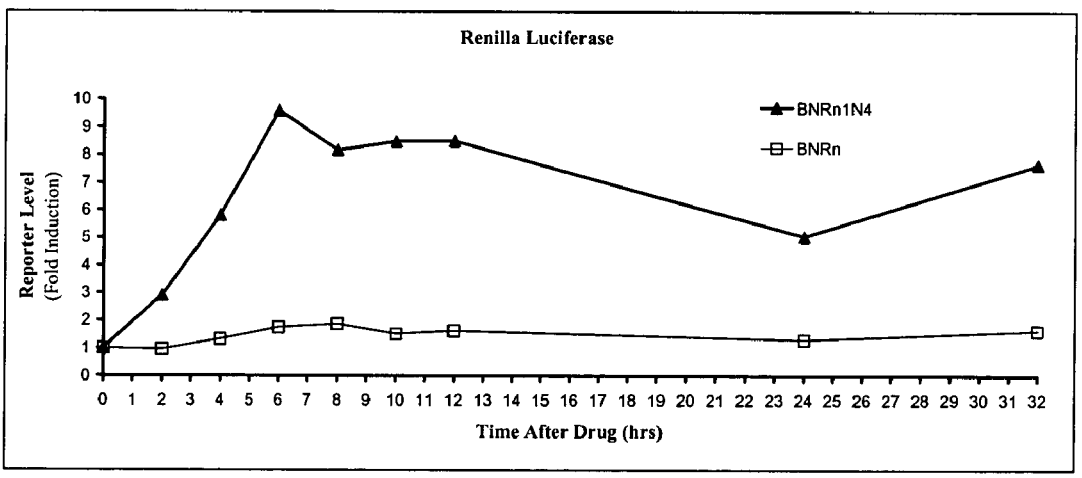
Figure 25:
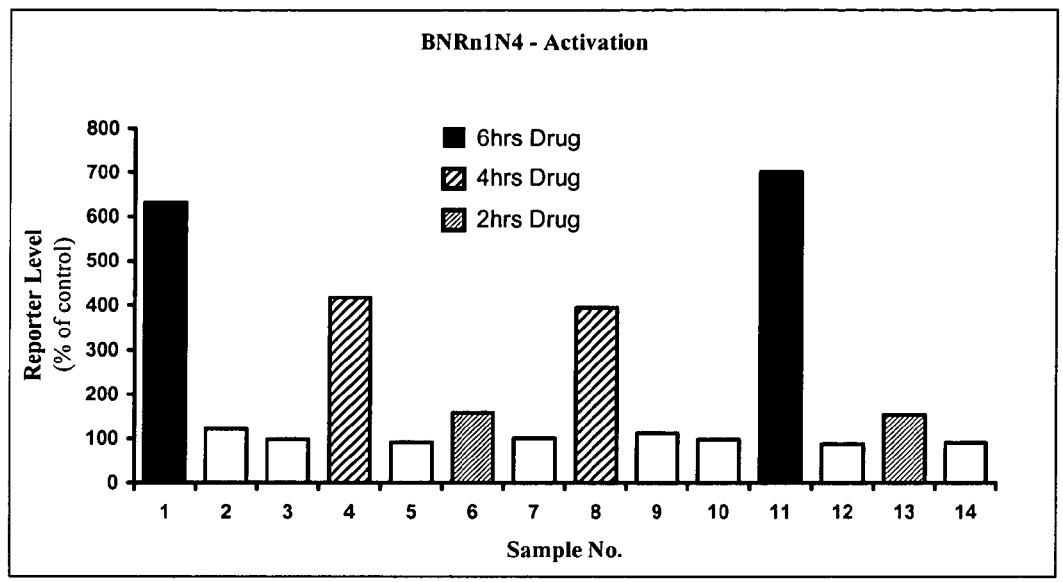
FIG. 25 is a graphical representation of an experiment designed to mimic a high-throughput drug-screening assay that utilises either the mRNA- and protein-destabilised (FIG. 25A) or standard (FIG. 25B) *Renilla* luciferase reporters. Cells were transfected with the indicated plasmids as described in FIG. 15, except that 6–8 hrs after transfection, the cells were trypsinised, counted and then seeded into the wells of a 96-well plate at a density of ~20,000 cells/well. At 24, 26 and 28 hrs post-transfection, PMA (or carrier control; ethanol) was added to 2 wells to create duplicate samples representing 2, 4 and 6 hrs drug treatment plus controls. At 30 hrs, the media was removed, the cells lysed within their wells using Passive Lysis Buffer (Promega), and reporter activity quantified as described in FIG. 15. The raw data (without indication of the drug-treated samples) were transferred to another scientist, who plotted the data and attempted to identify the samples containing active drug. This proved very easy with the destabilised vector (BNRn1N4), even for the shortest drug treatment. With the standard vector (BNRn), however, only the longest drug treatments could be identified and these showed only a modest 50% increase, compared to 600–700% with the destabilised vector. The identities of the drug treated samples were cross-checked and are indicated by symbols in FIG. 25A (BNRn1N4) and FIG. 25B (BNRn).
Figure 25:
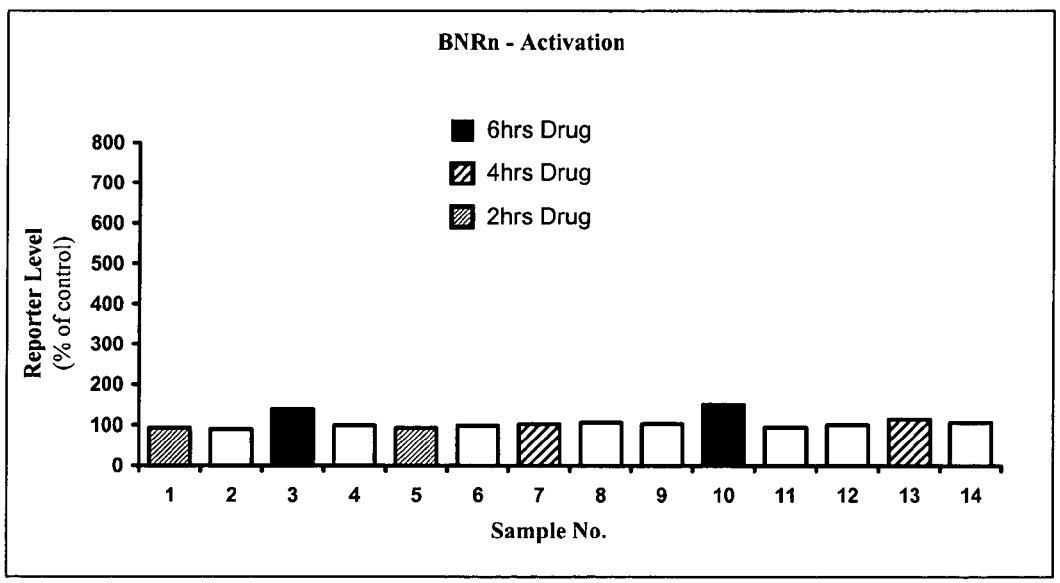
Figure 26:
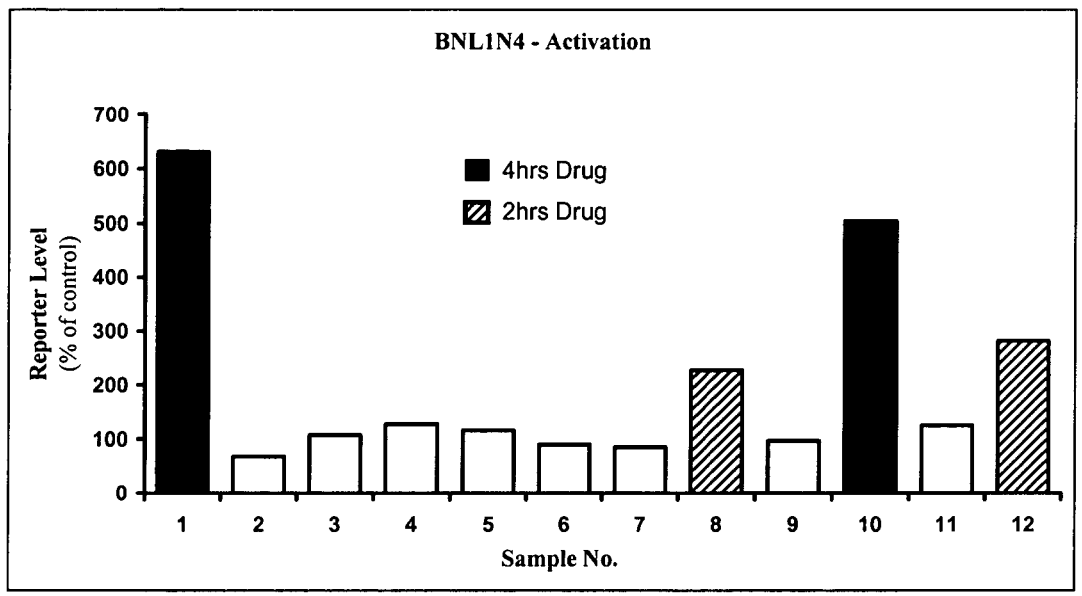
FIG. 26 is a graphical representation of an experiment that is essentially identical to that shown in FIG. 25, except that the reporter was firefly luciferase and only two different drug treatments (2 hr and 4 hr) were performed. As seen with *Renilla* luciferase, the performance of firefly luciferase was also substantially improved by destabilising the mRNA and protein (BNL1N4.
Figure 26:
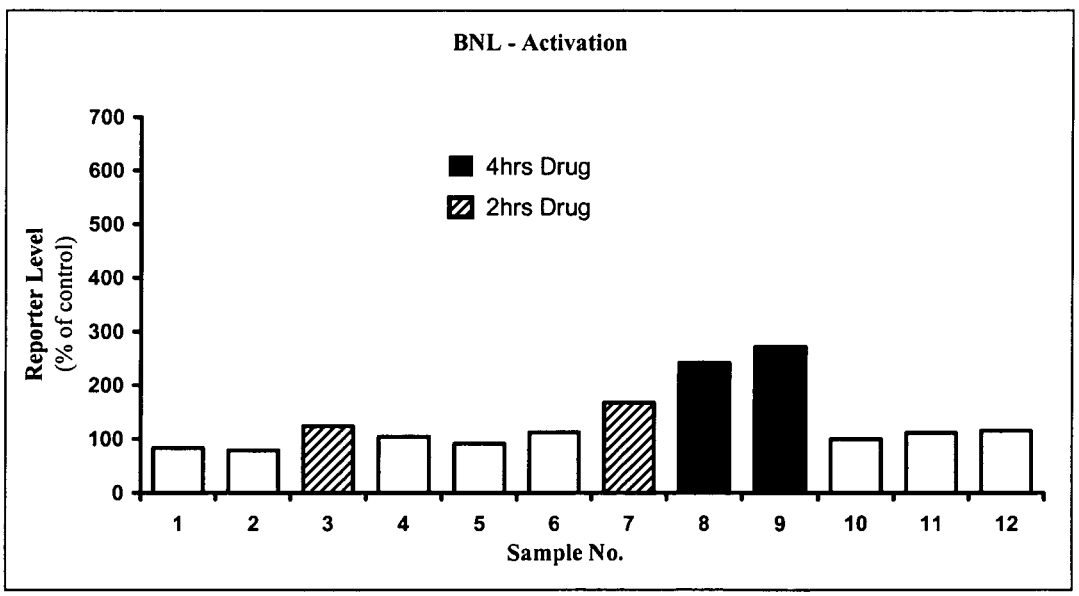
Figure 27:
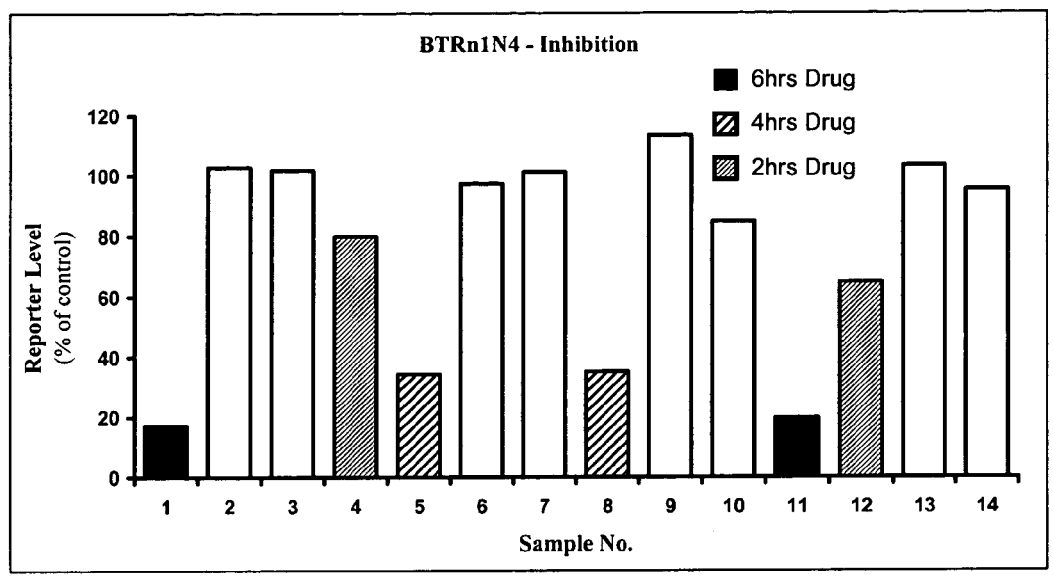
FIG. 27 is a graphical representation of an experiment that is essentially identical to that shown in FIG. 25, except utilising the TRE as the promoter and doxycycline as the drug so as to mimic a screen for drugs that inhibit, rather than activate a pathway leading to transcription. Although the inhibition of reporter transcription (the desired effect) was presumably identical with both vectors, the percentage change in reporter levels (the measurable effect) was greatly enhanced with the mRNA- and protein-destabilised *Renilla* luciferase (BTRn1N4.
Figure 27:
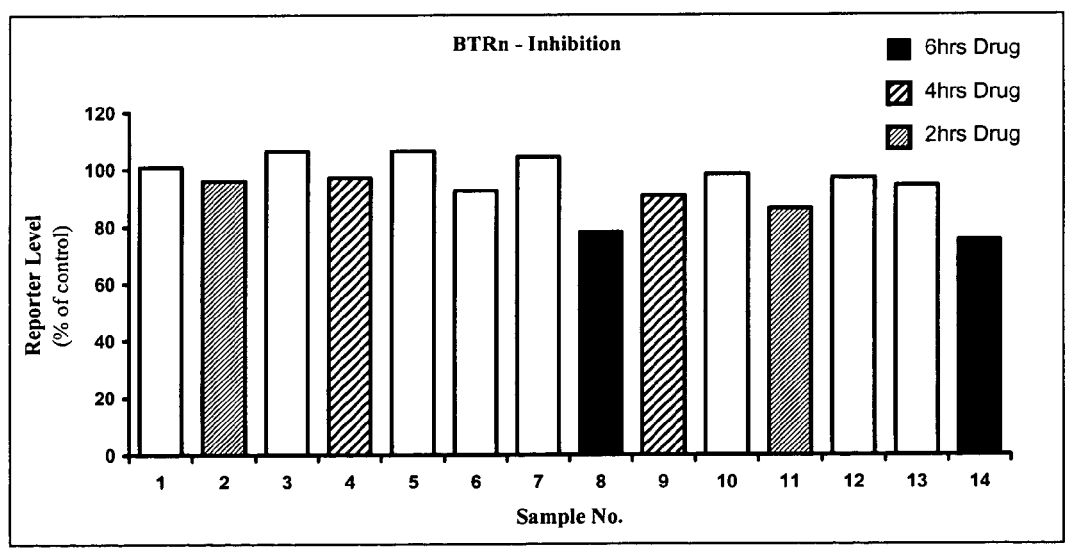

In theory, a more rapidly degrading reporter system such as that described herein, should not only produce faster decay after inhibition but should produce a more rapid accumulation after activation. Indeed, given that most drugs and biological systems involve a transient rather than permanent increase or decrease in expression, the more rapid response of unstable reporters should also lead to a larger maximum effect in such systems. FIG. 24 shows that the destabilised *Renilla* luciferase does indeed show a much larger as well as more rapid increase in reporter levels following activation by PMA. The inventor has also used kinetic models to quantify this effect and showed that the accurate detection of minor or transient changes is virtually impossible with many standard reporters such as luciferases, beta galactosidase and CAT. This theoretical evidence was demonstrated in practice through the experiment depicted in FIG. 23., which shows virtually no change in standard luciferase reporter levels after a small to moderate induction of transcription, whereas a 4–5 fold increase was seen with the destabilised counterpart.

Example 18

Dual-Reporter Vectors for Studying or Measuring Gene Regulation

Dual-reporter bi-directional vectors based on the example shown in FIG. 4B were constructed using standard techniques and using BTH1N4 and BTG1N4 as starting material. In these dual-colour vectors, a single TRE promoter drives transcription of destabilised HcRed in one direction (BTH1N4) and destabilised EGFP in the other (BTG1N4). Convenient unique cloning sites were introduced on the EGFP side at the transcription start site and immediately upstream of the Kozak sequence. Using these cloning sites, a variety of different 5'-UTRs were cloned into the BTG1N4 mRNA encoding region, with the BTH1N4 mRNA encoding region remaining unchanged. As such, red fluorescence serves as an internal control for transfection efficiency, cellular conditions etc. In an additional construct, the EGFP-coding region (from BTG1N4) was fused with the coding region from the puromycin resistance gene to create a puro-GFP fusion protein construct (BTpuroG1N4).

Each construct was transfected into Tet-Off HeLa cells and 24 hrs later, green and red fluorescence was measured simultaneously by flow cytometry and analysed using FlowJo software. When fluorescence was expressed as the relative ratio of green:red fluorescence (FIG. 28A), the effect of these different 5'-UTRs (or puro-GFP fusion protein) on expression levels of GFP could be easily seen. The higher relative expression of GFP in constructs containing the Hsp70 and beta-globin 5'-UTRs is consistent with reports of these UTRs containing translational enhancer sequences. The synthetic 5'-UTR sequence showed an apparently low translational efficiency. The puro-GFP construct appeared to be very efficiently translated and this shows how the vector system can be used to assay the effect on expression levels of protein-coding sequences as well as UTR sequences.

Figure 28:
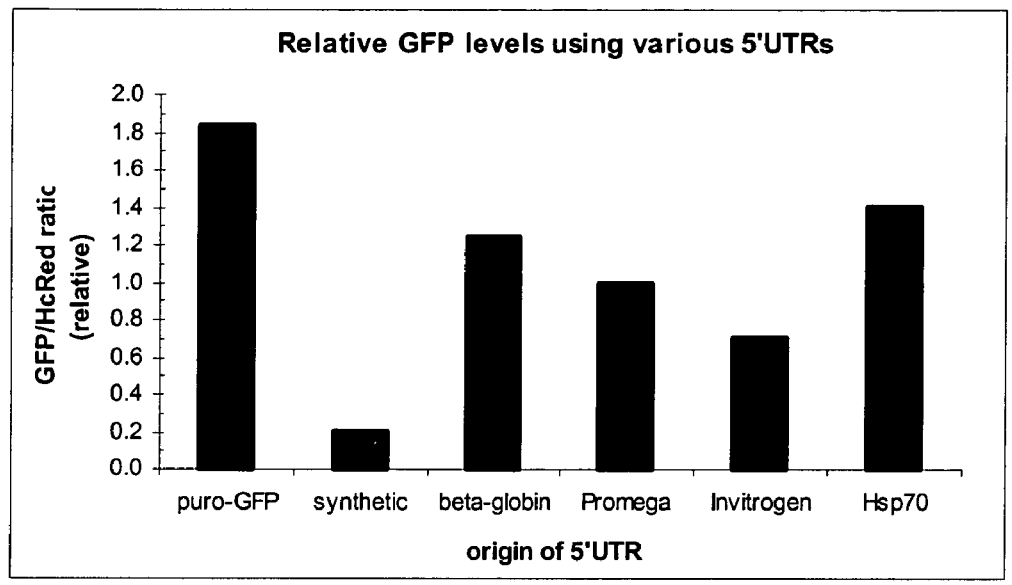
FIG. 28 is a graphical representation of an experiment similar to that described in FIG. 7, except using dual-colour vectors based on the example shown in FIG. 4B. A single TRE promoter drives transcription of destabilised HcRed in one direction (BTH1N4) and destabilised EGFP in the other. (BTG1N4). The 5'-UTR of the EGFP transcript was altered in each construct to contain a synthetic (artificial) UTR, the Hsp70 5'UTR, the beta globin 5'-UTR or the 5'-UTR from standard Promega and Invitrogen reporter vectors. In puro-GFP, the actual EGFP-coding region (from BTG1N4) was fused with the coding region from the puromycin resistance gene to create BTpuroG1N4.
Figure 28:
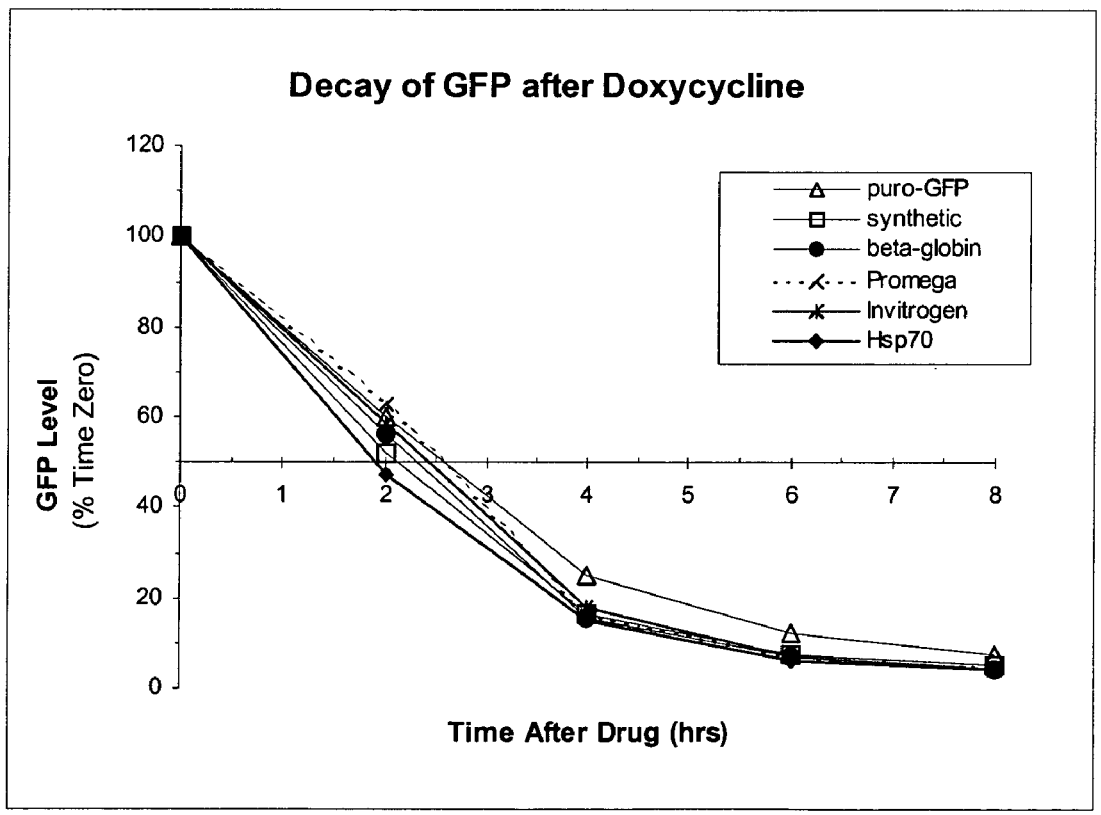

Increased expression caused by a 5'-UTR (or other sequence) could derive not only from increased translational efficiency but also from increased mRNA stability or enhancement of transcription. An important feature of the embodiment exemplified here is the ability to distinguish these possibilities. A transcriptional enhancer, by definition, acts independently of orientation and if present in a sample 5'-UTR, would enhance transcription from the TRE in both directions and thus increase both red and green fluorescence. A co-transfected control vector would assist in identifying such transcriptional enhancers, which would not be expected to alter the green:red ratio in the manner shown in FIG. 28A. An effect on mRNA stability is a likely consequence of altered 5'-UTR sequence and with standard reporter systems this mRNA stability effect cannot be distinguished from a translational effect. However, FIG. 28B shows that all 6 constructs have similar rates of decay in GFP fluorescence after doxycycline was added to the cells expressing these constructs, in order to block transcription from the TRE promoter. Therefore, it can be inferred that the different 5'-UTR sequences did not affect mRNA stability and instead must have altered translational efficiency.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

Tables

TABLE 1

Signal transducers that could be used in the present invention
Signal transducer

| AKT (also called PKB) |
| Fas L/BID |
| JAK 7 Stat |
| MKK-47/JNK |
| MTOR/p70 s6 kinase |
| NFκB |
| p38 |
| PKA/Rap1 B-raf |
| Ras/Raf |
| Wnt/GSK3 |
| Erk 1 & 2 |

BIBLIOGRAPHY

Chen, C and Shyu, A. Trends Biochem. Sci. 1995: vol 20 465–470.

Chyi-Ying, A et al. MCB 1995: vol 15 (10) 5777–5788.

Contag, et al. Non-invasive localization of a light-emitting conjugate in a mammal U.S. Pat. No. 5,650,135. Jul. 22, 1997.

Cormack, et al. FACS-optimized mutants of the green fluorescent protein (GFP) U.S. Pat. No. 5,804,387. Sep. 8, 1998.

Dandekar T et al Bioinformation 1998: 14(3):271–278.
Darzynkiewicz. Laser-scanning cytometry: A new instrumentation with many applications. Exp Cell Res 1999; 249:1–12.
Gallie, D et al. Nucleic Acids Res. 1996: vol 24 (10); 1954–1962.
Gasdaska, J R et al. JBC 1999:vol 274 (36); 25379–25385.
Gossen, et al. Tight control of gene expression in eucaryotic cells by tetracycline-responsive promoters. U.S. Pat. No. 5,464,758. Nov. 7, 1995.
Gramolini, A, et al. JBC 2001: vol 154 (6) 1173–1183.
Henics, T. et al JBC 1999: vol 274 (24) 17318–17324.
Holcik and Liebhaber, 1997, PNAS vol 94 pp 2410–2414.
Huet, X et al. Mol Cell Biol. 1996; vol 16 (7): 3789–3798.
Ibrahim, et al. Pitfall of an internal control plasmid: Response of *Renilla* luciferase (pRL-TK) plasmid to dihydrotestosterone and dexamethasone. Biotechniques 2000; 29:682–684.
Kamentsky et al. Slide-based laser scanning cytometry. Acta Cytol 1997; 41:123–43.
Li, et al. Generation of destabilised green fluorescent protein as a transcription reporter. J Biol Chem 1998; 273: 34970–34975.
Lagnado C et al, MCB, 14:7984–7995, 1994.
Laterza, O F et al Am J Physiol Renal Physiol. 2000: vol 279(5) F866-F873.
Leclerc G et al, Biotechniques 2000, 29(3) 590–595.
Lee, H et al. Gene Expr 1995; vol 4(3): 95–109.
Li, et al. Rapidly degrading GFP-fusion proteins. U.S. Pat. No. 6,130,313 Oct. 10, 2000.
Liu, J et al. JBC 2000; vol 275 (16): 11846–11851.
Newnan, T et al. The Plant Cell 1993: vol 5; 701–714.
Peng, S et al. MCB 1996: vol 6 (4) 1490–1499.
Ross, J. Microbiological Reviews. 1995: vol 59 (3):423–450.
Saito, T et al. Biochem Biophys Res Commun. 1998; vol 252 (3): 775–778.
Schiavone, N et al. FASEB J. 2000: vol 14 174–184.
Shyu et al 1989:Genes & Dev. Vol 3, pp 60–72.
Siebenlist et al., MCB 1986 vol 6 3042–3049,
Stein, J et al. Int J Obes Relat Metab Disord. 1996 March; 20 Suppl 3: S84–90.
Surdej, P and Jacobs-Lorena, M. MCB 1998 vol 18 (5) 2892–2900.
Thomson, A et al. Int. J. Biochem Cell Biol. 1999: vol 3 1; 1139–1152.
Tsien, et al. Modified green fluorescent proteins. U.S. Pat. No. 5,625,048. Apr. 29, 1997.
Tsien, et al. Modified green fluorescent proteins U.S. Pat. No. 5,777,079. Jul. 7, 1998.
Vazhappilly, R and Sucher, N. Neurosci Lett. 2002; vol 318 (3): 153–157.
Xu W et al, MCB, 17(8):4611–4621, 1997.
Yu and Russell MCB September 2001 5879–88.
Zhou, Q et al. MCB 1998: vol 18 (2) 815–826.
Zubiaga et al. MCB 1995; 15:2219–30.

What is claimed is:

1. A recombinant construct comprising in operable linkage: a polynucleotide that encodes a polypeptide comprising a protein-destabilizing element, and a nucleic acid sequence that encodes an RNA destabilizing element that reduces the stability of a transcript encoded by the polynucleotide in a eukaryotic cell, wherein the polynucleotide and the nucleic acid sequence are heterologous to each other.

2. The construct according to claim 1, wherein the protein-destabilizing element is selected from the group consisting of: a PEST sequence, an N-terminal destabilizing amino acid and a ubiquitin.

3. The construct according to claim 1, wherein the polypeptide is a reporter protein.

4. The construct according to claim 3, wherein the reporter protein is an enzymatic protein or a protein associated with the emission of light.

5. The construct according to claim 3, wherein the reporter protein is a fluorescent protein or a luminescent protein.

6. The construct according to claim 3, wherein the reporter protein is selected from the group consisting of: Luciferase, Green Fluorescent Protein, Red Fluorescent Protein, SEAP and CAT.

7. The construct according to claim 1, further comprising a cloning site for introducing a sequence of nucleotides in operable connection with the polynucleotide and the nucleic acid sequence.

8. The construct according to claim 7, wherein the cloning site is a multiple cloning site.

9. The construct according to claim 7, wherein the sequence of nucleotides comprises a transcriptional control element.

10. The construct according to claim 7, wherein the sequence of nucleotides comprises a promoter.

11. The construct according to claim 7, wherein the sequence of nucleotides comprises a cis-acting regulatory element.

12. The construct according to claim 11, wherein the cis-acting regulatory element is selected from the group consisting of: an enhancer of transcription, an enhancer of translation, an enhancer of mRNA splicing, an enhancer of mRNA export, an enhancer of mRNA degradation, a repressor of transcription, a repressor of translation, a repressor of mRNA splicing, a repressor of mRNA export and a repressor of mRNA degradation.

13. The construct according to claim 1, further comprising a polyadenylation sequence.

14. The construct according to claim 1, further comprising a selectable marker.

15. The construct according to claim 1, further comprising an origin of replication.

16. The construct according to claim 1, further comprising a translational enhancer.

17. The construct according to claim 1, which is a vector.

18. The construct according to claim 1, further comprising one or more members selected from the group consisting of:
  a multiple cloning site for introducing a sequence of nucleotides;
  a reporter gene;
  a transcriptional enhancer for enhancing transcription of the polynucleotide;
  a translational enhancer for enhancing translation of the transcript encoded by the polynucleotide;
  a polyadenylation sequence;
  a selectable marker gene;
  an origin of replication;
  an intron; and
  a mRNA nuclear export signal.

19. The construct according to claim 7 or claim 18, further comprising at least one site which is cleavable enzymatically, chemically or otherwise to provide a linearised vector into which PCR amplification products can be directly inserted.

20. The construct according to claim 1, wherein the nucleic acid sequence is from a gene selected from the group consisting of: c-fos, c-jun, c-myc, GM-CSF, IL-3, TNF-alpha, IL-2, IL-6, IL-8, IL-10, Urokinase, bcl-2, SGLT1 (Na(+j-coupled glucose transporter), Cox-2 (cyclooxygenase 2), IL-8, PAI-2 (plasminogen activator inhibitor type 2), beta1-adrenergic receptor and GAP43.

21. The construct according to claim 1, wherein the nucleic acid sequence is SEQ ID NO:19.

22. The construct according to claim 1, wherein the polypeptide is a protein having at least a light-emitting activity and a selection marker activity.

23. The construct according to claim 22, wherein the polypeptide is encoded by a chimeric gene comprising a coding sequence from a gene encoding a light-emitting protein and a coding sequence from a gene encoding a selectable marker protein.

24. The construct according to claim 22, wherein the polypeptide is encoded by a chimeric gene comprising a coding sequence from a gene encoding: a light-emitting protein selected from the group consisting of: Green Fluorescent Protein, Luciferase; and a coding sequence from a gene encoding a selectable marker protein selected from the group consisting of: kanamycin kinase, neomycin phosphotransferase, aminoglycoside phosphotransferase, puromycin N-acetyl transferase, and puromycin resistance protein.

25. An isolated or recombinant cell comprising the construct according to claim 1.

26. The cell according to claim 25, wherein the cell is a eukaryotic cell.

27. The cell according to claim 25, wherein the cell is a mammalian cell.

28. The cell according to claim 25, wherein the cell is a human cell.

29. The cell according to claim 25, wherein the cell is a plant cell.

30. The construct according to claim 1, wherein the RNA destabilizing element comprises an AU-rich element.

31. The construct according to claim 30, wherein the AU-rich element comprises the sequence set forth in SEQ ID NO:1.

32. The construct according to claim 1, wherein the polypeptide is a reporter protein comprising a PEST sequence.

33. The construct according to claim 32, wherein the reporter protein comprises Luciferase.

34. The construct according to claim 32, wherein the reporter protein comprises firefly luciferase.

35. The construct according to claim 32, wherein the reporter protein comprises *Renilla* luciferase.

36. The construct according to claim 1, wherein the RNA destabilizing element comprises an AU-rich element and wherein the polypeptide is a reporter protein that comprises firefly luciferase and a PEST sequence.

37. The construct according to claim 1, wherein the RNA destabilizing element comprises an AU-rich element and wherein the polypeptide is a reporter protein that comprises *Renilla* luciferase and a PEST sequence.

* * * * *